United States Patent
Zhou et al.

(10) Patent No.: US 12,152,066 B2
(45) Date of Patent: Nov. 26, 2024

(54) SMART SINGLE-DOMAIN INTRABODIES WITH PRECISION SWITCHES FOR BIOMEDICAL APPLICATIONS

(71) Applicant: THE TEXAS A&M UNIVERSITY SYSTEM, College Station, TX (US)

(72) Inventors: Yubin Zhou, College Station, TX (US); Tianlu Wang, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 146 days.

(21) Appl. No.: 17/519,029

(22) Filed: Nov. 4, 2021

(65) Prior Publication Data
US 2022/0135630 A1    May 5, 2022

Related U.S. Application Data

(60) Provisional application No. 63/109,377, filed on Nov. 4, 2020.

(51) Int. Cl.
| | |
|---|---|
| *C07K 14/71* | (2006.01) |
| *A61K 47/65* | (2017.01) |
| *C07K 14/47* | (2006.01) |
| *C07K 16/10* | (2006.01) |

(52) U.S. Cl.
CPC .............. *C07K 14/71* (2013.01); *A61K 47/65* (2017.08); *C07K 14/47* (2013.01); *C07K 16/1003* (2023.08)

(58) Field of Classification Search
None
See application file for complete search history.

(56) References Cited

PUBLICATIONS

Chang et al., "A Modular Receptor Platform to Expand the Sensing Repertoire of Bacteria", ACS Synth. Biol. 7: 166-175 (Year: 2018).*
Chang et al., "A Modular Receptor Platform to Expand the Sensing Repertoire of Bacteria", ACS Synth. Biol. 7: 166-175 Supplemental Material PDF 1-22 pages. (Year: 2018).*
Franco et al., "Production and characterization of a genetically engineered anti-caffeine camelid antibody and its use in immunoaffinity chromatography", 878: 177-186 (Year: 2010).*

* cited by examiner

*Primary Examiner* — Anand U Desai
(74) *Attorney, Agent, or Firm* — Barnes & Thornburg LLP

(57) ABSTRACT

The present disclosure provides intrabody compositions comprising i) an intrabody and ii) one or more inserts. The disclosure also provides methods for activating and deactivating intracellular and extracellular interactions utilizing the compositions, for instance via chemical and/or light.

20 Claims, 41 Drawing Sheets
Specification includes a Sequence Listing.

FIG. 2G
FIG. 2H
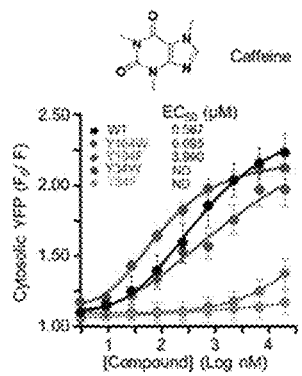
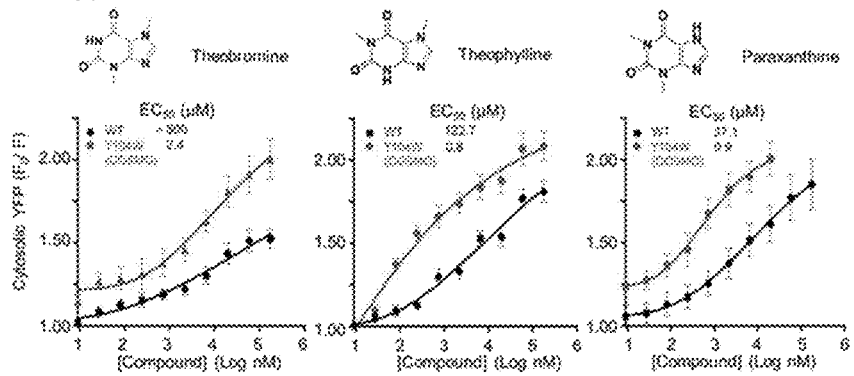
FIGS. 2A-2H

FIG. 3A
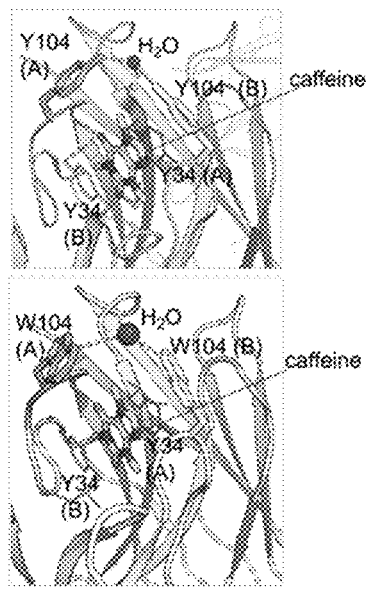
FIG. 3B
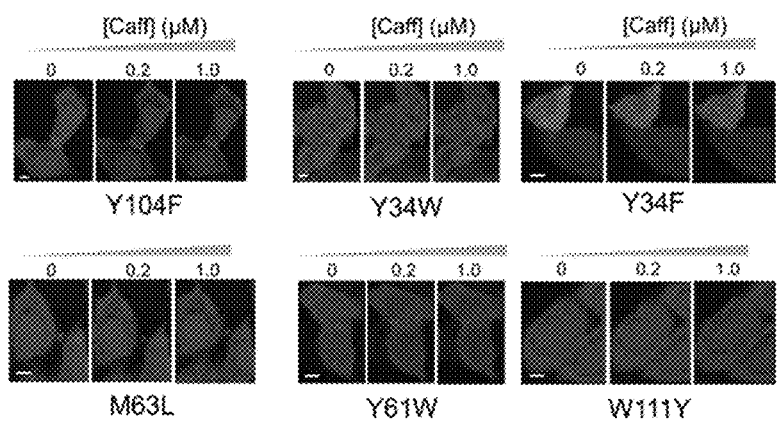
FIG. 3C
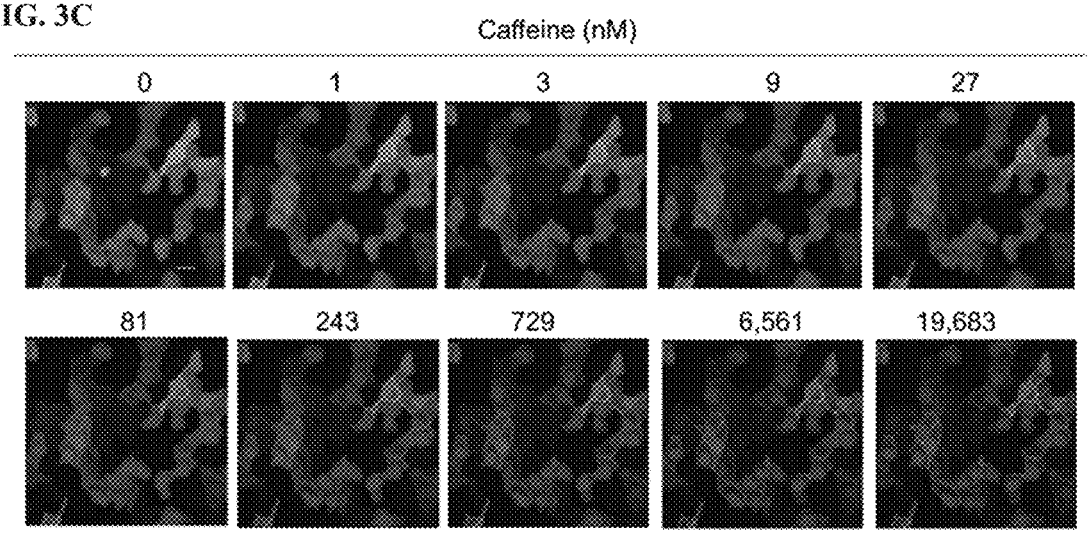
FIGS. 3A-3C

FIG. 4E 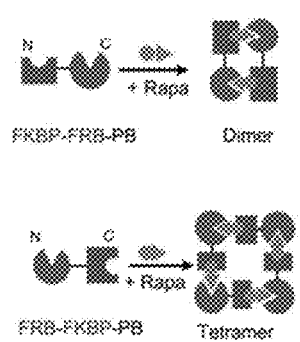 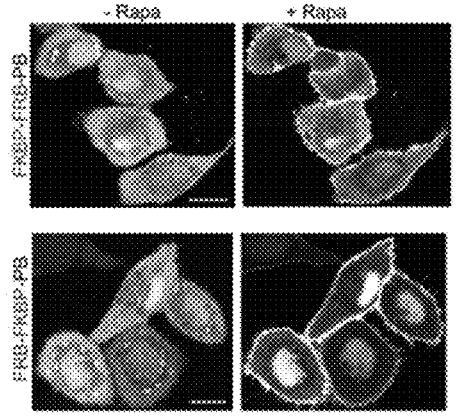 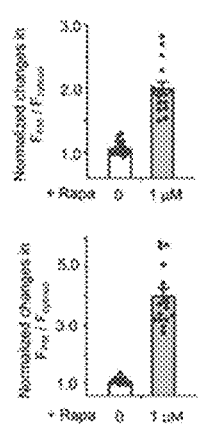
FIGS. 4A-4E

FIG. 6A
Caffeine
Theobromine
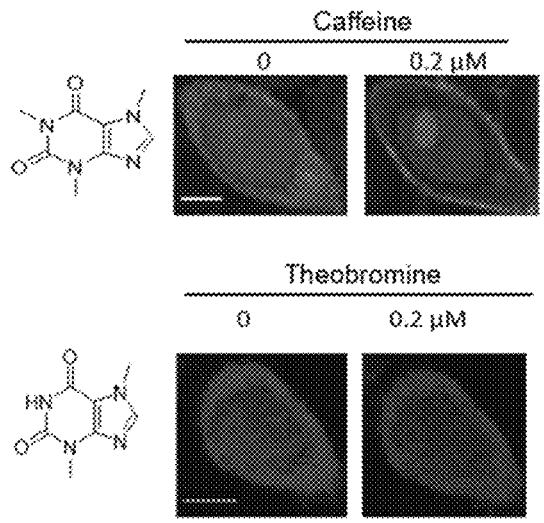
FIG. 6B
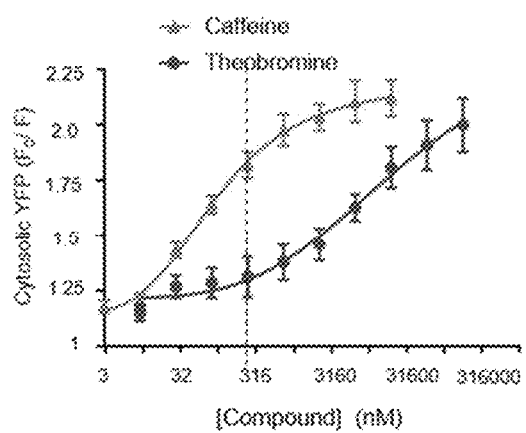
FIG. 6C
Deoxyadenosine  Deoxycytosine  1,8-Naphthalimide
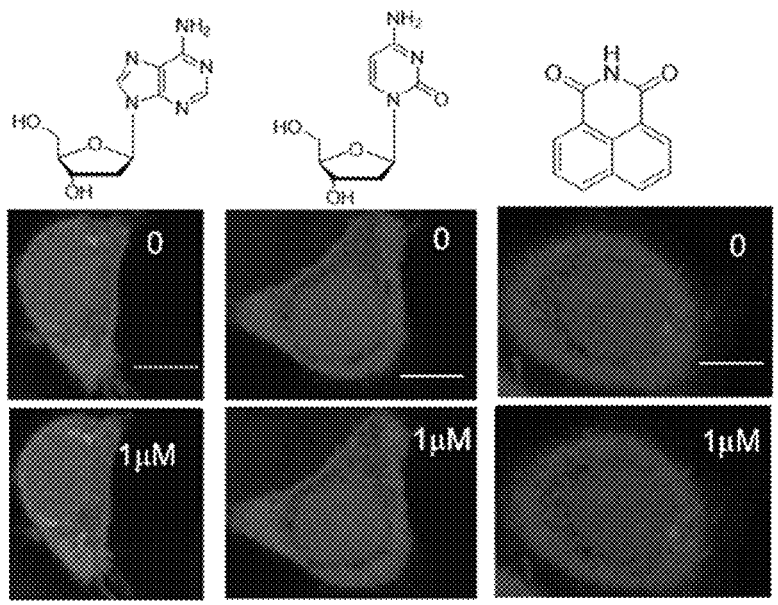
FIGS. 6A-6C FIG. 8A
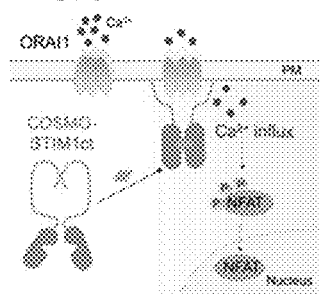
FIG. 8B
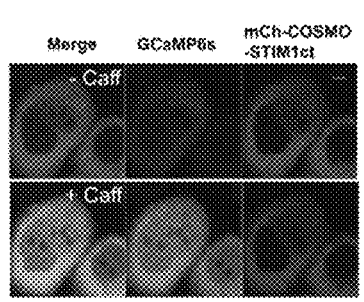
FIG. 8C
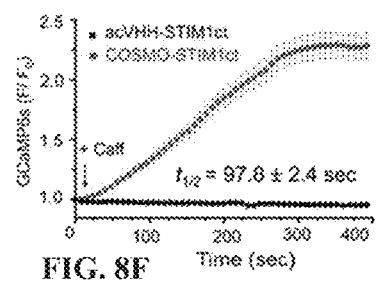
FIG. 8D
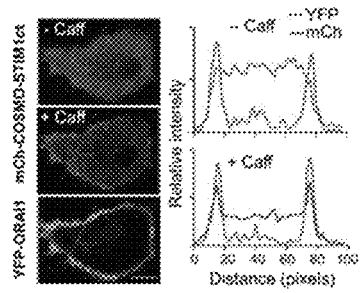
FIG. 8E
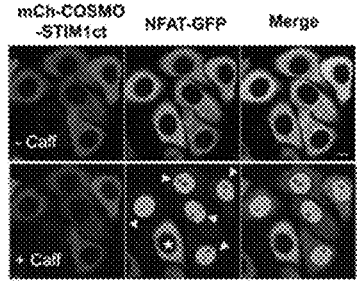
FIG. 8F
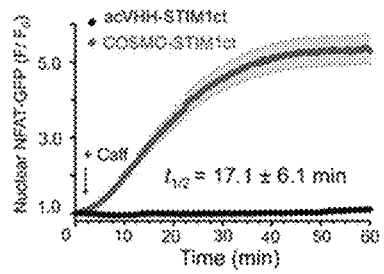
FIGS. 8A-8F FIG. 9A
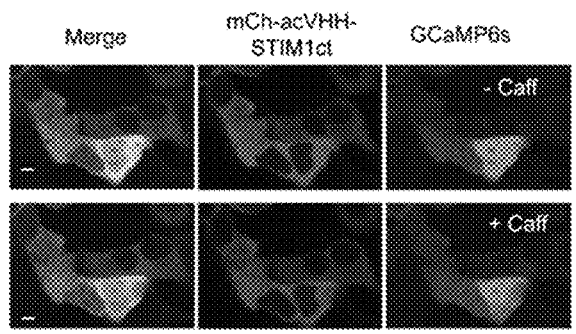
FIG. 9B
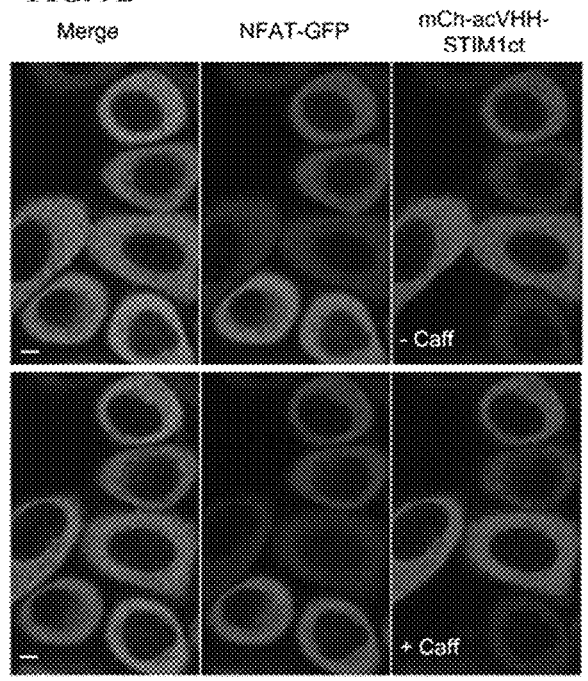
FIGS. 9A-9B FIG. 10A
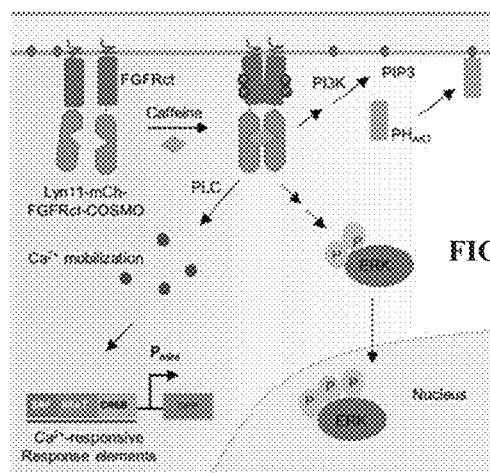
FIG. 10B
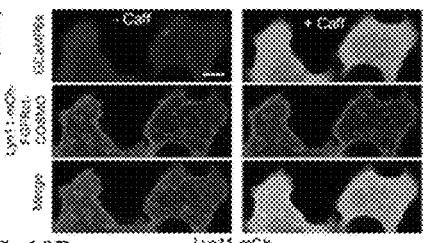
FIG. 10D
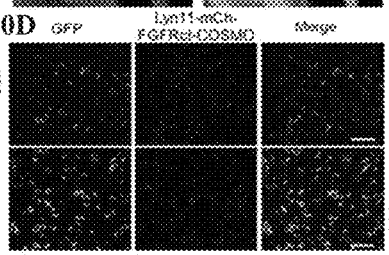
FIG. 10C
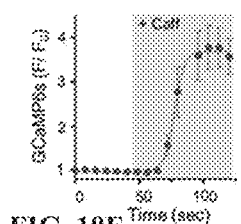
FIG. 10E
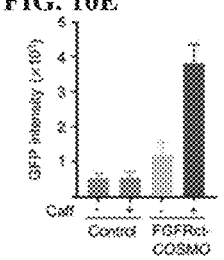
FIG. 10F
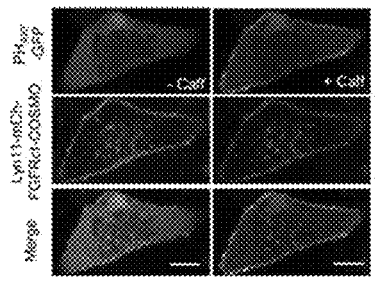
FIG. 10G
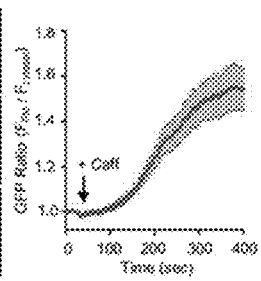
FIG. 10H
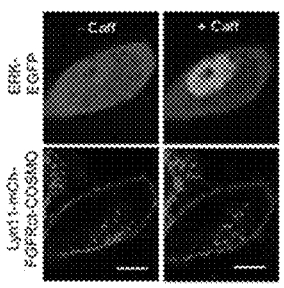
FIG. 10I
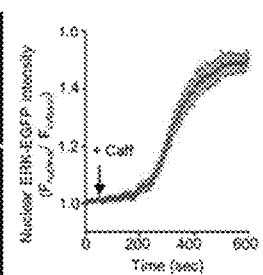
FIGS. 10A-10I

| Linker | Sequence (SEQ. ID NO:) | Structure | PM binding assay YFP-VHH-linker-VHH-PB VHH(WT) PM binding C3T + C3T | | EC50 (nM) | VHH(Y104W) PM binding C3T + C3T | | EC50 (nM) | Binding models |
|---|---|---|---|---|---|---|---|---|---|
| 1 | GAP | flexible | -- | +++ | 107 | + | ++++ | NO | Intermolecular dimerization |
| 2 | DIGAP (8) | flexible | -- | +++ | 375 | + | ++++ | NO | |
| 3 | DIGSGAP (9) | flexible | -- | +++ | 61 | + | ++++ | NO | |
| 4 | DIGGSGGAP (10) | flexible | -- | +++ | 194 | + | ++++ | NO | |
| 5 | LHRAEQSLH DLGAP (11) | rigid | -- | +++ | 530 | -- | ++++ | 16.9 | |
| 6 | HAAAGAPVP YPDPLEPRE QKLISEEDL GGSGGAP (12) | rigid and flexible | -- | -- | ND | -- | -- | ND | Intramolecular dimerization |

Linker 5: selected sequence from STIM1_{L251-L281} (red region)

STIM1-CC1: LKMDLEGLHRAEQSLHDLQERLHKAQEE (PDB: 4O9B)

 (SEQ. ID NO: 13)

Linker 6: the predicated structure by TASSER

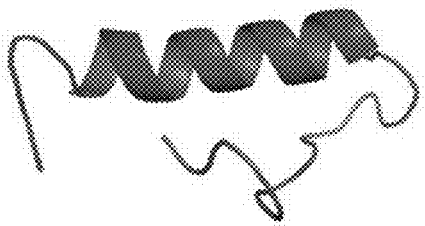

FIG. 14

FIG. 15A
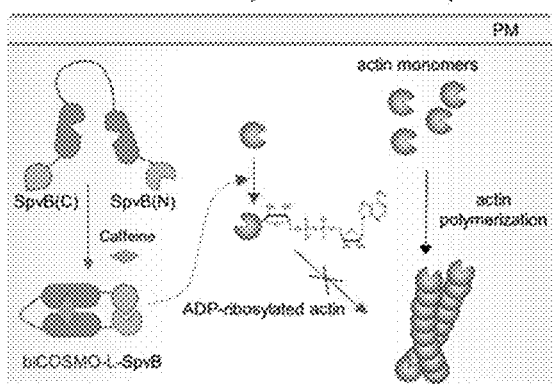
FIG. 15B
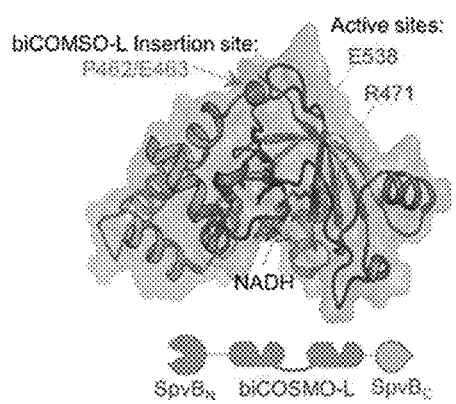
FIG. 15C
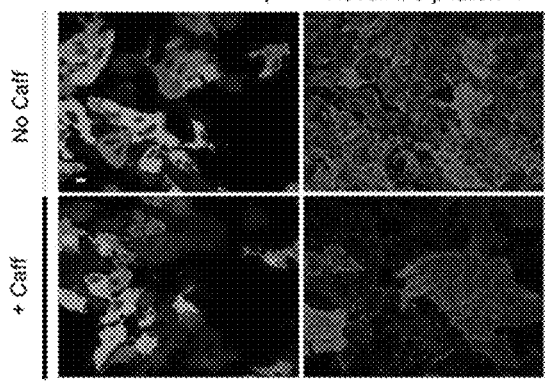
FIG. 15D
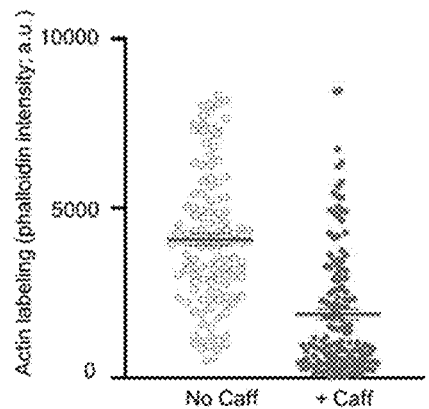
FIGS. 15A-15D

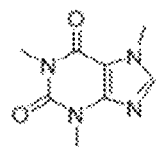
Caffeine
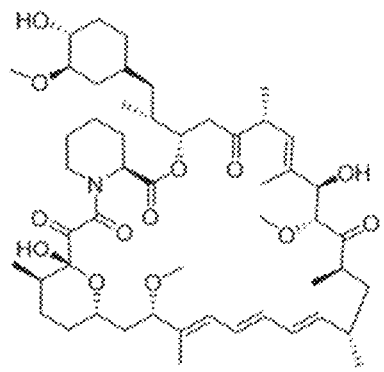
Rapamycin
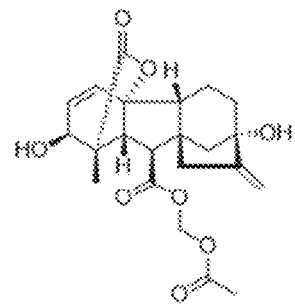
GA$_3$-AM
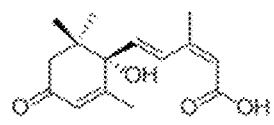
abscisic acid (ABA)
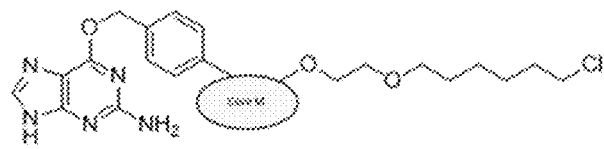
HaXS
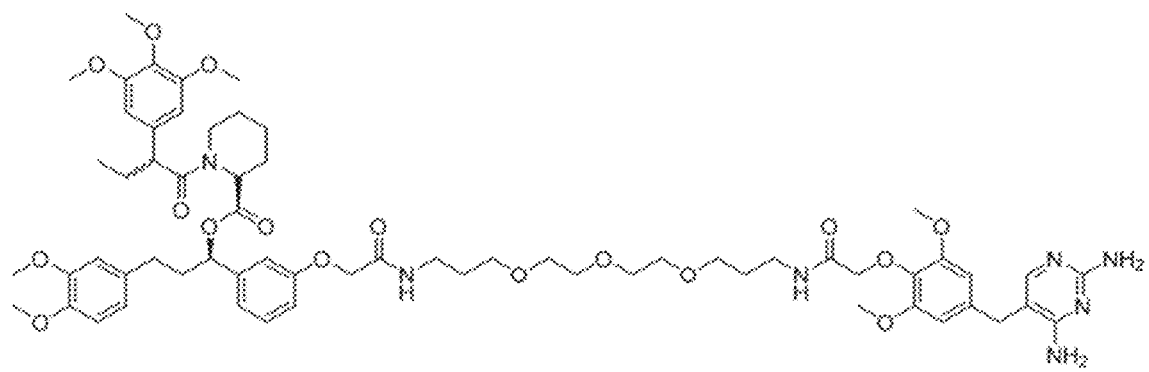
SLF'-TMP
FIG. 16

FIG. 17C
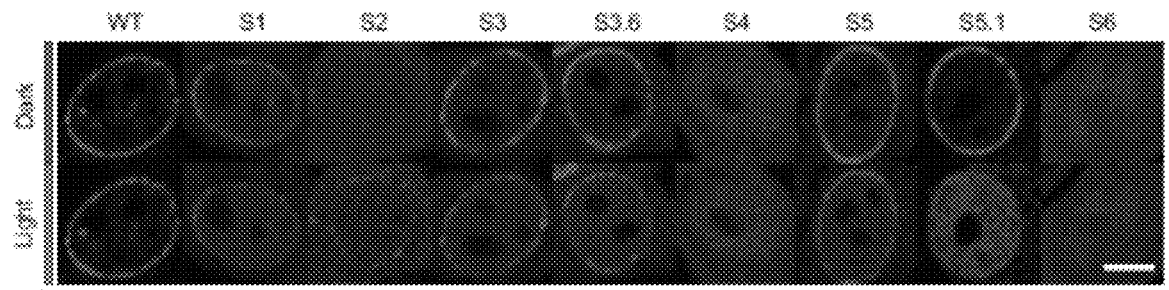
FIG. 17D
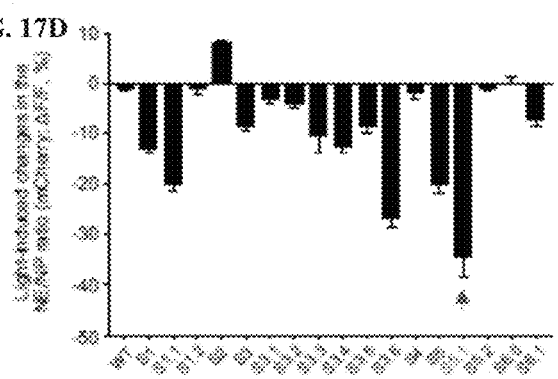
FIG. 17E
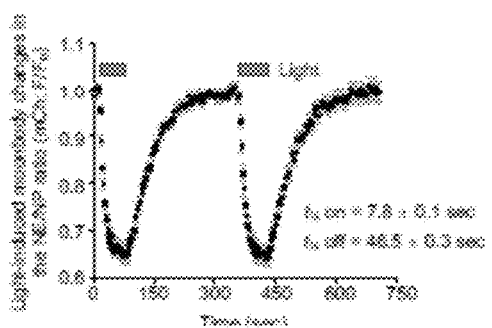
FIGS. 17C-17E

FIG. 18A
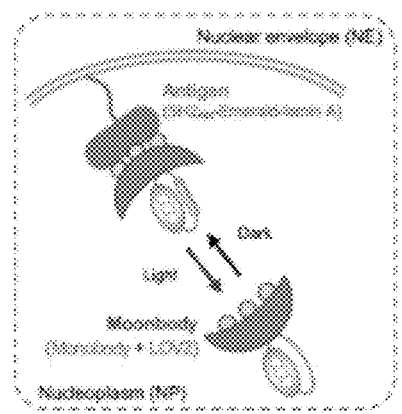
FIG. 18B
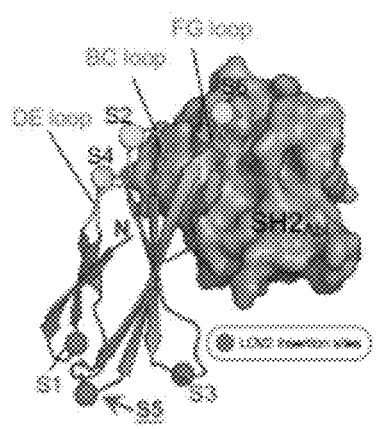
FIG. 18C
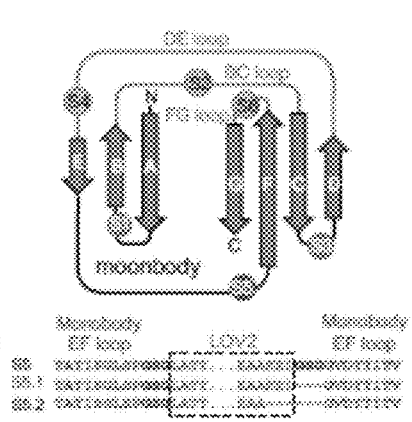
FIGS. 18A-18C

FIG. 18D
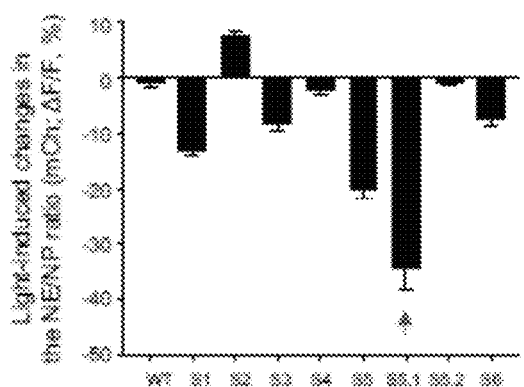
FIG. 18E
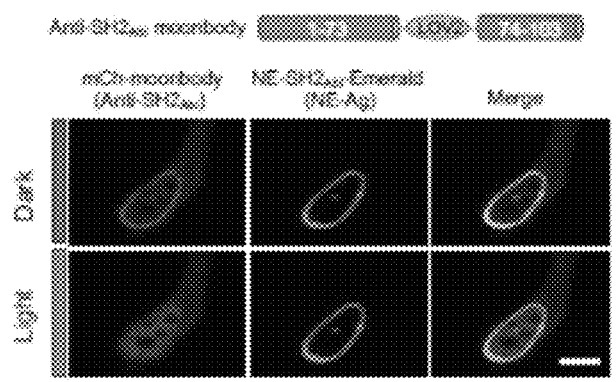
FIGS. 18D-18E

FIG. 18F
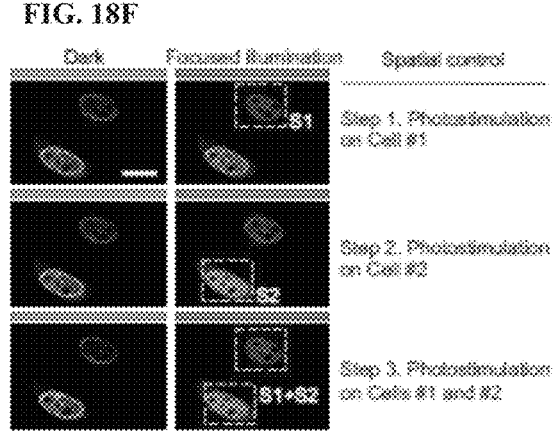
FIG. 18G
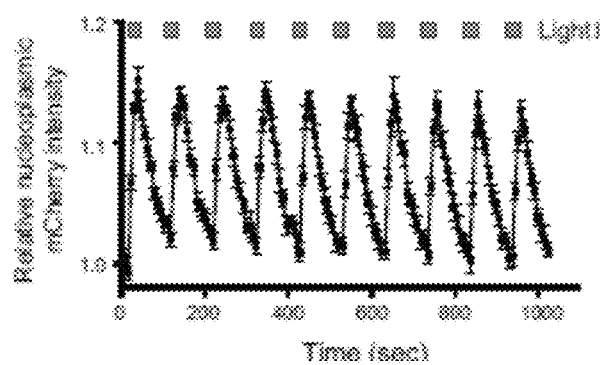
FIGS. 18F-18G

FIG. 18H
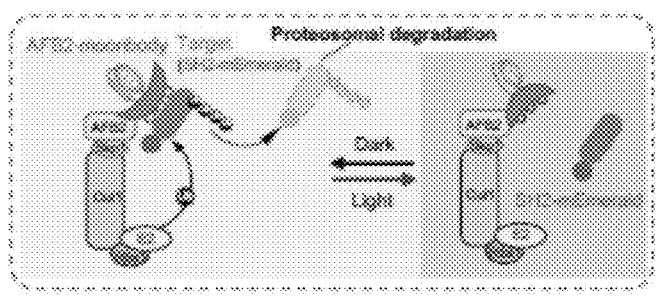
FIG. 18I
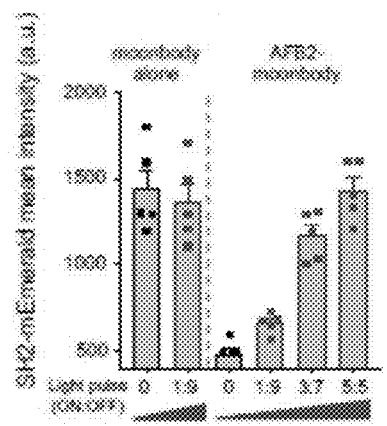
FIGS. 18H-18I

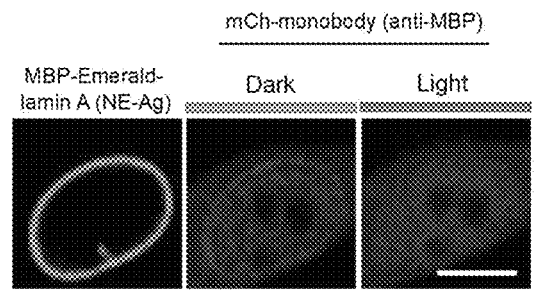
FIG. 19A
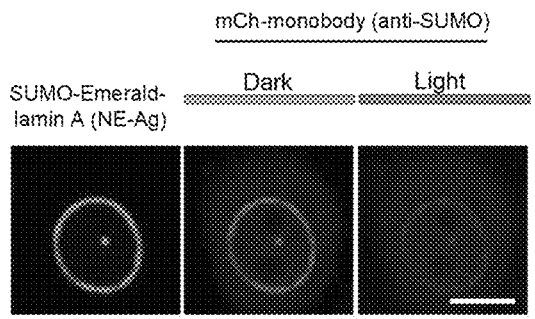
FIG. 19B
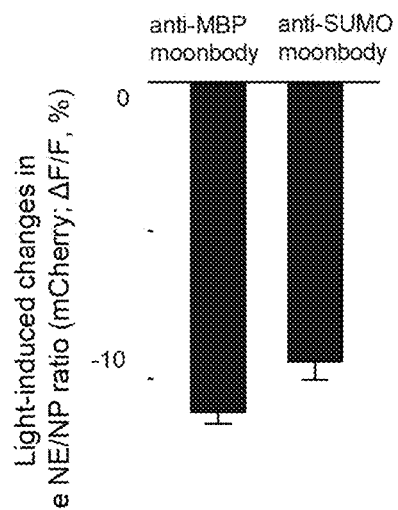
FIG. 19C
FIGS. 19A-19C

FIG. 20A
FIG. 20B
FIG. 20C
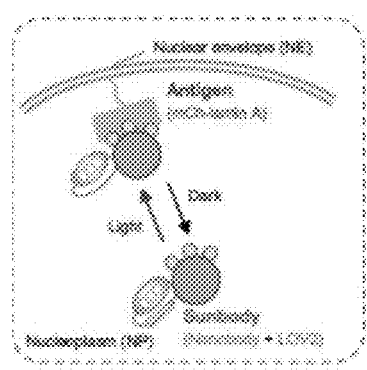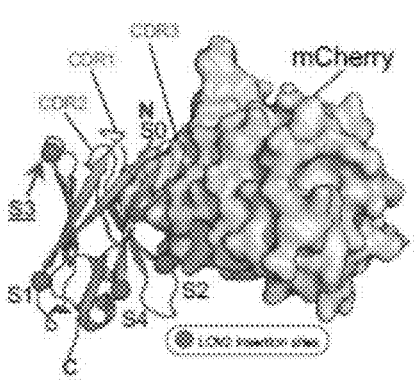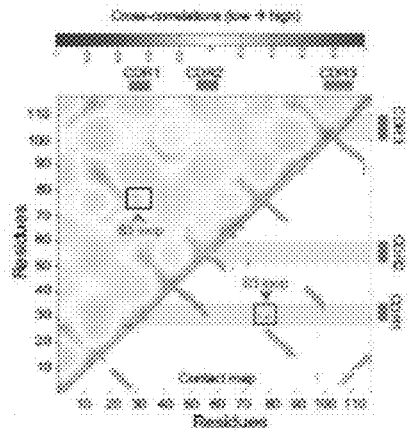
FIGS. 20A-20C

FIG. 20H
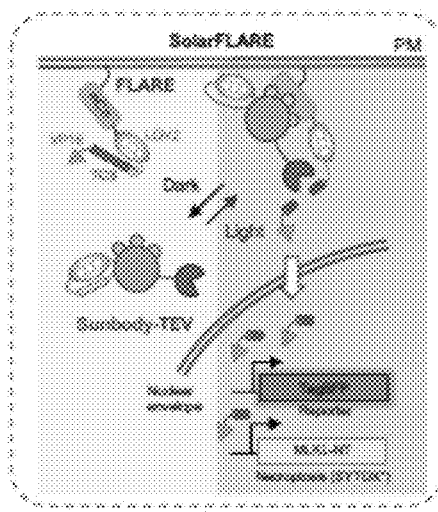
FIG. 20I
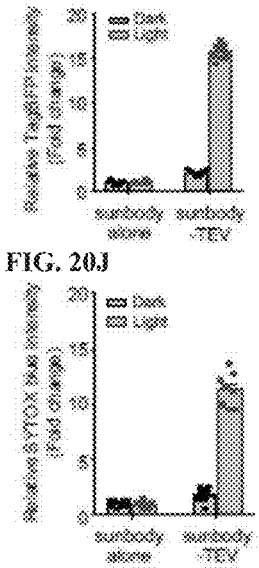
FIG. 20J
FIG. 20K
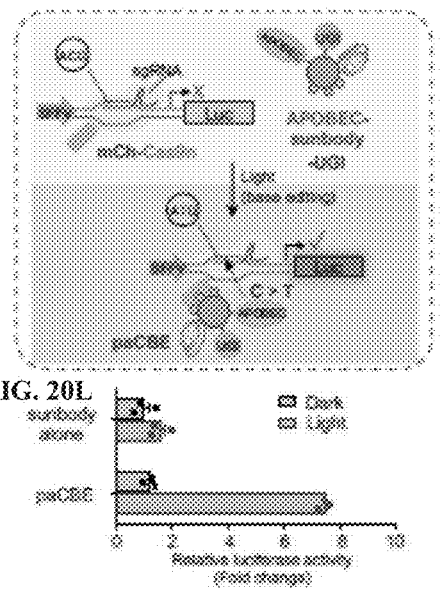
FIG. 20L
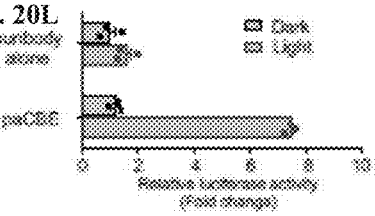
FIGS. 20H-20L

| Sunbody variants | Target binding (dark) | Light-induced change |
|---|---|---|
| WT | Strong | - |
| S0 | Strong | ++ |
| S1 | Weak | - |
| S2 | Strong | - |
| S3 | Weak | +++ |
| S0 +S3 | No binding | +++++ |
| S0 + S3.1 | Weak | ++++ |
| S4 | No binding | - |

FIG. 23A
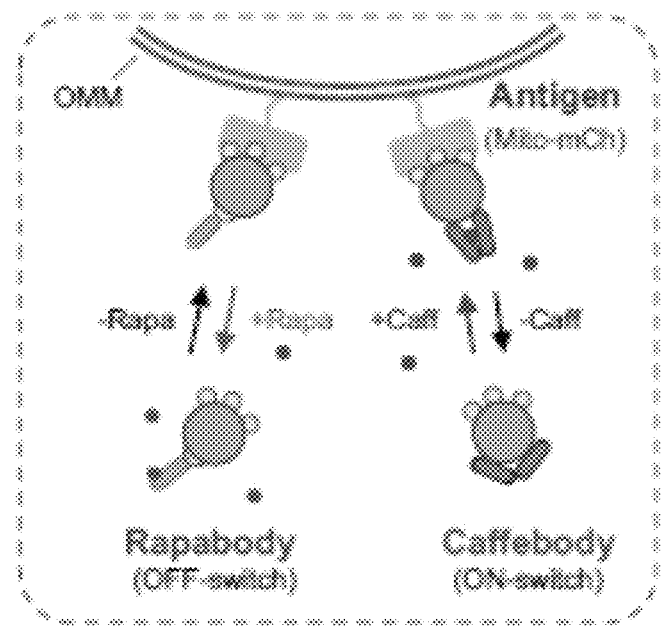
FIG. 23B
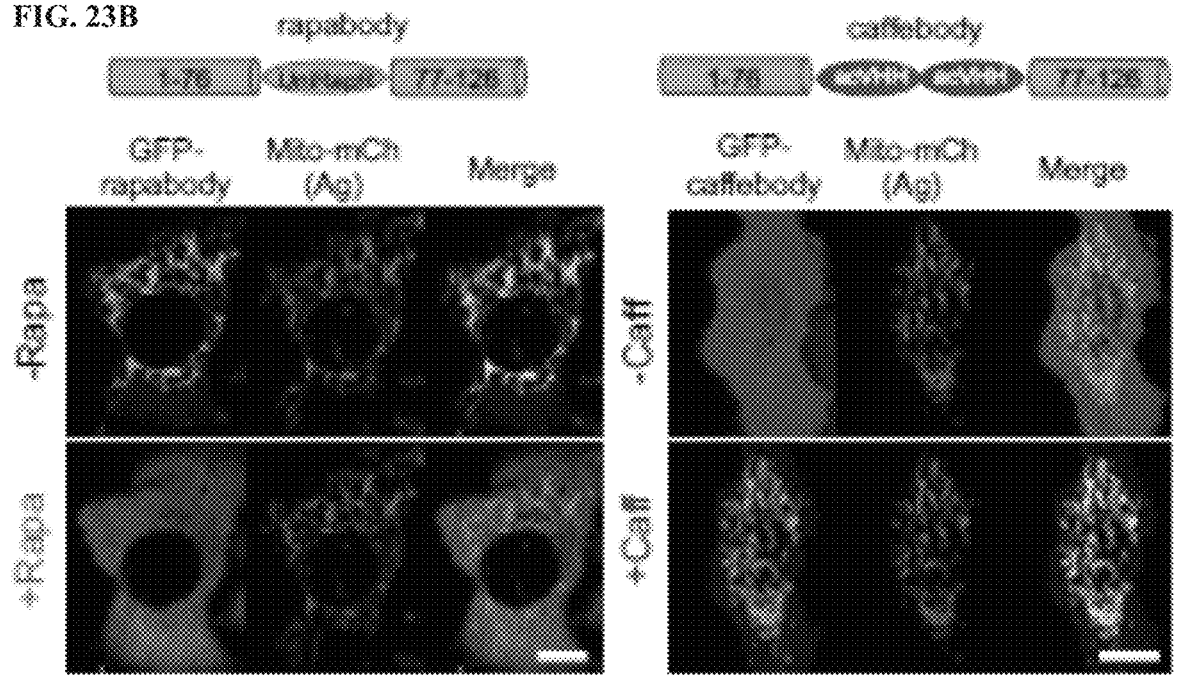
FIGS. 23A-23B

FIG. 23C
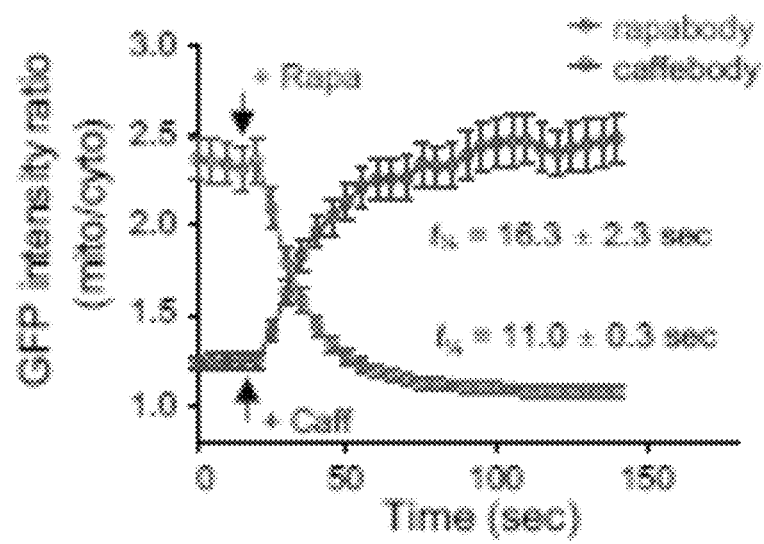
FIG. 23D
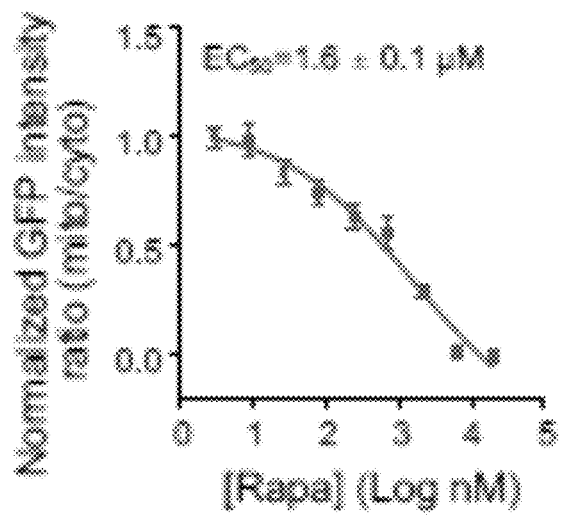
FIGS. 23C-23D

FIG. 23F
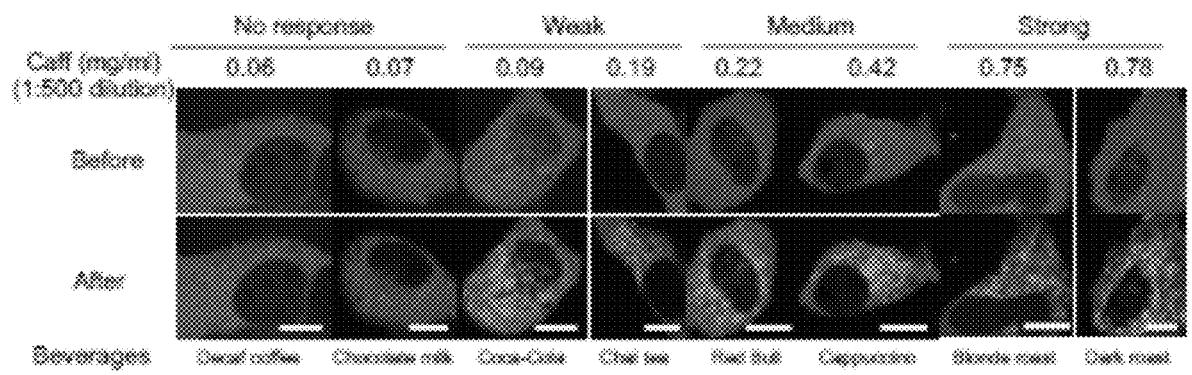
FIG. 23G
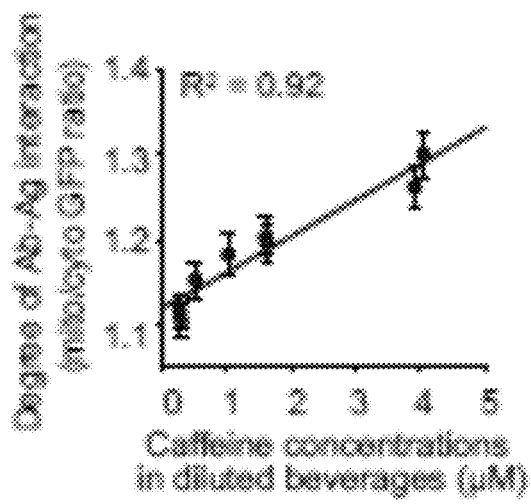
FIGS. 23F-23G

FIG. 23I
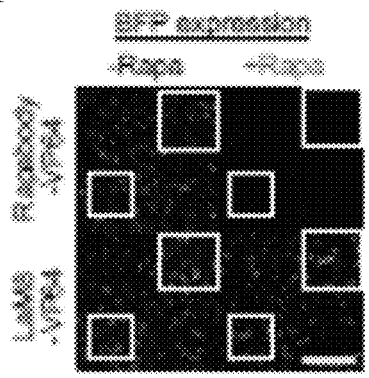
FIG. 23J
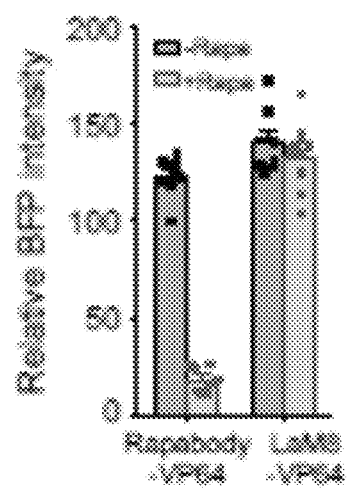
FIGS. 23I-23J

FIG. 23L
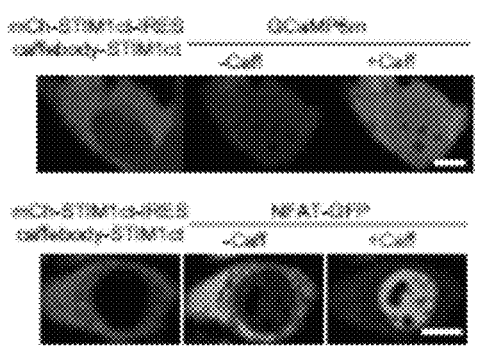
FIG. 23M
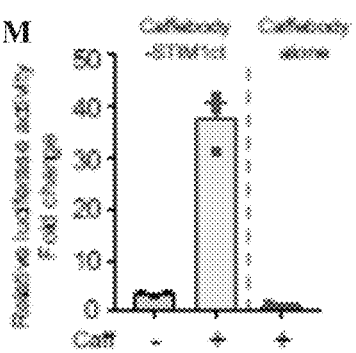
FIGS. 23L-23M

FIG. 24A
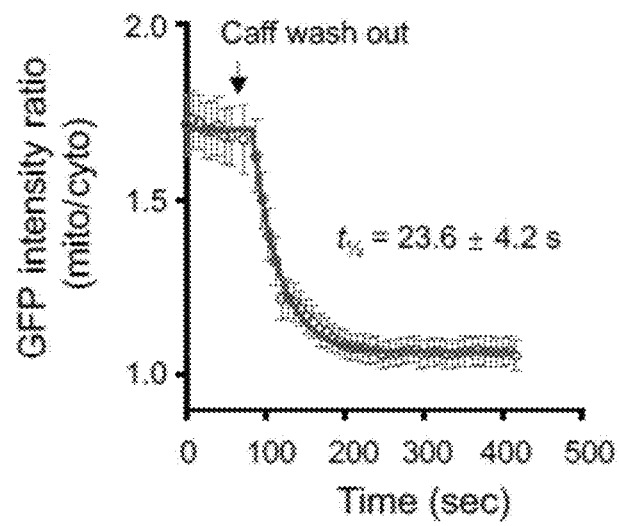
FIG. 24B
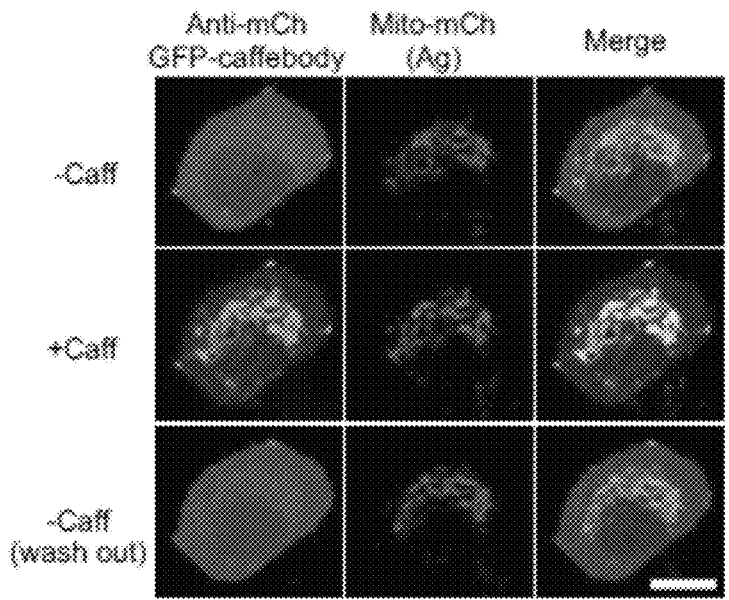
FIGS. 24A-24B

SMART SINGLE-DOMAIN INTRABODIES WITH PRECISION SWITCHES FOR BIOMEDICAL APPLICATIONS

CROSS-REFERENCE TO RELATED APPLICATIONS

This application claims the benefit under 35 USC § 119(e) of U.S. Provisional Application Ser. No. 63/109,377, filed on Nov. 4, 2020, the entire disclosure of which is incorporated herein by reference.

TECHNICAL FIELD

The invention relates to intrabody compositions comprising i) an intrabody and ii) one or more inserts. The invention includes compositions and methods for activating and deactivating intracellular and extracellular interactions utilizing the compositions.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 23 kilobytes ASCII (text) file named "348952_ST25_Revised," created on Apr. 3, 2024.

BACKGROUND AND SUMMARY OF THE INVENTION

Intracellular single-domain antibodies (intrabodies) and their mimetics derived from synthetic protein scaffolds, for instance nanobodies and monobodies are utilized in cell biology, structural biology, synthetic immunology, and theranostics. Intrabodies and their mimetics rival conventional antibodies by their substantially smaller sizes (12-15 kDa vs 150-160 kDa) and ease of in vitro production and in cellulo expression.

Recent engineering efforts have led to the generation of three classes of chemically or light-dependent nanobodies, either based on split nanobodies or hybrid proteins that utilize a photosensitive switch or circularly permuted bacterial dihydrofolate reductase (cpDHFR). However, current nanobodies suffer from slow activation kinetics and are not readily reversible in many biological applications.

Therefore, there exists a need for new compositions and methods utilizing light- and chemically-controllable intrabodies. Accordingly, the present disclosure provides novel intrabody compositions and methods of using the intrabody compositions which exhibit desirable properties and provide related improvements over known compositions.

The present disclosure provides intrabody compositions comprising i) an intrabody and ii) one or more inserts. The disclosure also provides methods of inducing an interaction between proteins as well as methods of activating/deactivating an intrabody composition with light and/or with a chemical.

The intrabody compositions and methods according to the present disclosure provide several benefits. First, the intrabody compositions can be adapted to be reversible, i.e. turning the "switch" off and on. Second, the intrabody compositions possess a more rapid activation/deactivation compared to other compositions in the art. For instance, the intrabody compositions of the present disclosure can possess an on/off half-life of a few seconds compared to the minutes-long half-life of the prior art compositions. Third, the intrabody compositions can provide a marked increase in the dynamic range compared to the prior art compositions. Fourth, the intrabody compositions can be adapted to be activated/deactivated using light and/or using chemicals, for instance chemicals such as caffeine that are readily available. Fifth, the intrabody compositions can provide versatile precision switches to achieve a tailored function when they are inserted into host proteins.

BRIEF DESCRIPTION OF THE DRAWINGS

FIGS. 2A-2H show Design of a cytosol-to-PM-translocation assay to screen COSMO in live cells. FIG. 2A: Schematic depicting a cytosol-to-plasma membrane (PM) translocation assay. FIG. 2B: High-content confocal imaging to monitor caffeine-inducible translocation of YFP-acVHH-PB from the cytosol to PM in HeLa cells. The STIM1-PB sequence information and domain organization of the construct were shown on the top. FIG. 2C: Quantification of the changes in cytosolic YFP-acVHH-PB signals in response to caffeine addition and withdrawal from the culture media. FIG. 2D: The 3D structure of acVHH dimers in complex with caffeine (PDB entry: 6QTL). Key residues nearby the caffeine binding pocket and at the dimer interface were indicated. FIG. 2E: Confocal images showing the distribution of YFP-acVHH-PB variants before and after caffeine treatment in HeLa cells. FIG. 2F: Quantification of the PM/cytosol ratio of YFP signals upon addition of 0, 0.2 and 1 μM caffeine to HeLa cells transfected with the indicated constructs. FIG. 2G: Dose responses curves for the indicated acVHH-PB variants upon titration with caffeine. FIG. 2H: Dose-dependent responses of the indicated variants following treatment with three major caffeine metabolites. Data were shown as mean±sd. Scale bar, 5 μm. n=16 cells from three independent assays.

FIGS. 3A-3C show optimization of acVHH variants for chemogenetic control. Scale bar, 5 μm. FIG. 3A: 3D cartoon representation of the caffeine binding pocket within WT acVHH (PDB entry: 6QT1) and the modeled acVHH-Y104W mutant (COSMO). acVHH dimers were shown in wheat (A) and cyan (B), respectively. Top, Two Y104 residues from the dimeric acVHH sit above caffeine and form hydrogen bonds with H2O (red). Caffeine (yellow sticks) is sandwiched between two Y34 residues (shown as lines). Bottom, two neighboring W104 residues situate above caffeine and form two putative OH··ϕ H-bonds. FIG. 3B: Confocal images showing the subcellular distribution of YFP-acVHH-PB variants (Y104F, Y34W, Y34F, Y61W, M63L, W111Y) before and after caffeine treatment (0.2 and 1 μM) in HeLa cells. FIG. 3C: Time lapse confocal imaging of YFP-acVHH-PB in Hela cells titrated with increasing amounts of caffeine (indicated above each image).

FIGS. 4A-4E show genetically encoded PB-tag for real time dissection of protein assembly in living Cells. Scale bar, 10 μm. FIG. 4A: Schematic illustrating the design of a modified STIM1 PB domain ($STIM1_{666-685}$; PL>KK mutations) used to probe protein oligomeric states in living cells. A positive correlation between the PM-binding degree of PB domain and the oligomeric state of the fusion partner is anticipated. FIG. 4B: Confocal images of HeLa cells expressing mCherry (mCh)-PB (as monomer) or the indicated oligomeric proteins (GST as dimer and DsRed as tetramer) fused with the PB tag. The 3D structures of mCherry, GST and DsRed were shown on the top. FIG. 4C: Quantification of the PM-to-cytosol ($F_{PM}/F_{cytosol}$) fluorescence intensities in HeLa cells expressing monomeric or oligomeric PB domain (as in FIG. 4B). n=25 cells from 3 independent experiments (mean±s.e.m.). FIG. 4D: The PM-to-cytosol ratio of fluorescent signals (in Log 10 scale) plotted against the oligomeric states of indicated proteins (as shown in FIGS. 4C-D). A positive correlation was noted between the two variables ($R^2$=0.97). The in-cellulo oligomeric state of WT acVHH-PB or COSMO(Y104W)-PB was determined to be comparable with a dimer. FIG. 4E: Rapamycin (Rapa)-inducible FRB/FKBP oligomerization reported by the PB-tag. Left, schematic showing the use of rapamycin to induce FKBP-FRB dimerization (top) or FRB-FKBP tetramerization (bottom). Middle, The representative confocal images of transfected HeLa cells before and after treatment with 1 μM rapamycin. Right, Quantification of the PM-to-cytosol ratio of fluorescent signals from the corresponding images. n=16 cells from three independent experiments. Data were shown as mean±s.e.m.

FIGS. 6A-6C show evaluation of the substrate specificity of COMSO. Scale bar, 10 μm. FIG. 6A: Confocal images showing the subcellular distribution of YFP-COSMO-PB in Hela cells, before and after treatment with caffeine or its major metabolite, theobromine. FIG. 6B: Dose responses curves for COSMO upon titration with caffeine or theobromine. FIG. 6C: Confocal images showing the subcellular distribution of YFP-COSMO-PB before and after treatment with caffeine analogues (1 μM).

FIG. 7B=Red Bull; FIG. 7C=coffee). The dilution factors are indicated above the images. Scale bar, 10 μm.

FIGS. 8A-8F show chemogenetic control of Ca2+ entry and nuclear translocation of NFAT in Hela cells using the COSMO system. FIG. 8A: Schematic illustrating the design of caffeine-gated Ca2+ channels. FIG. 8B: Monitoring Ca2+ influx by GCaMP6s fluorescence (green) in HeLa cells co-expressing mCh-COSMO-STIM1ct (red) before and after 1 μM caffeine treatment. FIG. 8C: Quantification of cytosolic Ca2+ changes following addition of 1 μM caffeine in HeLa cells co-expressing the indicated constructs. n=40-60 cells from three independent assays. FIG. 8D: Confocal images showing the localization of mCherry-COSMO-STIM1ct before and after caffeine treatment. HeLa cells were co-transfected with YFP-ORAI1. The graphs on the right showing the quantification of mCh and YFP signals across the dashed line. FIG. 8E: Confocal images of HeLa cells co-expressing NFAT-GFP and mCh-COSMO-STIM1ct before and after 1 μM caffeine treatment. Arrowheads, mCh-positive cells with NFAT nuclear entry; asterisk: mCh-negative cells showing no nuclear translocation of NFAT-GFP. FIG. 8F: Quantification of nuclear accumulation of NFAT-GFP following addition of 1 μM caffeine in HeLa cells expressing the indicated hybrid constructs. Data were shown as mean±sd. Scale bar, 5 μm. n=40-60 cells from three independent assays FIGS. 9A-9B show that acVHH-STIM1ct failed to elicit Ca2+ influx and NFAT nuclear entry following caffeine addition. FIG. 9A: Confocal images of HeLa cells co-transfected with a green Ca2+ sensor (GCaMP6s) and mCh-acVHH-STIM1ct (red) before and after 1 μM caffeine treatment for 10 min. Scale bar, 10 μm. FIG. 9B: Confocal images of HeLa-NFAT-GFP stable cells (green) transfected with mCh-acVHH-STIMIct (red) before and after 1 μM caffeine treatment for 1 hour. The quantifications of Ca2+ influx and NFAT nuclear translocation were shown in FIGS. 8A and 8F. Scale bar, 10 μm.

FIGS. 10A-10I show caffeine-inducible activation of FGFR-mediated cell signaling with the COSMO system. Data are shown as mean±sem. FIG. 10A: Schematic illustrating caffeine-inducible activation of the PM-anchored cytoplasmic region of FGFR (FGFRct) and ist downstream effectors. FIG. 10B: Monitoring intracellular Ca2+ mobilization arising from PLCγ activation by GCaMP6s (green) in HeLa cells co-expressing Lyn11-mCh-FGFRct-COSMO (red) before and after 1 μM caffeine treatment. Scale bar, 10 μm. FIG. 10C: Quantification of cytosolic Ca2+ mobilization by GCaMP6s signals shown in FIG. 10B. n=16 cells from three independent assays. FIG. 10D: Representative confocal images showing the GFP reporter expression before and after 1 μM caffeine treatment. HEK293T cells were co-transfected with Lyn11-mCh-FGFRct-COSMO and GFP-reporter, the expression of which is driven by synthetic Ca2+-responsive transcriptional response elements derived from serum response factor (SRF), nuclear factor of activated-T cells (NFAT), and the cAMP response element-binding protein (CREB). Scale bar, 100 μm. FIG. 10E: Quantification of GFP reporter expression shown in FIG. 10D. Cells only transfected with the reporter cassette were used as control. n=150 cells from three independent assays. FIG. 10F: Fluorescence images of HeLa cells expressing Lyn11-mCh-FGFRct-COSMO and PHAKT-GFP before and after treatment with caffeine. FIG. 10G: Time course showing changes in PHAKT-GFP during the cytosol to PM translocation following caffeine-induced activation of FGFRct. n=16 cells from three independent assays. FIG. 10H: Fluorescence images of HeLa cells expressing Lyn11-mCh-FGFRct-COSMO and ERK-GFP before and after caffeine treatment. Scale bar, 10 μm. FIG. 10I: Quantification of nuclear translocation of ERK-GFP following addition of 1 μM caffeine. n=16 cells from three independent assays FIGS. 11A-11C show use of COSMO to enhance the binding of nanobodies against the RBD domain from the SARS-COV-2 spike protein. FIG. 11A: Schematic illustration of caffeine-inducible COSMO dimerization to form a noncavelently-connected bivalent nanobody, thereby mimicking the role of Fc homodimerization module and enhancing its antigen recognition capability to enage the viral target. FIGS. 11B-11C show ELISA assessment of the reactivity of two COSMO-tagged anti-RBD nanobodies, H11-D4 (FIG. 11B) and VHH72 (FIG. 11C), against SARS-COV-2 RBD. Maltose binding protein (MBP) was used as a control. Datapoints represent the mean of three replicates and data were shown as mean±sem

FIGS. 13A-13G show biCOSMO-S as a potent chemical dimerizer to control necroptosis of HeLa cervical cancer cells. Scale bar, 5 µm. FIG. 13A: Schematic illustration of two possible caffeine-induced effects on a dimeric COSMO concatemer (biCOSMO). The N- and C-termini of two consecutive COSMO proteins are separated by a distance of ~45 Å. A short linker (biCOSMO-S) with an estimated length of less than 45 Å favors inter-molecular dimerization over intramolecular dimerization. This short rigid linker is derived from the initial segment of the coiled-coil region 1 (CC1) of STIM1. FIG. 13B: Confocal images showing the subcellular localization of the indicated YFP-biCOSMO-PB constructs (green) in HeLa cells before and after 1 µM caffeine treatment. FIG. 13C: Quantification of the PM/cytosol ratio of YFP signals upon addition of 0, 0.2 and 1 µM caffeine to HeLa cells transfected with the indicated biCOSMO variants. The linker sequences were shown above the bar graphs. Data were shown as mean±sd. n=16 cells from three independent assays. FIG. 13D: Dose response curves for the indicated biCOSMO-PB constructs. Data were shown as mean±sd. n=16 cells from three independent assays. FIG. 13E: Design of a synthetic cancer cell suicide device using biCOSMO-S. FIG. 13F: Time-lapsed imaging of HeLa cells expressing MLKL$_{NT}$-mCh-biCOSMO-S(red) upon addition of 1 µM caffeine. Annexin V conjugated with Pacific Blue (blue) was used to stain dead cells. DIC, differential interference contrast. FIG. 13G: The time course of caffeine-induced necroptotic cell death reported by cell surface staining with Annexin V. Data were shown as mean±sem. n=10 cells from three independent assays. The second phase of intensity decline after 50 min was due to PM rupture and cell death.

FIG. 14 shows linker optimization for biCOSMO-S/L. The top table showed the rationally designed linkers and their performance after caffeine treatment. The bottom panel showed the crystal structure of Linker 5 (PDB: 4O9B) and the predicated structure of Linker 6 (I-TASSER PMID: 25549265). Each of SEQ ID NO:8, SEQ ID NO:9, SEQ ID NO:10, SEQ ID NO:11, SEQ ID NO: 12, and SEQ ID NO: 13 are shown in FIG. 14.

FIGS. 15A-15D show design of a caffeine-switchable, genetically-encoded inhibitor of actin cytoskeleton assembly based on biCOSMO-L. FIG. 15A: Schematic illustration of caffeine-inducible actin cytoskeleton disassembly. biCOSMO-L is inserted between SpvB (N) (aa 375-462) and SpvB (C) (aa 463-591). FIG. 15B: The 3D structure of an ADP-ribosyltransferase (ATR) domain derived from *Salmonella* SpvB (PDB entry: 3GWL). The domain architecture of the construct was shown below the cartoon. Green, SpvB_ATR N-domain; Blue, SpvB_ATR C-domain; Magenta, biCOSMO-L insertion site between P461 and E462; red, active sites that catalyze actin ADP ribosylation using NAD+ as substrate. FIG. 15C: Confocal images showing EGFP-biCOSMO-L-SpvB-expressing HeLa cells (green) stained with rhodamine-conjugated phalloidin (red) before and after caffeine treatment. FIG. 15D: Quantification of phalloidin staining results before and after caffeine treatment (as shown in FIG. 15C). n=130-150 cells from three independent assays FIG. 16 shows various chemical structures of ligands used in CID systems.

FIGS. 17A-17E show the design and optimization of moonbody variants. FIG. 17A: A molecular motion model for the anti-SH2 monobody used in the study. The degree of mobility from low to high was indicated by the blue-to-red color code shown at the bottom. FIG. 17B: Sequence information for moonbody variants tested in the study. The monobody-LOV2 junction regions were shown for each construct. FIG. 17C: Representative confocal images of HeLa cells co-expressing the antigen (NE-SH2; not shown) and the indicated mCh-moonbody variants (red) before and after photostimulation at 470 nm for 120 sec. Scale bar, 10 µm. FIG. 17D: Summary of the degrees of dissociation (quantified by the NE/NP ratio of mCh signals) from the target (NE-SH2) for the indicated moonbody variants. Selected data were also presented in FIG. 1d. n=6-25 cells (mean±sem). FIG. 17E: Quantification of reversible changes in the NE/NP ratio. HeLa cells co-expressing the anti-SH2 moonbody and NE-tethered SH2 were subjected to two light-dark cycles of stimulation. n=27 cells (mean±sem).

FIGS. 18A-18I show moonbody design and light-tunable control of protein turnover. Data are shown as mean±sem; photostimulation was applied at 470 nm with a power density of 40 µW/mm2 or using the 488-nm laser with 5% input. Scale bar, 10 µm. FIG. 18A: Schematic depicting the design of light-switchable monobody (designated "moonbody") and the nuclear envelope (NE) translocation assay used for screening. A photoswitch LOV2 is inserted into selected loop regions with high mobility in monobody to enable photo-inducible target recognition in a reversible manner. Light-dependent shuttling of moonbody between NE and the nucleoplasm (quantified as the NE/NP ratio of mCh signals) is monitored. Yellow circles represent the three CDR (complementarity-determining region)-like loop regions that mediate monobody-target recognition. FIG. 18B: LOV2 insertion sites mapped to the 3D structure of an anti-SH2Abl monobody (PDB entry: 3T04). Even-numbered insertion sites were created in the target-recognition loops, whereas odd-numbered sites were located opposite to the antigen-recognizing BC/DE/FG loops. FIG. 18C: 2D topology representation of an anti-SH2 monobody, with the insertion sites indicated by circles. The monobody-LOV2 junction regions for S5 or its variants were shown below the cartoon. See FIGS. 17A-17D for detailed sequence information of all 18 constructs tested in the study. FIG. 18D: Quantification of light-dependent responses (as the NE/NP ratio) of moonbody variants. See FIGS. 17A-17D for representative images. Insertion at Site 5 (S5) led to the highest light-induced change. n=6-25 cells. FIG. 18E: Representative confocal images of a HeLa cell co-expressing an anti-SH2 moonbody (mCh-tagged variant S5.1; red) and NE-tethered SH2 domain of Abl kinase (NE tethered-antigen or abbreviated as NE-Ag; green) in the dark or after light illumination for 10 sec. FIG. 18F: Spatial control of the moonbody-antigen interaction in live cells. HeLa cells were co-transfected with NE-SH2Abl (as the Ag; not shown) and mCh-moonbody (shown in gray). Photostimulation was sequentially applied to Cells 1 and 2 in the same imaging field as indicated by the blue box. FIG. 18G: Temporal control of the moonbody-antigen binding in live cells. The nucleoplasmic mCh intensity (as illustrated in FIG. 18E) in response to 10 repeated dark-light cycles of stimulation was quantified. n=11 cells. FIG. 18H: Schematic illustrating the use of an anti-SH2 moonbody for light-tunable degradation of the target protein in mammalian cells. AFB2 binds the Skp1-Cul1-Rbx1 to form a ubiquitin ligase complex to mediate proteasomal degradation. Light-induced dissociation between the moonbody and its target can be exploited to conditionally control protein degradation. FIG. 18I: Quantification of light-tunable degradation of SH2-mEmerald using moonbody. HEK293 cells were transfected with AFB2-moonbody (or monobody alone as control) and SH2-mEmerald, and then either shielded (Dark) or exposed to 8-h blue light illumination with intensifying pulses (with the ON and OFF durations indicated in the x-axis). An external 470-nm LED light was used as the light source (40 µW/mm2). n=5 fields of view per condition.

FIGS. 19A-19C show characterization of monobodies against SUMO and MBP. FIG. 19A: Confocal images of a HeLa cell co-expressing an anti-MBP moonbody (mCh-tagged; red) and NE-tethered GFP-MBP in the dark or after blue light illumination for 120 sec at 470 nm. Scale bar, 10 µm. FIG. 19B: Confocal images of a HeLa cell co-expressing an anti-SUMO moonbody (mCh-tagged; red) and NE-tethered. GFP-SUMO (green) before (dark) and after blue light illumination for 120 sec at 470 nm. Scale bar, 10 µm. FIG. 19C: Quantification of light-dependent response (as the NE/NP ratio of mCh signals) of the MBP or SUMO-specific moonbodies. n=33-67 cells from three independent assays (mean±sem).

FIGS. 20A-20L show sunbody design and photoactivatable gene transcription and base editing. Data are shown as mean±sem; photostimulation was applied at 470 nm with a power density of 40 µW/mm2 or using the 488-nm laser with 1-5% input. Scale bar, 10 µm. FIG. 20A: Cartoon depiction of the design and the NP-to-NE translocation assay. Photoswitchable redistribution of an engineered anti-mCherry (mCh) nanobody (designated "sunbody") is used as the readout. Sunbody is expected to shuttle between NE and NP in a light-dependent manner. Yellow circles represent three CDRs involved in antigen binding. FIG. 20B: Insertion sites for LOV2 mapped to the modeled 3D structure of an anti-mCh nanobody (LaM8). S1, S2 and S4 are located at the opposite side of CDR loops. Both the N-terminus (S0) and S3 are in close proximity to CDRs. See FIGS. 21A-21D for detailed sequence information. FIG. 20C: The S3 loop region mapped to the cross-correlations (upper left corner) and protein contact maps (lower right corner) of LaM8. FIG. 20D: Quantification of light-induced changes in the NE/NP ratio for an anti-mCh GFP-tagged sunbody. The combination of LOV2 fusion to the N-terminus (S0) and its additional insertion at S3 led to the strongest light-inducible changes (S0+S3). See FIGS. 21A-21D for light-induced changes of each construct. n=15-66 cells from three independent assays. FIG. 20E: Representative confocal images of a HeLa cell co-expressing sunbody (GFP-tagged LaM8-S3; green) and NE-tethered mCh-lamin A (red) before and after light illumination for 10 sec. FIG. 20F: Quantification of the sunbody-antigen interaction in response to three repeated dark-light cycles. The changes in the nucleoplasmic GFP signals were used as the readout. n=23 cells. FIG. 20G: Sunbody used for light-dependent subcellular targeting of its binding partner. HeLa cells were transfected with an anti-mCh GFP-tagged sunbody (1×; green; top panels), or its concatemeric form (2×; green; bottom panels), along with the mCh as antigen (red) tethered to PM (left), ER (middle), or outer mitochondrial membrane (right). The quantification of relative GFP signals at the corresponding subcellular organelles before and after light illumination were shown next to the images (n=15-75 cells). The use of 2×sunbody in a single construct substantially enhanced the signal-to-noise ratio. FIG. 20H: Cartoon illustrating the combination of sunbody with a modified FLARE system (designated SolarFLARE) to enable light-inducible expression of genes of interest, such as TagBFP as a reporter or the N-terminal domain of MLKL (MLKL-NT) as a necroptosis inducer. FIG. 20I: Quantification of BFP expression in Hela cells transfected with SolarFLARE (sunbogy-TEV+FLARE) or the control (sunbody alone+FLARE) vectors, as well as the TagBFP reporter gene, before and after light illumination for 8 h. n=10 fields of view from three independent assays. FIG. 20J: Quantification of necroptotic cell death as indicated by SYTOX blue nuclear staining of dead cells. HeLa cells were transfected with SolarFLARE (sunbogy-TEV+FLARE) or the control (sunbody alone+FLARE) vectors, as well as the inducible MLKL-NT expression cassette, before and after light illumination for 8 h. Also see FIG. 22 for representative images. n=10 fields of view from three independent assays. FIG. 20K: Design of a photoactivatable cytosine base editor (paCBE). Upon photostimulation, sunbody-mCh association re-assembles two functional units of CBE (Part I: the mCh-Cas9n/sgRNA for genome targeting; Part II: APOBEC1-sunbody-UGI for C-to-T conversion) to restore the activity of paCBE. A "Gene ON" (GO) luciferase reporter system is used to report the activity of paCBE before and after light stimulation. Successful recruitment of Part II to the targeted genomic locus is anticipated to cause C-to-T conversion in the start codon (ACG>ATG) to initiate the translation of a luciferase reporter gene. FIG. 20L: Quantification of the base editing efficiency of paCBE by using luciferase activity as readout. Sunbody alone was used as negative control. n=3 independent assays.

FIG. 21A: A molecular motion model for the anti-mCh nanobody used in the study. The degree of mobility from low to high was indicated by the blue-to-red color code shown at the bottom. FIG. 21B: Sequence information of sunbody variants tested in the study. The sunbody-LOV2 junction regions were shown for each construct. FIG. 21C: Representative confocal images of HeLa cells co-expressing the NE-tethered mCherry (as antigen; not shown) and the indicated GFP-sunbody variants (green). Scale bar, 10 µm. FIG. 21D: Summary of the degrees of antigen (mCh) binding for the indicated GFP-sunbody variants before and after light stimulation (see FIG. 21C). −, <5%; +, 5-10%; ++, 10-20%; +++, 20%-40%; ++++, 40%-60%; +++++>60% increase in the NE/NP ratio.

FIGS. 23A-23M show design of drug- or beverage-switchable nanobodies and their applications. Data are presented as mean±sem. FIG. 23A: Schematic illustration of the design and the mitochondria (Mito) translocation assay used to screen drug-switchable nanobodies. UniRapR or two tandem-linked copies of acVHH domains were inserted into the S3 loop of LaM8 (as depicted in FIG. 2b). Rapabody is designed to enable rapamycin (Rapa)-inducible antibody-antigen dissociation (OFF-switch); whereas caffebody enables caffeine-inducible activation of antibody-antigen recognition (ON-switch). FIG. 23B: Representative confocal images of HeLa cells showing the colocalization between the antigen (Mito-mCh; red) and GFP-rapabody (green) or GFP-caffebody (green) before (top panels) and after (bottom panels) treatment with 5 µM rapamycin (left) or caffeine (right). The domain architectures of rapabody and caffebody were shown above the corresponding images.

Scale bar, 10 μm. FIG. 23C: Quantification of chemical inducible changes in the binding between Mito-mCh and anti-mCh rapabody (red) or caffebody (blue). The corresponding half-lives were indicated. n=31 and 35 cells, respectively. FIG. 23D: Dose-response curve of rapabody. The Mito-to-cytosol ratios of GFP-rapabody expressed in HeLa cells (as shown in FIG. 23B, left) were plotted against the increasing amounts of rapamycin (n=17 cells). FIG. 23E: Dose-response curve of caffebody expressed in HeLa cells. The Mito-to-cytosol ratios of GFP-caffebody (as shown in FIG. 23B, right) were plotted against escalating doses of caffeine (n=38 cells). FIG. 23F: Use of caffeinated beverages to activate the caffebody-antigen interaction in mammalian cells. Shown were confocal images of HeLa cells co-expressing an anti-mCh GFP-caffebody (green) and Mito-mCh as antigen (not shown) before and after addition of the indicated beverages (1:500 dilution). The caffeine contents of tested beverages were indicated on the top. Scale bar, 10 μm. FIG. 23G: Quantification of beverage-induced changes in the degrees of caffebody-antigen binding. The Mito/cytosol ratio of GFP signals were plotted against caffeine concentrations in diluted beverages (as shown in FIG. 23F). A positive correlation was noted (R2=0.92; n=40-43 cells). FIG. 23H: Cartoon illustrating the design of a ligand-switchable split CRISPRa system made of dCas9 and VP64. In the absence of rapamycin, anti-mCh rapabody-VP64 interacts with mCh-dCas9 to induce gene expression. Upon rapamycin treatment, rapabody-VP64 dissociates from mCh-dCas9 to terminate transcriptional activation. BFP is used as a reporter for dCas9-VP64-mediated transcriptional regulation. FIG. 23I: Confocal images showing BFP expression in Hela cells transfected with the photo-activatable CRIPSRa system (rapabody-VP64+mCh-dCas9) or the control vectors (LaM8-VP64+mCh-dCas9) before and after overnight rapamycin treatment (5 μM). Scale bar, 500 μm. FIG. 23J: Quantification of BFP signals before and after rapamycin treatment (as shown in FIG. 23I). n=8 fields of view from three independent assays. FIG. 23K: Cartoon depicting the use of caffebody to achieve caffeine-inducible gating of ORAI1 calcium channels. Caffeine switches on the caffebody-mCh interaction to induce hetero-oligomerization of the cytoplasmic domain of STIM1, which overcomes the autoinhibition mediated by CC1-SOAR, and further activate ORAI1 to elicit calcium influx and nuclear translocation of NFAT to turn on gene expression (luciferase as readout). mCh-STIMlct and caffebody-STIMlct were co-expressed using a bicistronic IRES-driven expression vector. CC1, coiled coil 1 region; SOAR, STIM-Orai activating region. FIG. 23L: Confocal images showing caffeine-induced activation of Ca2+ influx (reported by GCaMP6m; top panels) and nuclear translocation of NFAT-GFP (bottom panels) in HeLa cells. Scale bar, 10 μm. FIG. 23M: Quantification of NFAT-dependent luciferase gene expression before and after caffeine treatment. HeLa cells were co-transfected with mCh-STIMIct and caffebody-STIMIct (or caffebody alone as control), and then incubated with 5 μM caffeine. 15 nM PMA was co-added to boost the co-stimulatory signal. n=3 independent assays.

FIGS. 24A-24D show characterization of an anti-mCh, GFP-tagged caffebody upon treatment with caffeine, caffeinated beverages, or an FDA-approved caffeine analog theophylline. FIG. 24A: The caffeine-induced activation of the caffebody-mCh interaction could be switched off upon withdrawal of caffeine. The deactivation half-life was determined to be 23.6±4.2 sec. n=22 cells (mean±sem). FIG. 24B: Representative confocal images demonstrating the reversibility of the caffebody-antigen interaction. HeLa cells were co-transfected with an anti-mCh GFP-tagged caffebody (green) and Mito-mCh (red). Images were taken before (top) and after (middle) caffeine addition, followed by perfusion of caffeine-free medium to the culture dish to wash out residual caffeine (bottom). Scale bar, 10 μm. FIG. 24C: Confocal images of HeLa cells expressing GFP-caffebody (green) and Mito-mCh (not shown) before and after treatment with caffeinated beverages (left) or theophylline (right). The caffeine contents and the dilution factors used in the experiments were indicated above the images. The translocation of GFP-caffebody toward Mit-mCh was used as the readout. Scale bar, 10 μm. FIG. 24D: HeLa cells transfected with mCh-STIM1ct+caffebody alone did not show caffeine-induced changes in GCaMP6 signals. Scale bar, 10 μm.

DETAILED DESCRIPTION

Figure 1:
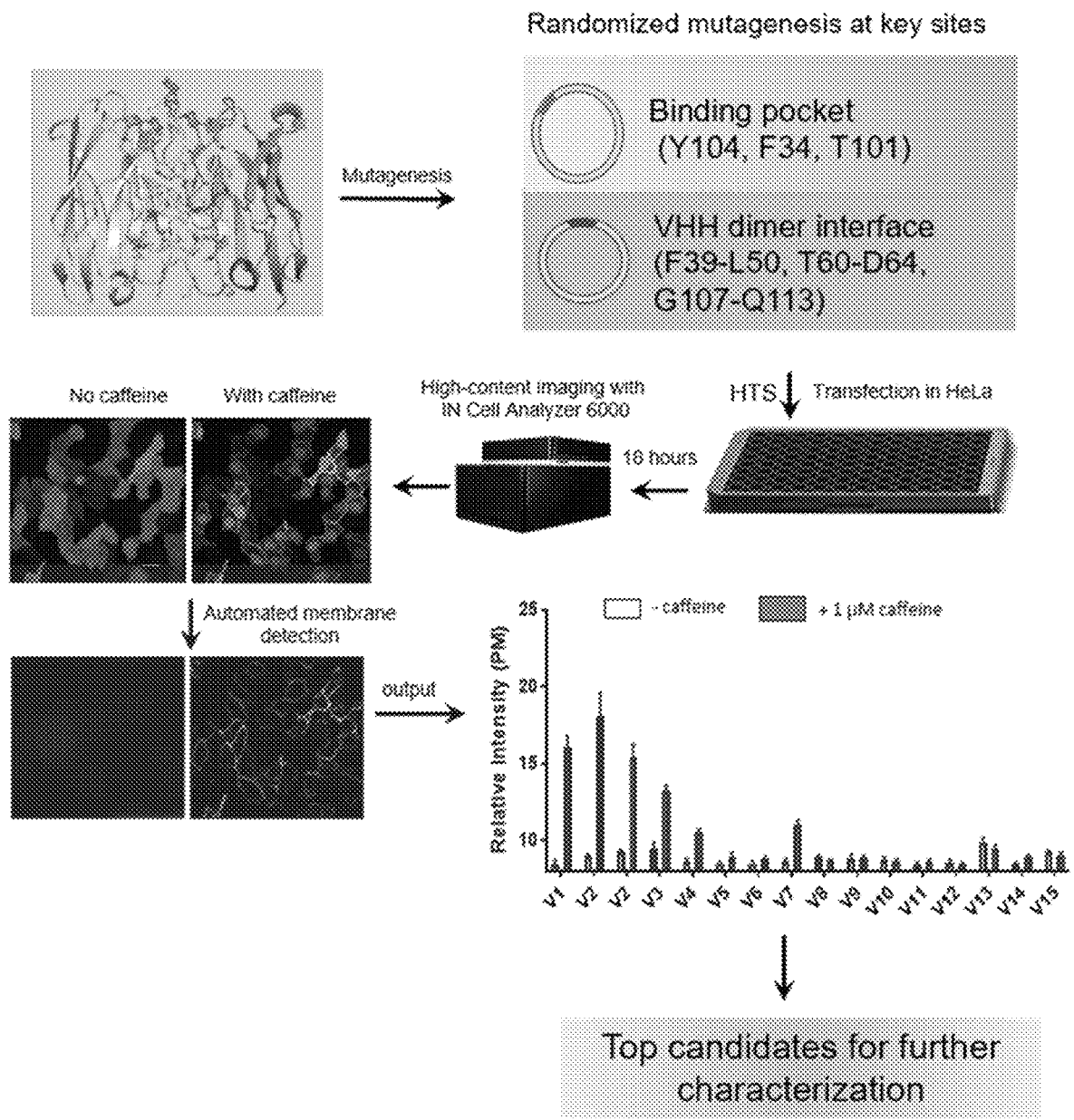
FIG. 1 shows a workflow illustrating the screening process of anti-caffeine single variable domain on a heavy chain (acVHH) variants and optimization of COSMO (abbreviation for caffeine-operated synthetic module). Mutations were first randomly introduced into key positions/interfaces involved in caffeine binding and dimerization (a total of 27 positions). Each variant was tagged with the plasma membrane (PM)-targeting polybasic (PB) domain, thus enabling the use of cytosol-to-PM translocation as a convenient readout for the assay. An automated PM detection pipeline was used to aid in the image analysis. The top candidates emerged from the screen were further characterized via caffeine titration to obtain their $EC_{50}$ values.

In an illustrative aspect, an intrabody composition is provided. The intrabody composition comprises i) an intrabody and ii) one or more inserts process for making a cellulose-based material is provided.

Various intrabody compositions are provided herein. Table 1 describes specific intrabody composition embodiments:

TABLE 1

Specific Intrabody Composition Embodiments

| Intrabody Composition | Intrabody | Insert(s) | Stimulation | SEQ ID NO. |
|---|---|---|---|---|
| "Moonbody" | Monobody | LOV2 | Light | SEQ ID NO: 1 |
| "Sunbody" | Nanobody | LOV2 (two copies) | Light | SEQ ID NO: 2 |
| "Rapabody" | Nanobody | UniRapR | Rapamycin and related metabolites, analogs, and variants | SEQ ID NO: 3 |
| "Caffebody" | Nanobody | acVHH | Caffeine and related metabolites, analogs, and variants | SEQ ID NO: 4 |
| "COSMO" | Nanobody | acVHH variant | Caffeine and related metabolites, | SEQ ID NO: 5 |

TABLE 1-continued

Specific Intrabody Composition Embodiments

| Intrabody Composition | Intrabody | Insert(s) | Stimulation | SEQ ID NO. |
|---|---|---|---|---|
| "biCOSMO-S" | Nanobody | acVHH variants (two copies) connected by short linker | analogs, and variants Caffeine and related metabolites, analogs, and variants | SEQ ID NO: 6 |
| "biCOSMO-L" | Nanobody | acVHH variants (two copies) connected by long linker | Caffeine and related metabolites, analogs, and variants | SEQ ID NO: 7 |

In an embodiment, the intrabody is a monobody. In an embodiment, the intrabody is a nanobody. In an embodiment, the intrabody is a monobody that recognizes the SH2 domain of Abl. In an embodiment, the monobody comprises an EF domain.

In an embodiment, the intrabody is a mCherry-specific nanobody. In an embodiment, the mCherry-specific nanobody comprises an S3 loop.

In an embodiment, the insert is a protein or a protein fragment. In an embodiment, the protein comprises a LOV2 fragment. In an embodiment, the protein comprises a circularly permuted version of cpLOV2. In an embodiment, the protein comprises acVHH. In an embodiment, the protein comprises an acVHH variant. In an embodiment, the protein comprises UniRapR.

In an embodiment, the intrabody composition comprises two inserts. In an embodiment, the two inserts comprise a first insert and a second insert. In an embodiment, the first insert and the second insert are the same. In an embodiment, the first insert and the second insert are different. In an embodiment, the first insert and the second insert both comprise a LOV2 fragment. In an embodiment, the first insert and the second insert both comprise cpLOV2. In an embodiment, the first insert and the second insert both comprise a circularly permuted version of cpLOV2. In an embodiment, the first insert and the second insert both comprise acVHH. In an embodiment, the first insert and the second insert both comprise an acVHH variant.

In an embodiment, the insert comprises two inserts. In an embodiment, the two inserts are contacted via a linker. In an embodiment, the two inserts are covalently connected. In an embodiment, the two inserts are covalently connected via a linker. A linker according to the present disclosure can be long or short in length. Appropriate linkers are well know in the art.

In one embodiment, an intrabody composition comprises a LOV2 fragment (residues 404-546) inserted into the EF loop of a monobody that specifically recognizes the Src Homology 2 (SH2) domain of Abelson tyrosine kinase (Abl).

In one embodiment, an intrabody composition comprises two LOV2 fragments (residues 404-546 or 408-543) inserted into a mCherry-specific nanobody (LaM8) S3 loop to make a LOV2 double controlled chimeric LOV2-LaM8 (N)-LOV2-LaM8(C).

In one embodiment, an intrabody composition comprises a dimeric concatemer of acVHH (bivalent acVHH) fused with an mCherry-specific nanobody (LaM8) S3 loop.

In one embodiment, an intrabody composition comprises UniRapR fused with a mCherry-specific nanobody (LaM8) S3 loop. In some aspects, the UniRapR component can be replaced by an engineered pair of FBP/FKBP called cpRAPID (see Lee et al., Journal of Molecular Biology, 2020, 432(10):3127-3136, incorporated herein in its entirety).

In one embodiment, an intrabody composition comprises an acVHH insert with enhanced affinity inserted into a nanobody. In one embodiment, an intrabody composition comprises two acVHH inserts with enhanced affinity inserted into a nanobody, wherein the two inserts are connected with a short linker. In one embodiment, an intrabody composition comprises two acVHH inserts with enhanced affinity inserted into a nanobody, wherein the two inserts are connected with a longer linker.

In an embodiment, the intrabody composition is conjugated to a therapeutic agent. In an embodiment, the therapeutic agent is a CAR-T cell. In an embodiment, the therapeutic agent is an NK cell. In an embodiment, the therapeutic agent is a macrophage. In an embodiment, the therapeutic agent is an antibody. In an embodiment, the therapeutic agent is an E3 ligase. In an embodiment, the therapeutic agent is a TEV protease. In an embodiment, the therapeutic agent is transcriptional activator VP64.

In an embodiment, the intrabody composition is adapted for activation by light. In an embodiment, the activation by light is reversible. In an embodiment, the intrabody composition is adapted for deactivation by light. In an embodiment, the deactivation by light is reversible. Advantageously, activation and/or deactivation of the described intrabody compositions by light is rapid in nature.

In an embodiment, the intrabody composition is adapted for activation by a chemical. In an embodiment, the activation is reversible. In an embodiment, the chemical is rapamycin. In an embodiment, the chemical is a rapamycin metabolite. In an embodiment, the chemical is a rapamycin analog. In an embodiment, the chemical is caffeine. In an embodiment, the chemical is a caffeine metabolite. In an embodiment, the chemical is a caffeine analog.

In an embodiment, the intrabody composition is adapted for deactivation by a chemical. In an embodiment, the activation is reversible. In an embodiment, the chemical is rapamycin. In an embodiment, the chemical is a rapamycin metabolite. In an embodiment, the chemical is a rapamycin analog. In an embodiment, the chemical is caffeine. In an embodiment, the chemical is a caffeine metabolite. In an embodiment, the chemical is a caffeine analog. Advantageously, activation and/or deactivation of the described intrabody compositions by a chemical is rapid in nature.

In an embodiment, the intrabody composition is configured to induce a protein-protein interaction. In an embodiment, the protein-protein interaction is reversible.

In an embodiment, the protein-protein interaction comprises association of a first protein to a second protein. In an embodiment, the protein-protein interaction comprises disassociation of a first protein to a second protein. In an embodiment, the protein-protein interaction comprises association of a first protein to a second protein. In an embodiment, the protein-protein interaction comprises protein subcellular translocation. In an embodiment, the protein-protein interaction comprises protein degradation. In an embodiment, the protein-protein interaction comprises gene expression. In an embodiment, the protein-protein interaction comprises nucleic acid base editing. In an embodiment, the protein-protein interaction comprises calcium signaling. In an embodiment, the protein-protein interaction comprises calcium entry. In an embodiment, the protein-protein interaction comprises ion channel gating. In an embodiment, the protein-protein interaction comprises gene transcription. In an embodiment, the protein-protein interaction comprises CAR expression.

In an embodiment, the intrabody composition is configured to control binding of an antigen to an antibody. In an embodiment, the binding of the antigen to the antibody is reversible. In an embodiment, the intrabody composition is configured to induce protein homodimerization. In an embodiment, the protein homodimerization is reversible. In an embodiment, the intrabody composition is configured to induce protein heterodimerization. In an embodiment, the protein heterodimerization is reversible.

In an embodiment, the intrabody composition comprises, consists essentially of, or consists of SEQ ID NO:1. In an embodiment, the intrabody composition comprises, consists essentially of, or consists of SEQ ID NO:2. In an embodiment, the intrabody composition comprises, consists essentially of, or consists of SEQ ID NO:3. In an embodiment, the intrabody composition comprises, consists essentially of, or consists of SEQ ID NO:4. In an embodiment, the intrabody composition comprises, consists essentially of, or consists of SEQ ID NO:5. In an embodiment, the intrabody composition comprises, consists essentially of, or consists of SEQ ID NO:6. In an embodiment, the intrabody composition comprises, consists essentially of, or consists of SEQ ID NO:7.

The various sequences described above are summarized below.

SEQ ID NO: 1 ("Moonbody"):
VSSVPTKLEVVDATPTSLKISWDAYYSSWQNVKYYRITYGETGGDSPVQEF

TVPGYYSTATISGLKPGSGLATTLERIEKNFVITDPRLPDNPIIFASDSFL

QLTEYSREEILGRNCRFLQGPETDRATVRKIRDAIDNQTEVTVQLINYTKS

GKKFWNLFHLQPMRDQKGDVQYFIGVQLDGTEHVRDAAEREGVMLIKKTAE

NIDEAAKELGVDYTITVYAYDTFFPGYEPNSPISINYRT

SEQ ID NO: 2 ("Sunbody"):
LATTLERIEKNFVITDPRLPDNPIIFASDSFLQLTEYSREEILGRNCRFLQ

GPETDRATVRKIRDAIDNQTEVTVQLINYTKSGKKFWNLFHLQPMRDQKGD

VQYFIGVQLDGTEHVRDAAEREGVMLIKKTAENIDEAAKELKLMAQVQLVE

SGGGLVQAGGSLRLSCAVSGRPFSEYNLGWFRQAPGKEREFVARIRSSGTT

-continued

VYTDSVKGRFSASRDNALERIEKNFVITDPRLPDNPIIFASDSFLQLTEYS

REEILGRNCRFLQGPETDRATVRKIRDAIDNQTEVTVQLINYTKSGKKFWN

LFHLQPMRDQKGDVQYFIGVQLDGTEHVRDAAEREGVMLIKKTAENIDEAA

KNMGYLQLNSLEPEDTAVYYCAMSRVDTDSPAFYDYWGQGTQVTVSTPRS

SEQ ID NO: 3 ("Caffebody"):
MAQVQLVESGGGLVQAGGSLRLSCAVSGRPFSEYNLGWFRQAPGKEREFVA

RIRSSGTTVYTDSVKGRFSASRDNAEVQLQASGGGLVQAGGSLRLSCTASG

RTGTIYSMAWFRQAPGKEREFLATVGWSSGITYYMDSVKGRFTISRDNAKN

SAYLQMNSLKPEDTAVYYCTATRAYSVGYDYWGQGTQVTVSHAAAGAPVPY

PDPLEPREQKLISEEDLLEAVYSGGGGGGSGGGGGGSGGGGGGSGEVQ

LQASGGGLVQAGGSLRLSCTASGRTGTIYSMAWFRQAPGKEREFLATVGWS

SGITYYMDSVKGRFTISRDNAKNSAYLQMNSLKPEDTAVYYCTATRAYSVG

YDYWGQGTQVTVSKNMGYLQLNSLEPEDTAVYYCAMSRVDTDSPAFYDYWG

QGTQVTVSTPRS

SEQ ID NO: 4 ("Rapabody"):
QLVESGGGLVQAGGSLRLSCAVSGRPFSEYNLGWFRQAPGKEREFVARIRS

SGTTVYTDSVKGRFSASRDNATCVVHYTGMLEDGKKPDSSRDRNKPFKFML

GKQEVIRGWEEGVAQMSVGQRAKLTISPDYAYGATGHGSGSGSGVKDLLQA

WDLYYHVFRRISGPPGPGSGLWHEMWHEGLEEASRLYFGERNVKGMFEVLE

PLHAMMERGPQTLKETSFNQAYGRDLMEAQEWCRKYMKSGSSGGSGSGIIP

PHATLVFDVELLKLEKNMGYLQLNSLEPEDTAVYYCAMSRVDTDSPAFYDY

WGQGTQVTVSTPRS

SEQ ID NO: 5 ("COSMO"):
EVQLQASGGGLVQAGGSLRLSCTASGRTGTIYSMAWFRQAPGKEREFLATV

GWSSGITYYMDSVKGRFTISRDNAKNSAYLQMNSLKPEDTAVYYCTATRAW

SVGYDYWGQGTQVTVS

SEQ ID NO: 6 ("biCOSMO-S"):
EVQLQASGGGLVQAGGSLRLSCTASGRTGTIYSMAWFRQAPGKEREFLATV

GWSSGITYYMDSVKGRFTISRDNAKNSAYLQMNSLKPEDTAVYYCTATRAW

SVGYDYWGQGTQVTVSLHRAEQSLHDLGAPEVQLQASGGGLVQAGGSLRLS

CTASGRTGTIYSMAWFRQAPGKEREFLATVGWSSGITYYMDSVKGRFTISR

DNAKNSAYLQMNSLKPEDTAVYYCTATRAWSVGYDYWGQGTQVTVS

SEQ ID NO: 7 ("biCOSMO-L"):
EVQLQASGGGLVQAGGSLRLSCTASGRTGTIYSMAWFRQAPGKEREFLATV

GWSSGITYYMDSVKGRFTISRDNAKNSAYLQMNSLKPEDTAVYYCTATRAW

SVGYDYWGQGTQVTVSHAAAGAPVPYPDPLEPREQKLISEEDLGGSGGAPE

VQLQASGGGLVQAGGSLRLSCTASGRTGTIYSMAWFRQAPGKEREFLATVG

WSSGITYYMDSVKGRFTISRDNAKNSAYLQMNSLKPEDTAVYYCTATRAWS

VGYDYWGQGTQVTVS

In an illustrative aspect, a method of inducing an interaction between a first protein and a second protein is provided. The method comprises the step of administering an intrabody composition to induce the interaction, wherein the intrabody composition comprises i) an intrabody and ii) one or more inserts.

In an embodiment, the first protein is an antigen. In an embodiment, the second protein is an antibody. In an embodiment, the first protein is an antigen and the second protein is an antibody.

In an embodiment, the interaction is reversible. In an embodiment, the interaction comprises association of the first protein to the second protein. In an embodiment, the interaction comprises disassociation of the first protein to the second protein.

In an embodiment, the interaction comprises protein subcellular translocation. In an embodiment, the interaction comprises protein degradation. In an embodiment, the interaction comprises gene expression. In an embodiment, the interaction comprises nucleic acid base editing. In an embodiment, the interaction comprises calcium signaling. In an embodiment, the interaction comprises calcium entry. In an embodiment, the interaction comprises ion channel gating. In an embodiment, the interaction comprises gene transcription. In an embodiment, the interaction comprises CAR expression. In an embodiment, the interaction comprises protein homodimerization. In an embodiment, the interaction comprises protein heterodimerization.

In an embodiment, the interaction is induced using light. In an embodiment, the interaction is induced using a chemical. In an embodiment, the chemical is rapamycin. In an embodiment, the chemical is a rapamycin metabolite. In an embodiment, the chemical is a rapamycin analog. In an embodiment, the chemical is caffeine. In an embodiment, the chemical is a caffeine metabolite. In an embodiment, the chemical is a caffeine analog.

The previously described embodiments of the intrabody composition are applicable to the method of inducing an interaction between a first protein and a second protein described herein.

In an illustrative aspect, a method of activating an intrabody composition with a chemical is provided. The method comprises the step of contacting the intrabody composition with the chemical, wherein the intrabody composition comprises i) an intrabody and ii) one or more inserts, and wherein the chemical activates the intrabody composition.

In an embodiment, the activation is reversible. In an embodiment, the chemical is rapamycin. In an embodiment, the chemical is a rapamycin metabolite. In an embodiment, the chemical is a rapamycin analog. In an embodiment, the chemical is caffeine. In an embodiment, the chemical is a caffeine metabolite. In an embodiment, the chemical is a caffeine analog.

In an embodiment, the intrabody composition is configured to induce a protein-protein interaction via activation. In an embodiment, the protein-protein interaction comprises association of a first protein to a second protein. In an embodiment, the protein-protein interaction comprises disassociation of a first protein to a second protein. In an embodiment, the protein-protein interaction comprises association of a first protein to a second protein. In an embodiment, the protein-protein interaction comprises protein subcellular translocation. In an embodiment, the protein-protein interaction comprises protein degradation. In an embodiment, the protein-protein interaction comprises gene expression. In an embodiment, the protein-protein interaction comprises nucleic acid base editing. In an embodiment, the protein-protein interaction comprises calcium signaling. In an embodiment, the protein-protein interaction comprises calcium entry. In an embodiment, the protein-protein interaction comprises ion channel gating. In an embodiment, the protein-protein interaction comprises gene transcription. In an embodiment, the protein-protein interaction comprises CAR expression.

In an embodiment, the intrabody composition is configured to control binding of an antigen to an antibody via activation. In an embodiment, the intrabody composition is configured to induce protein homodimerization via activation. In an embodiment, the intrabody composition is configured to induce protein heterodimerization via activation.

The previously described embodiments of the intrabody composition are applicable to the method of activating an intrabody composition with a chemical described herein.

In an illustrative aspect, a method of deactivating an intrabody composition with a chemical is provided. The method comprises the step of contacting the intrabody composition with the chemical, wherein the intrabody composition comprises i) an intrabody and ii) one or more inserts, and wherein the chemical deactivates the intrabody composition.

In an embodiment, the deactivation is reversible. In an embodiment, the chemical is rapamycin. In an embodiment, the chemical is a rapamycin metabolite. In an embodiment, the chemical is a rapamycin analog. In an embodiment, the chemical is caffeine. In an embodiment, the chemical is a caffeine metabolite. In an embodiment, the chemical is a caffeine analog.

In an embodiment, the intrabody composition is configured to induce a protein-protein interaction via deactivation. In an embodiment, the protein-protein interaction comprises association of a first protein to a second protein. In an embodiment, the protein-protein interaction comprises disassociation of a first protein to a second protein. In an embodiment, the protein-protein interaction comprises association of a first protein to a second protein. In an embodiment, the protein-protein interaction comprises protein subcellular translocation. In an embodiment, the protein-protein interaction comprises protein degradation. In an embodiment, the protein-protein interaction comprises gene expression. In an embodiment, the protein-protein interaction comprises nucleic acid base editing. In an embodiment, the protein-protein interaction comprises calcium signaling. In an embodiment, the protein-protein interaction comprises calcium entry. In an embodiment, the protein-protein interaction comprises ion channel gating. In an embodiment, the protein-protein interaction comprises gene transcription. In an embodiment, the protein-protein interaction comprises CAR expression.

In an embodiment, the intrabody composition is configured to control binding of an antigen to an antibody via activation. In an embodiment, the intrabody composition is configured to induce protein homodimerization via activation. In an embodiment, the intrabody composition is configured to induce protein heterodimerization via activation.

The previously described embodiments of the intrabody composition are applicable to the method of deactivating an intrabody composition with a chemical described herein. In addition, the previously described embodiments of the method of activating an intrabody composition with a chemical are also applicable to the method of deactivating an intrabody composition with a chemical described herein.

In an illustrative aspect, a method of activating an intrabody composition with light is provided. The method comprises the step of contacting the intrabody composition with the light, wherein the intrabody composition comprises i) an intrabody and ii) one or more inserts, and wherein the light activates the intrabody composition.

In an embodiment, the activation is reversible. In an embodiment, the intrabody composition is configured to induce a protein-protein interaction via activation.

In an embodiment, the protein-protein interaction comprises association of a first protein to a second protein. In an embodiment, the protein-protein interaction comprises disassociation of a first protein to a second protein. In an embodiment, the protein-protein interaction comprises association of a first protein to a second protein. In an embodiment, the protein-protein interaction comprises protein subcellular translocation. In an embodiment, the protein-protein interaction comprises protein degradation. In an embodiment, the protein-protein interaction comprises gene expression. In an embodiment, the protein-protein interaction comprises nucleic acid base editing. In an embodiment, the protein-protein interaction comprises calcium signaling. In an embodiment, the protein-protein interaction comprises calcium entry. In an embodiment, the protein-protein interaction comprises ion channel gating. In an embodiment, the protein-protein interaction comprises gene transcription. In an embodiment, the protein-protein interaction comprises CAR expression.

In an embodiment, the intrabody composition is configured to control binding of an antigen to an antibody via activation. In an embodiment, the intrabody composition is configured to induce protein homodimerization via activation. In an embodiment, the intrabody composition is configured to induce protein heterodimerization via activation.

The previously described embodiments of the intrabody composition are applicable to the method of activating an intrabody composition with light described herein.

In an illustrative aspect, a method of deactivating an intrabody composition with light is provided. The method comprises the step of contacting the intrabody composition with the light, wherein the intrabody composition comprises i) an intrabody and ii) one or more inserts, and wherein the light deactivates the intrabody composition.

In an embodiment, the deactivation is reversible. In an embodiment, the intrabody composition is configured to induce a protein-protein interaction via deactivation. In an embodiment, the protein-protein interaction comprises association of a first protein to a second protein. In an embodiment, the protein-protein interaction comprises disassociation of a first protein to a second protein. In an embodiment, the protein-protein interaction comprises association of a first protein to a second protein. In an embodiment, the protein-protein interaction comprises protein subcellular translocation. In an embodiment, the protein-protein interaction comprises protein degradation. In an embodiment, the protein-protein interaction comprises gene expression. In an embodiment, the protein-protein interaction comprises nucleic acid base editing. In an embodiment, the protein-protein interaction comprises calcium signaling. In an embodiment, the protein-protein interaction comprises calcium entry. In an embodiment, the protein-protein interaction comprises ion channel gating. In an embodiment, the protein-protein interaction comprises gene transcription. In an embodiment, the protein-protein interaction comprises CAR expression.

In an embodiment, the intrabody composition is configured to control binding of an antigen to an antibody via activation. In an embodiment, the intrabody composition is configured to induce protein homodimerization via activation. In an embodiment, the intrabody composition is configured to induce protein heterodimerization via activation.

The previously described embodiments of the intrabody composition are applicable to the method of deactivating an intrabody composition with light described herein. In addition, the previously described embodiments of the method of activating an intrabody composition with light are also applicable to the method of deactivating an intrabody composition with light described herein.

The following numbered embodiments are contemplated and are non-limiting:

1. An intrabody composition comprising i) an intrabody and ii) one or more inserts.
2. The intrabody composition of clause 1, any other suitable clause, or any combination of suitable clauses, wherein the intrabody is a monobody.
3. The intrabody composition of clause 1, any other suitable clause, or any combination of suitable clauses, wherein the intrabody is a nanobody.
4. The intrabody composition of clause 1, any other suitable clause, or any combination of suitable clauses, wherein the intrabody is a monobody that recognizes the SH2 domain of Abl.
5. The intrabody composition of clause 4, any other suitable clause, or any combination of suitable clauses, wherein the monobody comprises an EF domain.
6. The intrabody composition of clause 1, any other suitable clause, or any combination of suitable clauses, wherein the intrabody is a mCherry-specific nanobody.
7. The intrabody composition of clause 6, any other suitable clause, or any combination of suitable clauses, wherein the mCherry-specific nanobody comprises an S3 loop.
8. The intrabody composition of clause 1, any other suitable clause, or any combination of suitable clauses, wherein the insert is a protein or a protein fragment.
9. The intrabody composition of clause 8, any other suitable clause, or any combination of suitable clauses, wherein the protein comprises a LOV2 fragment.
10. The intrabody composition of clause 8, any other suitable clause, or any combination of suitable clauses, wherein the protein comprises a circularly permuted version of cpLOV2.
11. The intrabody composition of clause 8, any other suitable clause, or any combination of suitable clauses, wherein the protein comprises acVHH.
12. The intrabody composition of clause 8, any other suitable clause, or any combination of suitable clauses, wherein the protein comprises an acVHH variant.
13. The intrabody composition of clause 8, any other suitable clause, or any combination of suitable clauses, wherein the protein comprises UniRapR.
14. The intrabody composition of clause 1, any other suitable clause, or any combination of suitable clauses, wherein the intrabody composition comprises two inserts.
15. The intrabody composition of clause 14, any other suitable clause, or any combination of suitable clauses, wherein the two inserts comprise a first insert and a second insert.
16. The intrabody composition of clause 15, any other suitable clause, or any combination of suitable clauses, wherein the first insert and the second insert are the same.
17. The intrabody composition of clause 15, any other suitable clause, or any combination of suitable clauses, wherein the first insert and the second insert are different.
18. The intrabody composition of clause 15, any other suitable clause, or any combination of suitable clauses, wherein the first insert and the second insert both comprise a LOV2 fragment.
19. The intrabody composition of clause 15, any other suitable clause, or any combination of suitable clauses, wherein the first insert and the second insert both comprise cpLOV2.
20. The intrabody composition of clause 15, any other suitable clause, or any combination of suitable clauses, wherein the first insert and the second insert both comprise a circularly permuted version of cpLOV2.
21. The intrabody composition of clause 15, any other suitable clause, or any combination of suitable clauses, wherein the first insert and the second insert both comprise acVHH.
22. The intrabody composition of clause 15, any other suitable clause, or any combination of suitable clauses, wherein the first insert and the second insert both comprise an acVHH variant.
23. The intrabody composition of clause 1, any other suitable clause, or any combination of suitable clauses, wherein the insert comprises two inserts.
24. The intrabody composition of clause 23, any other suitable clause, or any combination of suitable clauses, wherein the two inserts are contacted via a linker.
25. The intrabody composition of clause 23, any other suitable clause, or any combination of suitable clauses, wherein the two inserts are covalently connected.
26. The intrabody composition of clause 23, any other suitable clause, or any combination of suitable clauses, wherein the two inserts are covalently connected via a linker.
27. The intrabody composition of clause 1, any other suitable clause, or any combination of suitable clauses, wherein the intrabody composition is conjugated to a therapeutic agent.
28. The intrabody composition of clause 27, any other suitable clause, or any combination of suitable clauses, wherein the therapeutic agent is a CAR-T cell.
29. The intrabody composition of clause 27, any other suitable clause, or any combination of suitable clauses, wherein the therapeutic agent is an NK cell.
30. The intrabody composition of clause 27, any other suitable clause, or any combination of suitable clauses, wherein the therapeutic agent is a macrophage.
31. The intrabody composition of clause 27, any other suitable clause, or any combination of suitable clauses, wherein the therapeutic agent is an antibody.
32. The intrabody composition of clause 27, any other suitable clause, or any combination of suitable clauses, wherein the therapeutic agent is an E3 ligase.
33. The intrabody composition of clause 27, any other suitable clause, or any combination of suitable clauses, wherein the therapeutic agent is a TEV protease.
34. The intrabody composition of clause 27, any other suitable clause, or any combination of suitable clauses, wherein the therapeutic agent is transcriptional activator VP64.
35. The intrabody composition of clause 1, any other suitable clause, or any combination of suitable clauses, wherein the intrabody composition is adapted for activation by light.
36. The intrabody composition of clause 35, any other suitable clause, or any combination of suitable clauses, wherein the activation by light is reversible.
37. The intrabody composition of clause 1, any other suitable clause, or any combination of suitable clauses, wherein the intrabody composition is adapted for deactivation by light.
38. The intrabody composition of clause 37, any other suitable clause, or any combination of suitable clauses, wherein the deactivation by light is reversible.
39. The intrabody composition of clause 1, any other suitable clause, or any combination of suitable clauses, wherein the intrabody composition is adapted for activation by a chemical.
40. The intrabody composition of clause 39, any other suitable clause, or any combination of suitable clauses, wherein the activation is reversible.
41. The intrabody composition of clause 39, any other suitable clause, or any combination of suitable clauses, wherein the chemical is rapamycin.
42. The intrabody composition of clause 39, any other suitable clause, or any combination of suitable clauses, wherein the chemical is a rapamycin metabolite.
43. The intrabody composition of clause 39, any other suitable clause, or any combination of suitable clauses, wherein the chemical is a rapamycin analog.
44. The intrabody composition of clause 39, any other suitable clause, or any combination of suitable clauses, wherein the chemical is caffeine.
45. The intrabody composition of clause 39, any other suitable clause, or any combination of suitable clauses, wherein the chemical is a caffeine metabolite.
46. The intrabody composition of clause 39, any other suitable clause, or any combination of suitable clauses, wherein the chemical is a caffeine analog.
47. The intrabody composition of clause 1, any other suitable clause, or any combination of suitable clauses, wherein the intrabody composition is adapted for deactivation by a chemical.
48. The intrabody composition of clause 47, any other suitable clause, or any combination of suitable clauses, wherein the deactivation is reversible.
49. The intrabody composition of clause 47, any other suitable clause, or any combination of suitable clauses, wherein the chemical is rapamycin.
50. The intrabody composition of clause 47, any other suitable clause, or any combination of suitable clauses, wherein the chemical is a rapamycin metabolite.
51. The intrabody composition of clause 47, any other suitable clause, or any combination of suitable clauses, wherein the chemical is a rapamycin analog.
52. The intrabody composition of clause 47, any other suitable clause, or any combination of suitable clauses, wherein the chemical is caffeine.
53. The intrabody composition of clause 47, any other suitable clause, or any combination of suitable clauses, wherein the chemical is a caffeine metabolite.
54. The intrabody composition of clause 47, any other suitable clause, or any combination of suitable clauses, wherein the chemical is a caffeine analog.
55. The intrabody composition of clause 1, any other suitable clause, or any combination of suitable clauses, wherein the intrabody composition is configured to induce a protein-protein interaction.
56. The intrabody composition of clause 55, any other suitable clause, or any combination of suitable clauses, wherein the protein-protein interaction is reversible.
57. The intrabody composition of clause 55, any other suitable clause, or any combination of suitable clauses, wherein the protein-protein interaction comprises association of a first protein to a second protein.
58. The intrabody composition of clause 55, any other suitable clause, or any combination of suitable clauses, wherein the protein-protein interaction comprises disassociation of a first protein to a second protein.
59. The intrabody composition of clause 55, any other suitable clause, or any combination of suitable clauses, wherein the protein-protein interaction comprises association of a first protein to a second protein.
60. The intrabody composition of clause 55, any other suitable clause, or any combination of suitable clauses, wherein the protein-protein interaction comprises protein subcellular translocation.
61. The intrabody composition of clause 55, any other suitable clause, or any combination of suitable clauses, wherein the protein-protein interaction comprises protein degradation.
62. The intrabody composition of clause 55, any other suitable clause, or any combination of suitable clauses, wherein the protein-protein interaction comprises gene expression.
63. The intrabody composition of clause 55, any other suitable clause, or any combination of suitable clauses, wherein the protein-protein interaction comprises nucleic acid base editing.
64. The intrabody composition of clause 55, any other suitable clause, or any combination of suitable clauses, wherein the protein-protein interaction comprises calcium signaling.
65. The intrabody composition of clause 55, any other suitable clause, or any combination of suitable clauses, wherein the protein-protein interaction comprises calcium entry.
66. The intrabody composition of clause 55, any other suitable clause, or any combination of suitable clauses, wherein the protein-protein interaction comprises ion channel gating.
67. The intrabody composition of clause 55, any other suitable clause, or any combination of suitable clauses, wherein the protein-protein interaction comprises gene transcription.
68. The intrabody composition of clause 55, any other suitable clause, or any combination of suitable clauses, wherein the protein-protein interaction comprises CAR expression.
69. The intrabody composition of clause 1, any other suitable clause, or any combination of suitable clauses, wherein the intrabody composition is configured to control binding of an antigen to an antibody.
70. The intrabody composition of clause 69, any other suitable clause, or any combination of suitable clauses, wherein the binding of the antigen to the antibody is reversible.
71. The intrabody composition of clause 1, any other suitable clause, or any combination of suitable clauses, wherein the intrabody composition is configured to induce protein homodimerization.
72. The intrabody composition of clause 71, any other suitable clause, or any combination of suitable clauses, wherein the protein homodimerization is reversible.
73. The intrabody composition of clause 1, any other suitable clause, or any combination of suitable clauses, wherein the intrabody composition is configured to induce protein heterodimerization.
74. The intrabody composition of clause 73, any other suitable clause, or any combination of suitable clauses, wherein the protein heterodimerization is reversible.
75. The intrabody composition of clause 1, any other suitable clause, or any combination of suitable clauses, wherein the intrabody composition comprises SEQ ID NO:1.
76. The intrabody composition of clause 1, any other suitable clause, or any combination of suitable clauses, wherein the intrabody composition consists essentially of SEQ ID NO: 1.
77. The intrabody composition of clause 1, any other suitable clause, or any combination of suitable clauses, wherein the intrabody composition consists of SEQ ID NO: 1.
78. The intrabody composition of clause 1, any other suitable clause, or any combination of suitable clauses, wherein the intrabody composition comprises SEQ ID NO:2.
79. The intrabody composition of clause 1, any other suitable clause, or any combination of suitable clauses, wherein the intrabody composition consists essentially of SEQ ID NO:2.
80. The intrabody composition of clause 1, any other suitable clause, or any combination of suitable clauses, wherein the intrabody composition consists of SEQ ID NO:2.
81. The intrabody composition of clause 1, any other suitable clause, or any combination of suitable clauses, wherein the intrabody composition comprises SEQ ID NO:3.
82. The intrabody composition of clause 1, any other suitable clause, or any combination of suitable clauses, wherein the intrabody composition consists essentially of SEQ ID NO:3.
83. The intrabody composition of clause 1, any other suitable clause, or any combination of suitable clauses, wherein the intrabody composition consists of SEQ ID NO:3.
84. The intrabody composition of clause 1, any other suitable clause, or any combination of suitable clauses, wherein the intrabody composition comprises SEQ ID NO:4.
85. The intrabody composition of clause 1, any other suitable clause, or any combination of suitable clauses, wherein the intrabody composition consists essentially of SEQ ID NO:4.
86. The intrabody composition of clause 1, any other suitable clause, or any combination of suitable clauses, wherein the intrabody composition consists of SEQ ID NO:4.
87. The intrabody composition of clause 1, any other suitable clause, or any combination of suitable clauses, wherein the intrabody composition comprises SEQ ID NO:5.
88. The intrabody composition of clause 1, any other suitable clause, or any combination of suitable clauses, wherein the intrabody composition consists essentially of SEQ ID NO:5.
89. The intrabody composition of clause 1, any other suitable clause, or any combination of suitable clauses, wherein the intrabody composition consists of SEQ ID NO:5.
90. The intrabody composition of clause 1, any other suitable clause, or any combination of suitable clauses, wherein the intrabody composition comprises SEQ ID NO:6.

91. The intrabody composition of clause 1, any other suitable clause, or any combination of suitable clauses, wherein the intrabody composition consists essentially of SEQ ID NO:6.
92. The intrabody composition of clause 1, any other suitable clause, or any combination of suitable clauses, wherein the intrabody composition consists of SEQ ID NO:6.
93. The intrabody composition of clause 1, any other suitable clause, or any combination of suitable clauses, wherein the intrabody composition comprises SEQ ID NO:7.
94. The intrabody composition of clause 1, any other suitable clause, or any combination of suitable clauses, wherein the intrabody composition consists essentially of SEQ ID NO:7.
95. The intrabody composition of clause 1, any other suitable clause, or any combination of suitable clauses, wherein the intrabody composition consists of SEQ ID NO:7.
96. A method of inducing an interaction between a first protein and a second protein, said method comprising the step of administering an intrabody composition to induce the interaction, wherein the intrabody composition comprises i) an intrabody and ii) one or more inserts.
97. The method of clause 96, any other suitable clause, or any combination of suitable clauses, wherein the first protein is an antigen.
98. The method of clause 96, any other suitable clause, or any combination of suitable clauses, wherein the second protein is an antibody.
99. The method of clause 96, any other suitable clause, or any combination of suitable clauses, wherein the first protein is an antigen and the second protein is an antibody.
100. The method of clause 96, any other suitable clause, or any combination of suitable clauses, wherein the interaction is reversible.
101. The method of clause 96, any other suitable clause, or any combination of suitable clauses, wherein the interaction comprises association of the first protein to the second protein.
102. The method of clause 96, any other suitable clause, or any combination of suitable clauses, wherein the interaction comprises disassociation of the first protein to the second protein.
103. The method of clause 96, any other suitable clause, or any combination of suitable clauses, wherein the interaction comprises protein subcellular translocation.
104. The method of clause 96, any other suitable clause, or any combination of suitable clauses, wherein the interaction comprises protein degradation.
105. The method of clause 96, any other suitable clause, or any combination of suitable clauses, wherein the interaction comprises gene expression.
106. The method of clause 96, any other suitable clause, or any combination of suitable clauses, wherein the interaction comprises nucleic acid base editing.
107. The method of clause 96, any other suitable clause, or any combination of suitable clauses, wherein the interaction comprises calcium signaling.
108. The method of clause 96, any other suitable clause, or any combination of suitable clauses, wherein the interaction comprises calcium entry.
109. The method of clause 96, any other suitable clause, or any combination of suitable clauses, wherein the interaction comprises ion channel gating.
110. The method of clause 96, any other suitable clause, or any combination of suitable clauses, wherein the interaction comprises gene transcription.
111. The method of clause 96, any other suitable clause, or any combination of suitable clauses, wherein the interaction comprises CAR expression.
112. The method of clause 96, any other suitable clause, or any combination of suitable clauses, wherein the interaction comprises protein homodimerization.
113. The method of clause 96, any other suitable clause, or any combination of suitable clauses, wherein the interaction comprises protein heterodimerization.
114. The method of clause 96, any other suitable clause, or any combination of suitable clauses, wherein the interaction is induced using light.
115. The method of clause 96, any other suitable clause, or any combination of suitable clauses, wherein the interaction is induced using a chemical.
116. The method of clause 115, any other suitable clause, or any combination of suitable clauses, wherein the chemical is rapamycin.
117. The method of clause 115, any other suitable clause, or any combination of suitable clauses, wherein the chemical is a rapamycin metabolite.
118. The method of clause 115, any other suitable clause, or any combination of suitable clauses, wherein the chemical is a rapamycin analog.
119. The method of clause 115, any other suitable clause, or any combination of suitable clauses, wherein the chemical is caffeine.
120. The method of clause 115, any other suitable clause, or any combination of suitable clauses, wherein the chemical is a caffeine metabolite.
121. The method of clause 115, any other suitable clause, or any combination of suitable clauses, wherein the chemical is a caffeine analog.
122. The method of clause 96, any other suitable clause, or any combination of suitable clauses, wherein the intrabody is a monobody.
123. The method of clause 96, any other suitable clause, or any combination of suitable clauses, wherein the intrabody is a nanobody.
124. The method of clause 96, any other suitable clause, or any combination of suitable clauses, wherein the intrabody is a monobody that recognizes the SH2 domain of Abl.
125. The method of clause 124, any other suitable clause, or any combination of suitable clauses, wherein the monobody comprises an EF domain.
126. The method of clause 96, any other suitable clause, or any combination of suitable clauses, wherein the intrabody is a mCherry-specific nanobody.
127. The method of clause 126, any other suitable clause, or any combination of suitable clauses, wherein the mCherry-specific nanobody comprises an S3 loop.
128. The method of clause 96, any other suitable clause, or any combination of suitable clauses, wherein the insert is a protein or a protein fragment.
129. The method of clause 128, any other suitable clause, or any combination of suitable clauses, wherein the protein comprises a LOV2 fragment.

130. The method of clause 128, any other suitable clause, or any combination of suitable clauses, wherein the protein comprises a circularly permuted version of cpLOV2.
131. The method of clause 128, any other suitable clause, or any combination of suitable clauses, wherein the protein comprises acVHH.
132. The method of clause 128, any other suitable clause, or any combination of suitable clauses, wherein the protein comprises an acVHH variant.
133. The method of clause 128, any other suitable clause, or any combination of suitable clauses, wherein the protein comprises UniRapR.
134. The method of clause 96, any other suitable clause, or any combination of suitable clauses, wherein the intrabody composition comprises two inserts.
135. The method of clause 134, any other suitable clause, or any combination of suitable clauses, wherein the two inserts comprise a first insert and a second insert.
136. The method of clause 135, any other suitable clause, or any combination of suitable clauses, wherein the first insert and the second insert are the same.
137. The method of clause 135, any other suitable clause, or any combination of suitable clauses, wherein the first insert and the second insert are different.
138. The method of clause 135, any other suitable clause, or any combination of suitable clauses, wherein the first insert and the second insert both comprise a LOV2 fragment.
139. The method of clause 135, any other suitable clause, or any combination of suitable clauses, wherein the first insert and the second insert both comprise cpLOV2.
140. The method of clause 135, any other suitable clause, or any combination of suitable clauses, wherein the first insert and the second insert both comprise a circularly permuted version of cpLOV2.
141. The method of clause 135, any other suitable clause, or any combination of suitable clauses, wherein the first insert and the second insert both comprise acVHH.
142. The method of clause 135, any other suitable clause, or any combination of suitable clauses, wherein the first insert and the second insert both comprise an acVHH variant.
143. The method of clause 96, any other suitable clause, or any combination of suitable clauses, wherein the insert comprises two inserts.
144. The method of clause 143, any other suitable clause, or any combination of suitable clauses, wherein the two inserts are contacted via a linker.
145. The method of clause 143, any other suitable clause, or any combination of suitable clauses, wherein the two inserts are covalently connected.
146. The method of clause 143, any other suitable clause, or any combination of suitable clauses, wherein the two inserts are covalently connected via a linker.
147. The method of clause 96, any other suitable clause, or any combination of suitable clauses, wherein the intrabody composition is conjugated to a therapeutic agent.
148. The method of clause 147, any other suitable clause, or any combination of suitable clauses, wherein the therapeutic agent is a CAR-T cell.
149. The method of clause 147, any other suitable clause, or any combination of suitable clauses, wherein the therapeutic agent is an NK cell.
150. The method of clause 147, any other suitable clause, or any combination of suitable clauses, wherein the therapeutic agent is a macrophage.
151. The method of clause 147, any other suitable clause, or any combination of suitable clauses, wherein the therapeutic agent is an antibody.
152. The method of clause 147, any other suitable clause, or any combination of suitable clauses, wherein the therapeutic agent is an E3 ligase.
153. The method of clause 147, any other suitable clause, or any combination of suitable clauses, wherein the therapeutic agent is a TEV protease.
154. The method of clause 147, any other suitable clause, or any combination of suitable clauses, wherein the therapeutic agent is transcriptional activator VP64.
155. The method of clause 96, any other suitable clause, or any combination of suitable clauses, wherein the intrabody composition comprises SEQ ID NO: 1.
156. The method of clause 96, any other suitable clause, or any combination of suitable clauses, wherein the intrabody composition consists essentially of SEQ ID NO:1.
157. The method of clause 96, any other suitable clause, or any combination of suitable clauses, wherein the intrabody composition consists of SEQ ID NO: 1.
158. The method of clause 96, any other suitable clause, or any combination of suitable clauses, wherein the intrabody composition comprises SEQ ID NO:2.
159. The method of clause 96, any other suitable clause, or any combination of suitable clauses, wherein the intrabody composition consists essentially of SEQ ID NO:2.
160. The method of clause 96, any other suitable clause, or any combination of suitable clauses, wherein the intrabody composition consists of SEQ ID NO:2.
161. The method of clause 96, any other suitable clause, or any combination of suitable clauses, wherein the intrabody composition comprises SEQ ID NO:3.
162. The method of clause 96, any other suitable clause, or any combination of suitable clauses, wherein the intrabody composition consists essentially of SEQ ID NO:3.
163. The method of clause 96, any other suitable clause, or any combination of suitable clauses, wherein the intrabody composition consists of SEQ ID NO:3.
164. The method of clause 96, any other suitable clause, or any combination of suitable clauses, wherein the intrabody composition comprises SEQ ID NO:4.
165. The method of clause 96, any other suitable clause, or any combination of suitable clauses, wherein the intrabody composition consists essentially of SEQ ID NO:4.
166. The method of clause 96, any other suitable clause, or any combination of suitable clauses, wherein the intrabody composition consists of SEQ ID NO:4.
167. The method of clause 96, any other suitable clause, or any combination of suitable clauses, wherein the intrabody composition comprises SEQ ID NO:5.
168. The method of clause 96, any other suitable clause, or any combination of suitable clauses, wherein the intrabody composition consists essentially of SEQ ID NO:5.
169. The method of clause 96, any other suitable clause, or any combination of suitable clauses, wherein the intrabody composition consists of SEQ ID NO:5.

170. The method of clause 96, any other suitable clause, or any combination of suitable clauses, wherein the intrabody composition comprises SEQ ID NO:6.
171. The method of clause 96, any other suitable clause, or any combination of suitable clauses, wherein the intrabody composition consists essentially of SEQ ID NO:6.
172. The method of clause 96, any other suitable clause, or any combination of suitable clauses, wherein the intrabody composition consists of SEQ ID NO:6.
173. The method of clause 96, any other suitable clause, or any combination of suitable clauses, wherein the intrabody composition comprises SEQ ID NO:7.
174. The method of clause 96, any other suitable clause, or any combination of suitable clauses, wherein the intrabody composition consists essentially of SEQ ID NO:7.
175. The method of clause 96, any other suitable clause, or any combination of suitable clauses, wherein the intrabody composition consists of SEQ ID NO:7.
176. A method of activating an intrabody composition with a chemical, said method comprising the step of contacting the intrabody composition with the chemical, wherein the intrabody composition comprises i) an intrabody and ii) one or more inserts, and wherein the chemical activates the intrabody composition.
177. The method of clause 176, any other suitable clause, or any combination of suitable clauses, wherein the activation is reversible.
178. The method of clause 176, any other suitable clause, or any combination of suitable clauses, wherein the chemical is rapamycin.
179. The method of clause 176, any other suitable clause, or any combination of suitable clauses, wherein the chemical is a rapamycin metabolite.
180. The method of clause 176, any other suitable clause, or any combination of suitable clauses, wherein the chemical is a rapamycin analog.
181. The method of clause 176, any other suitable clause, or any combination of suitable clauses, wherein the chemical is caffeine.
182. The method of clause 176, any other suitable clause, or any combination of suitable clauses, wherein the chemical is a caffeine metabolite.
183. The method of clause 176, any other suitable clause, or any combination of suitable clauses, wherein the chemical is a caffeine analog.
184. The method of clause 176, any other suitable clause, or any combination of suitable clauses, wherein the intrabody composition is configured to induce a protein-protein interaction via activation.
185. The method of clause 184, any other suitable clause, or any combination of suitable clauses, wherein the protein-protein interaction comprises association of a first protein to a second protein.
186. The method of clause 184, any other suitable clause, or any combination of suitable clauses, wherein the protein-protein interaction comprises disassociation of a first protein to a second protein.
187. The method of clause 184, any other suitable clause, or any combination of suitable clauses, wherein the protein-protein interaction comprises association of a first protein to a second protein.
188. The method of clause 184, any other suitable clause, or any combination of suitable clauses, wherein the protein-protein interaction comprises protein subcellular translocation.
189. The method of clause 184, any other suitable clause, or any combination of suitable clauses, wherein the protein-protein interaction comprises protein degradation.
190. The method of clause 184, any other suitable clause, or any combination of suitable clauses, wherein the protein-protein interaction comprises gene expression.
191. The method of clause 184, any other suitable clause, or any combination of suitable clauses, wherein the protein-protein interaction comprises nucleic acid base editing.
192. The method of clause 184, any other suitable clause, or any combination of suitable clauses, wherein the protein-protein interaction comprises calcium signaling.
193. The method of clause 184, any other suitable clause, or any combination of suitable clauses, wherein the protein-protein interaction comprises calcium entry.
194. The method of clause 184, any other suitable clause, or any combination of suitable clauses, wherein the protein-protein interaction comprises ion channel gating.
195. The method of clause 184, any other suitable clause, or any combination of suitable clauses, wherein the protein-protein interaction comprises gene transcription.
196. The method of clause 184, any other suitable clause, or any combination of suitable clauses, wherein the protein-protein interaction comprises CAR expression.
197. The method of clause 176, any other suitable clause, or any combination of suitable clauses, wherein the intrabody composition is configured to control binding of an antigen to an antibody via activation.
198. The method of clause 176, any other suitable clause, or any combination of suitable clauses, wherein the intrabody composition is configured to induce protein homodimerization via activation.
199. The method of clause 176, any other suitable clause, or any combination of suitable clauses, wherein the intrabody composition is configured to induce protein heterodimerization via activation.
200. The method of clause 176, any other suitable clause, or any combination of suitable clauses, wherein the intrabody is a monobody.
201. The method of clause 176, any other suitable clause, or any combination of suitable clauses, wherein the intrabody is a nanobody.
202. The method of clause 176, any other suitable clause, or any combination of suitable clauses, wherein the intrabody is a monobody that recognizes the SH2 domain of Abl.
203. The method of clause 202, any other suitable clause, or any combination of suitable clauses, wherein the monobody comprises an EF domain.
204. The method of clause 176, any other suitable clause, or any combination of suitable clauses, wherein the intrabody is a mCherry-specific nanobody.
205. The method of clause 204, any other suitable clause, or any combination of suitable clauses, wherein the mCherry-specific nanobody comprises an S3 loop.
206. The method of clause 176, any other suitable clause, or any combination of suitable clauses, wherein the insert is a protein or a protein fragment.
207. The method of clause 206, any other suitable clause, or any combination of suitable clauses, wherein the protein comprises a LOV2 fragment.

208. The method of clause 206, any other suitable clause, or any combination of suitable clauses, wherein the protein comprises a circularly permuted version of cpLOV2.
209. The method of clause 206, any other suitable clause, or any combination of suitable clauses, wherein the protein comprises acVHH.
210. The method of clause 206, any other suitable clause, or any combination of suitable clauses, wherein the protein comprises an acVHH variant.
211. The method of clause 206, any other suitable clause, or any combination of suitable clauses, wherein the protein comprises UniRapR.
212. The method of clause 176, any other suitable clause, or any combination of suitable clauses, wherein the intrabody composition comprises two inserts.
213. The method of clause 212, any other suitable clause, or any combination of suitable clauses, wherein the two inserts comprise a first insert and a second insert.
214. The method of clause 213, any other suitable clause, or any combination of suitable clauses, wherein the first insert and the second insert are the same.
215. The method of clause 213, any other suitable clause, or any combination of suitable clauses, wherein the first insert and the second insert are different.
216. The method of clause 213, any other suitable clause, or any combination of suitable clauses, wherein the first insert and the second insert both comprise a LOV2 fragment.
217. The method of clause 213, any other suitable clause, or any combination of suitable clauses, wherein the first insert and the second insert both comprise cpLOV2.
218. The method of clause 213, any other suitable clause, or any combination of suitable clauses, wherein the first insert and the second insert both comprise a circularly permuted version of cpLOV2.
219. The method of clause 213, any other suitable clause, or any combination of suitable clauses, wherein the first insert and the second insert both comprise acVHH.
220. The method of clause 213, any other suitable clause, or any combination of suitable clauses, wherein the first insert and the second insert both comprise an acVHH variant.
221. The method of clause 176, any other suitable clause, or any combination of suitable clauses, wherein the insert comprises two inserts.
222. The method of clause 221, any other suitable clause, or any combination of suitable clauses, wherein the two inserts are contacted via a linker.
223. The method of clause 221, any other suitable clause, or any combination of suitable clauses, wherein the two inserts are covalently connected.
224. The method of clause 221, any other suitable clause, or any combination of suitable clauses, wherein the two inserts are covalently connected via a linker.
225. The method of clause 176, any other suitable clause, or any combination of suitable clauses, wherein the intrabody composition is conjugated to a therapeutic agent.
226. The method of clause 225, any other suitable clause, or any combination of suitable clauses, wherein the therapeutic agent is a CAR-T cell.
227. The method of clause 225, any other suitable clause, or any combination of suitable clauses, wherein the therapeutic agent is an NK cell.
228. The method of clause 225, any other suitable clause, or any combination of suitable clauses, wherein the therapeutic agent is a macrophage.
229. The method of clause 225, any other suitable clause, or any combination of suitable clauses, wherein the therapeutic agent is an antibody.
230. The method of clause 225, any other suitable clause, or any combination of suitable clauses, wherein the therapeutic agent is an E3 ligase.
231. The method of clause 225, any other suitable clause, or any combination of suitable clauses, wherein the therapeutic agent is a TEV protease.
232. The method of clause 225, any other suitable clause, or any combination of suitable clauses, wherein the therapeutic agent is transcriptional activator VP64.
233. The method of clause 176, any other suitable clause, or any combination of suitable clauses, wherein the intrabody composition comprises SEQ ID NO: 1.
234. The method of clause 176, any other suitable clause, or any combination of suitable clauses, wherein the intrabody composition consists essentially of SEQ ID NO:1.
235. The method of clause 176, any other suitable clause, or any combination of suitable clauses, wherein the intrabody composition consists of SEQ ID NO:1.
236. The method of clause 176, any other suitable clause, or any combination of suitable clauses, wherein the intrabody composition comprises SEQ ID NO:2.
237. The method of clause 176, any other suitable clause, or any combination of suitable clauses, wherein the intrabody composition consists essentially of SEQ ID NO:2.
238. The method of clause 176, any other suitable clause, or any combination of suitable clauses, wherein the intrabody composition consists of SEQ ID NO:2.
239. The method of clause 176, any other suitable clause, or any combination of suitable clauses, wherein the intrabody composition comprises SEQ ID NO:3.
240. The method of clause 176, any other suitable clause, or any combination of suitable clauses, wherein the intrabody composition consists essentially of SEQ ID NO:3.
241. The method of clause 176, any other suitable clause, or any combination of suitable clauses, wherein the intrabody composition consists of SEQ ID NO:3.
242. The method of clause 176, any other suitable clause, or any combination of suitable clauses, wherein the intrabody composition comprises SEQ ID NO:4.
243. The method of clause 176, any other suitable clause, or any combination of suitable clauses, wherein the intrabody composition consists essentially of SEQ ID NO:4.
244. The method of clause 176, any other suitable clause, or any combination of suitable clauses, wherein the intrabody composition consists of SEQ ID NO:4.
245. The method of clause 176, any other suitable clause, or any combination of suitable clauses, wherein the intrabody composition comprises SEQ ID NO:5.
246. The method of clause 176, any other suitable clause, or any combination of suitable clauses, wherein the intrabody composition consists essentially of SEQ ID NO:5.
247. The method of clause 176, any other suitable clause, or any combination of suitable clauses, wherein the intrabody composition consists of SEQ ID NO:5.

248. The method of clause 176, any other suitable clause, or any combination of suitable clauses, wherein the intrabody composition comprises SEQ ID NO:6.
249. The method of clause 176, any other suitable clause, or any combination of suitable clauses, wherein the intrabody composition consists essentially of SEQ ID NO:6.
250. The method of clause 176, any other suitable clause, or any combination of suitable clauses, wherein the intrabody composition consists of SEQ ID NO:6.
251. The method of clause 176, any other suitable clause, or any combination of suitable clauses, wherein the intrabody composition comprises SEQ ID NO:7.
252. The method of clause 176, any other suitable clause, or any combination of suitable clauses, wherein the intrabody composition consists essentially of SEQ ID NO:7.
253. The method of clause 176, any other suitable clause, or any combination of suitable clauses, wherein the intrabody composition consists of SEQ ID NO:7.
254. A method of deactivating an intrabody composition with a chemical, said method comprising the step of contacting the intrabody composition with the chemical, wherein the intrabody composition comprises i) an intrabody and ii) one or more inserts, and wherein the chemical deactivates the intrabody composition.
255. The method of clause 254, any other suitable clause, or any combination of suitable clauses, wherein the deactivation is reversible.
256. The method of clause 254, any other suitable clause, or any combination of suitable clauses, wherein the chemical is rapamycin.
257. The method of clause 254, any other suitable clause, or any combination of suitable clauses, wherein the chemical is a rapamycin metabolite.
258. The method of clause 254, any other suitable clause, or any combination of suitable clauses, wherein the chemical is a rapamycin analog.
259. The method of clause 254, any other suitable clause, or any combination of suitable clauses, wherein the chemical is caffeine.
260. The method of clause 254, any other suitable clause, or any combination of suitable clauses, wherein the chemical is a caffeine metabolite.
261. The method of clause 254, any other suitable clause, or any combination of suitable clauses, wherein the chemical is a caffeine analog.
262. The method of clause 254, any other suitable clause, or any combination of suitable clauses, wherein the intrabody composition is configured to induce a protein-protein interaction via deactivation.
263. The method of clause 262, any other suitable clause, or any combination of suitable clauses, wherein the protein-protein interaction comprises association of a first protein to a second protein.
264. The method of clause 262, any other suitable clause, or any combination of suitable clauses, wherein the protein-protein interaction comprises disassociation of a first protein to a second protein.
265. The method of clause 262, any other suitable clause, or any combination of suitable clauses, wherein the protein-protein interaction comprises association of a first protein to a second protein.
266. The method of clause 262, any other suitable clause, or any combination of suitable clauses, wherein the protein-protein interaction comprises protein subcellular translocation.
267. The method of clause 262, any other suitable clause, or any combination of suitable clauses, wherein the protein-protein interaction comprises protein degradation.
268. The method of clause 262, any other suitable clause, or any combination of suitable clauses, wherein the protein-protein interaction comprises gene expression.
269. The method of clause 262, any other suitable clause, or any combination of suitable clauses, wherein the protein-protein interaction comprises nucleic acid base editing.
270. The method of clause 262, any other suitable clause, or any combination of suitable clauses, wherein the protein-protein interaction comprises calcium signaling.
271. The method of clause 262, any other suitable clause, or any combination of suitable clauses, wherein the protein-protein interaction comprises calcium entry.
272. The method of clause 262, any other suitable clause, or any combination of suitable clauses, wherein the protein-protein interaction comprises ion channel gating.
273. The method of clause 262, any other suitable clause, or any combination of suitable clauses, wherein the protein-protein interaction comprises gene transcription.
274. The method of clause 262, any other suitable clause, or any combination of suitable clauses, wherein the protein-protein interaction comprises CAR expression.
275. The method of clause 254, any other suitable clause, or any combination of suitable clauses, wherein the intrabody composition is configured to control binding of an antigen to an antibody via activation.
276. The method of clause 254, any other suitable clause, or any combination of suitable clauses, wherein the intrabody composition is configured to induce protein homodimerization via activation.
277. The method of clause 254, any other suitable clause, or any combination of suitable clauses, wherein the intrabody composition is configured to induce protein heterodimerization via activation.
278. The method of clause 254, any other suitable clause, or any combination of suitable clauses, wherein the intrabody is a monobody.
279. The method of clause 254, any other suitable clause, or any combination of suitable clauses, wherein the intrabody is a nanobody.
280. The method of clause 254, any other suitable clause, or any combination of suitable clauses, wherein the intrabody is a monobody that recognizes the SH2 domain of Abl.
281. The method of clause 280, any other suitable clause, or any combination of suitable clauses, wherein the monobody comprises an EF domain.
282. The method of clause 254, any other suitable clause, or any combination of suitable clauses, wherein the intrabody is a mCherry-specific nanobody.
283. The method of clause 282, any other suitable clause, or any combination of suitable clauses, wherein the mCherry-specific nanobody comprises an S3 loop.
284. The method of clause 254, any other suitable clause, or any combination of suitable clauses, wherein the insert is a protein or a protein fragment.
285. The method of clause 284, any other suitable clause, or any combination of suitable clauses, wherein the protein comprises a LOV2 fragment.

286. The method of clause 284, any other suitable clause, or any combination of suitable clauses, wherein the protein comprises a circularly permuted version of cpLOV2.
287. The method of clause 284, any other suitable clause, or any combination of suitable clauses, wherein the protein comprises acVHH.
288. The method of clause 284, any other suitable clause, or any combination of suitable clauses, wherein the protein comprises an acVHH variant.
289. The method of clause 284, any other suitable clause, or any combination of suitable clauses, wherein the protein comprises UniRapR.
290. The method of clause 254, any other suitable clause, or any combination of suitable clauses, wherein the intrabody composition comprises two inserts.
291. The method of clause 290, any other suitable clause, or any combination of suitable clauses, wherein the two inserts comprise a first insert and a second insert.
292. The method of clause 291, any other suitable clause, or any combination of suitable clauses, wherein the first insert and the second insert are the same.
293. The method of clause 291, any other suitable clause, or any combination of suitable clauses, wherein the first insert and the second insert are different.
294. The method of clause 291, any other suitable clause, or any combination of suitable clauses, wherein the first insert and the second insert both comprise a LOV2 fragment.
295. The method of clause 291, any other suitable clause, or any combination of suitable clauses, wherein the first insert and the second insert both comprise cpLOV2.
296. The method of clause 291, any other suitable clause, or any combination of suitable clauses, wherein the first insert and the second insert both comprise a circularly permuted version of cpLOV2.
297. The method of clause 291, any other suitable clause, or any combination of suitable clauses, wherein the first insert and the second insert both comprise acVHH.
298. The method of clause 291, any other suitable clause, or any combination of suitable clauses, wherein the first insert and the second insert both comprise an acVHH variant.
299. The method of clause 254, any other suitable clause, or any combination of suitable clauses, wherein the insert comprises two inserts.
300. The method of clause 299, any other suitable clause, or any combination of suitable clauses, wherein the two inserts are contacted via a linker.
301. The method of clause 299, any other suitable clause, or any combination of suitable clauses, wherein the two inserts are covalently connected.
302. The method of clause 299, any other suitable clause, or any combination of suitable clauses, wherein the two inserts are covalently connected via a linker.
303. The method of clause 254, any other suitable clause, or any combination of suitable clauses, wherein the intrabody composition is conjugated to a therapeutic agent.
304. The method of clause 303, any other suitable clause, or any combination of suitable clauses, wherein the therapeutic agent is a CAR-T cell.
305. The method of clause 303, any other suitable clause, or any combination of suitable clauses, wherein the therapeutic agent is an NK cell.
306. The method of clause 303, any other suitable clause, or any combination of suitable clauses, wherein the therapeutic agent is a macrophage.
307. The method of clause 303, any other suitable clause, or any combination of suitable clauses, wherein the therapeutic agent is an antibody.
308. The method of clause 303, any other suitable clause, or any combination of suitable clauses, wherein the therapeutic agent is an E3 ligase.
309. The method of clause 303, any other suitable clause, or any combination of suitable clauses, wherein the therapeutic agent is a TEV protease.
310. The method of clause 303, any other suitable clause, or any combination of suitable clauses, wherein the therapeutic agent is transcriptional activator VP64.
311. The method of clause 254, any other suitable clause, or any combination of suitable clauses, wherein the intrabody composition comprises SEQ ID NO:1.
312. The method of clause 254, any other suitable clause, or any combination of suitable clauses, wherein the intrabody composition consists essentially of SEQ ID NO:1.
313. The method of clause 254, any other suitable clause, or any combination of suitable clauses, wherein the intrabody composition consists of SEQ ID NO:1.
314. The method of clause 254, any other suitable clause, or any combination of suitable clauses, wherein the intrabody composition comprises SEQ ID NO:2.
315. The method of clause 254, any other suitable clause, or any combination of suitable clauses, wherein the intrabody composition consists essentially of SEQ ID NO:2.
316. The method of clause 254, any other suitable clause, or any combination of suitable clauses, wherein the intrabody composition consists of SEQ ID NO:2.
317. The method of clause 254, any other suitable clause, or any combination of suitable clauses, wherein the intrabody composition comprises SEQ ID NO:3.
318. The method of clause 254, any other suitable clause, or any combination of suitable clauses, wherein the intrabody composition consists essentially of SEQ ID NO:3.
319. The method of clause 254, any other suitable clause, or any combination of suitable clauses, wherein the intrabody composition consists of SEQ ID NO:3.
320. The method of clause 254, any other suitable clause, or any combination of suitable clauses, wherein the intrabody composition comprises SEQ ID NO:4.
321. The method of clause 254, any other suitable clause, or any combination of suitable clauses, wherein the intrabody composition consists essentially of SEQ ID NO:4.
322. The method of clause 254, any other suitable clause, or any combination of suitable clauses, wherein the intrabody composition consists of SEQ ID NO:4.
323. The method of clause 254, any other suitable clause, or any combination of suitable clauses, wherein the intrabody composition comprises SEQ ID NO:5.
324. The method of clause 254, any other suitable clause, or any combination of suitable clauses, wherein the intrabody composition consists essentially of SEQ ID NO:5.
325. The method of clause 254, any other suitable clause, or any combination of suitable clauses, wherein the intrabody composition consists of SEQ ID NO:5.

326. The method of clause 254, any other suitable clause, or any combination of suitable clauses, wherein the intrabody composition comprises SEQ ID NO:6.
327. The method of clause 254, any other suitable clause, or any combination of suitable clauses, wherein the intrabody composition consists essentially of SEQ ID NO:6.
328. The method of clause 254, any other suitable clause, or any combination of suitable clauses, wherein the intrabody composition consists of SEQ ID NO:6.
329. The method of clause 254, any other suitable clause, or any combination of suitable clauses, wherein the intrabody composition comprises SEQ ID NO:7.
330. The method of clause 254, any other suitable clause, or any combination of suitable clauses, wherein the intrabody composition consists essentially of SEQ ID NO:7.
331. The method of clause 254, any other suitable clause, or any combination of suitable clauses, wherein the intrabody composition consists of SEQ ID NO:7.
332. A method of activating an intrabody composition with light, said method comprising the step of contacting the intrabody composition with the light, wherein the intrabody composition comprises i) an intrabody and ii) one or more inserts, and wherein the light activates the intrabody composition.
333. The method of clause 332, any other suitable clause, or any combination of suitable clauses, wherein the activation is reversible.
334. The method of clause 332, any other suitable clause, or any combination of suitable clauses, wherein the intrabody composition is configured to induce a protein-protein interaction via activation.
335. The method of clause 334, any other suitable clause, or any combination of suitable clauses, wherein the protein-protein interaction comprises association of a first protein to a second protein.
336. The method of clause 334, any other suitable clause, or any combination of suitable clauses, wherein the protein-protein interaction comprises disassociation of a first protein to a second protein.
337. The method of clause 334, any other suitable clause, or any combination of suitable clauses, wherein the protein-protein interaction comprises association of a first protein to a second protein.
338. The method of clause 334, any other suitable clause, or any combination of suitable clauses, wherein the protein-protein interaction comprises protein subcellular translocation.
339. The method of clause 334, any other suitable clause, or any combination of suitable clauses, wherein the protein-protein interaction comprises protein degradation.
340. The method of clause 334, any other suitable clause, or any combination of suitable clauses, wherein the protein-protein interaction comprises gene expression.
341. The method of clause 334, any other suitable clause, or any combination of suitable clauses, wherein the protein-protein interaction comprises nucleic acid base editing.
342. The method of clause 334, any other suitable clause, or any combination of suitable clauses, wherein the protein-protein interaction comprises calcium signaling.
343. The method of clause 334, any other suitable clause, or any combination of suitable clauses, wherein the protein-protein interaction comprises calcium entry.
344. The method of clause 334, any other suitable clause, or any combination of suitable clauses, wherein the protein-protein interaction comprises ion channel gating.
345. The method of clause 334, any other suitable clause, or any combination of suitable clauses, wherein the protein-protein interaction comprises gene transcription.
346. The method of clause 334, any other suitable clause, or any combination of suitable clauses, wherein the protein-protein interaction comprises CAR expression.
347. The method of clause 332, any other suitable clause, or any combination of suitable clauses, wherein the intrabody composition is configured to control binding of an antigen to an antibody via activation.
348. The method of clause 332, any other suitable clause, or any combination of suitable clauses, wherein the intrabody composition is configured to induce protein homodimerization via activation.
349. The method of clause 332, any other suitable clause, or any combination of suitable clauses, wherein the intrabody composition is configured to induce protein heterodimerization via activation.
350. The method of clause 332, any other suitable clause, or any combination of suitable clauses, wherein the intrabody is a monobody.
351. The method of clause 332, any other suitable clause, or any combination of suitable clauses, wherein the intrabody is a nanobody.
352. The method of clause 332, any other suitable clause, or any combination of suitable clauses, wherein the intrabody is a monobody that recognizes the SH2 domain of Abl.
353. The method of clause 352, any other suitable clause, or any combination of suitable clauses, wherein the monobody comprises an EF domain.
354. The method of clause 332, any other suitable clause, or any combination of suitable clauses, wherein the intrabody is a mCherry-specific nanobody.
355. The method of clause 354, any other suitable clause, or any combination of suitable clauses, wherein the mCherry-specific nanobody comprises an S3 loop.
356. The method of clause 332, any other suitable clause, or any combination of suitable clauses, wherein the insert is a protein or a protein fragment.
357. The method of clause 356, any other suitable clause, or any combination of suitable clauses, wherein the protein comprises a LOV2 fragment.
358. The method of clause 356, any other suitable clause, or any combination of suitable clauses, wherein the protein comprises a circularly permuted version of cpLOV2.
359. The method of clause 356, any other suitable clause, or any combination of suitable clauses, wherein the protein comprises acVHH.
360. The method of clause 356, any other suitable clause, or any combination of suitable clauses, wherein the protein comprises an acVHH variant.
361. The method of clause 356, any other suitable clause, or any combination of suitable clauses, wherein the protein comprises UniRapR.
362. The method of clause 332, any other suitable clause, or any combination of suitable clauses, wherein the intrabody composition comprises two inserts.
363. The method of clause 362, any other suitable clause, or any combination of suitable clauses, wherein the two inserts comprise a first insert and a second insert.

364. The method of clause 363, any other suitable clause, or any combination of suitable clauses, wherein the first insert and the second insert are the same.
365. The method of clause 363, any other suitable clause, or any combination of suitable clauses, wherein the first insert and the second insert are different.
366. The method of clause 363, any other suitable clause, or any combination of suitable clauses, wherein the first insert and the second insert both comprise a LOV2 fragment.
367. The method of clause 363, any other suitable clause, or any combination of suitable clauses, wherein the first insert and the second insert both comprise cpLOV2.
368. The method of clause 363, any other suitable clause, or any combination of suitable clauses, wherein the first insert and the second insert both comprise a circularly permuted version of cpLOV2.
369. The method of clause 363, any other suitable clause, or any combination of suitable clauses, wherein the first insert and the second insert both comprise acVHH.
370. The method of clause 363, any other suitable clause, or any combination of suitable clauses, wherein the first insert and the second insert both comprise an acVHH variant.
371. The method of clause 332, any other suitable clause, or any combination of suitable clauses, wherein the insert comprises two inserts.
372. The method of clause 371, any other suitable clause, or any combination of suitable clauses, wherein the two inserts are contacted via a linker.
373. The method of clause 371, any other suitable clause, or any combination of suitable clauses, wherein the two inserts are covalently connected.
374. The method of clause 371, any other suitable clause, or any combination of suitable clauses, wherein the two inserts are covalently connected via a linker.
375. The method of clause 332, any other suitable clause, or any combination of suitable clauses, wherein the intrabody composition is conjugated to a therapeutic agent.
376. The method of clause 375, any other suitable clause, or any combination of suitable clauses, wherein the therapeutic agent is a CAR-T cell.
377. The method of clause 375, any other suitable clause, or any combination of suitable clauses, wherein the therapeutic agent is an NK cell.
378. The method of clause 375, any other suitable clause, or any combination of suitable clauses, wherein the therapeutic agent is a macrophage.
379. The method of clause 375, any other suitable clause, or any combination of suitable clauses, wherein the therapeutic agent is an antibody.
380. The method of clause 375, any other suitable clause, or any combination of suitable clauses, wherein the therapeutic agent is an E3 ligase.
381. The method of clause 375, any other suitable clause, or any combination of suitable clauses, wherein the therapeutic agent is a TEV protease.
382. The method of clause 375, any other suitable clause, or any combination of suitable clauses, wherein the therapeutic agent is transcriptional activator VP64.
383. The method of clause 332, any other suitable clause, or any combination of suitable clauses, wherein the intrabody composition comprises SEQ ID NO: 1.
384. The method of clause 332, any other suitable clause, or any combination of suitable clauses, wherein the intrabody composition consists essentially of SEQ ID NO:1.
385. The method of clause 332, any other suitable clause, or any combination of suitable clauses, wherein the intrabody composition consists of SEQ ID NO: 1.
386. The method of clause 332, any other suitable clause, or any combination of suitable clauses, wherein the intrabody composition comprises SEQ ID NO:2.
387. The method of clause 332, any other suitable clause, or any combination of suitable clauses, wherein the intrabody composition consists essentially of SEQ ID NO:2.
388. The method of clause 332, any other suitable clause, or any combination of suitable clauses, wherein the intrabody composition consists of SEQ ID NO:2.
389. The method of clause 332, any other suitable clause, or any combination of suitable clauses, wherein the intrabody composition comprises SEQ ID NO:3.
390. The method of clause 332, any other suitable clause, or any combination of suitable clauses, wherein the intrabody composition consists essentially of SEQ ID NO:3.
391. The method of clause 332, any other suitable clause, or any combination of suitable clauses, wherein the intrabody composition consists of SEQ ID NO:3.
392. The method of clause 332, any other suitable clause, or any combination of suitable clauses, wherein the intrabody composition comprises SEQ ID NO:4.
393. The method of clause 332, any other suitable clause, or any combination of suitable clauses, wherein the intrabody composition consists essentially of SEQ ID NO:4.
394. The method of clause 332, any other suitable clause, or any combination of suitable clauses, wherein the intrabody composition consists of SEQ ID NO:4.
395. The method of clause 332, any other suitable clause, or any combination of suitable clauses, wherein the intrabody composition comprises SEQ ID NO:5.
396. The method of clause 332, any other suitable clause, or any combination of suitable clauses, wherein the intrabody composition consists essentially of SEQ ID NO:5.
397. The method of clause 332, any other suitable clause, or any combination of suitable clauses, wherein the intrabody composition consists of SEQ ID NO:5.
398. The method of clause 332, any other suitable clause, or any combination of suitable clauses, wherein the intrabody composition comprises SEQ ID NO:6.
399. The method of clause 332, any other suitable clause, or any combination of suitable clauses, wherein the intrabody composition consists essentially of SEQ ID NO:6.
400. The method of clause 332, any other suitable clause, or any combination of suitable clauses, wherein the intrabody composition consists of SEQ ID NO:6.
401. The method of clause 332, any other suitable clause, or any combination of suitable clauses, wherein the intrabody composition comprises SEQ ID NO:7.
402. The method of clause 332, any other suitable clause, or any combination of suitable clauses, wherein the intrabody composition consists essentially of SEQ ID NO:7.
403. The method of clause 332, any other suitable clause, or any combination of suitable clauses, wherein the intrabody composition consists of SEQ ID NO:7.

404. A method of deactivating an intrabody composition with light, said method comprising the step of contacting the intrabody composition with the light, wherein the intrabody composition comprises i) an intrabody and ii) one or more inserts, and wherein the light deactivates the intrabody composition.

405. The method of clause 404, any other suitable clause, or any combination of suitable clauses, wherein the deactivation is reversible.

406. The method of clause 404, any other suitable clause, or any combination of suitable clauses, wherein the intrabody composition is configured to induce a protein-protein interaction via deactivation.

407. The method of clause 406, any other suitable clause, or any combination of suitable clauses, wherein the protein-protein interaction comprises association of a first protein to a second protein.

408. The method of clause 406, any other suitable clause, or any combination of suitable clauses, wherein the protein-protein interaction comprises disassociation of a first protein to a second protein.

409. The method of clause 406, any other suitable clause, or any combination of suitable clauses, wherein the protein-protein interaction comprises association of a first protein to a second protein.

410. The method of clause 406, any other suitable clause, or any combination of suitable clauses, wherein the protein-protein interaction comprises protein subcellular translocation.

411. The method of clause 406, any other suitable clause, or any combination of suitable clauses, wherein the protein-protein interaction comprises protein degradation.

412. The method of clause 406, any other suitable clause, or any combination of suitable clauses, wherein the protein-protein interaction comprises gene expression.

413. The method of clause 406, any other suitable clause, or any combination of suitable clauses, wherein the protein-protein interaction comprises nucleic acid base editing.

414. The method of clause 406, any other suitable clause, or any combination of suitable clauses, wherein the protein-protein interaction comprises calcium signaling.

415. The method of clause 406, any other suitable clause, or any combination of suitable clauses, wherein the protein-protein interaction comprises calcium entry.

416. The method of clause 406, any other suitable clause, or any combination of suitable clauses, wherein the protein-protein interaction comprises ion channel gating.

417. The method of clause 406, any other suitable clause, or any combination of suitable clauses, wherein the protein-protein interaction comprises gene transcription.

418. The method of clause 406, any other suitable clause, or any combination of suitable clauses, wherein the protein-protein interaction comprises CAR expression.

419. The method of clause 404, any other suitable clause, or any combination of suitable clauses, wherein the intrabody composition is configured to control binding of an antigen to an antibody via activation.

420. The method of clause 404, any other suitable clause, or any combination of suitable clauses, wherein the intrabody composition is configured to induce protein homodimerization via activation.

421. The method of clause 404, any other suitable clause, or any combination of suitable clauses, wherein the intrabody composition is configured to induce protein heterodimerization via activation.

422. The method of clause 404, any other suitable clause, or any combination of suitable clauses, wherein the intrabody is a monobody.

423. The method of clause 404, any other suitable clause, or any combination of suitable clauses, wherein the intrabody is a nanobody.

424. The method of clause 404, any other suitable clause, or any combination of suitable clauses, wherein the intrabody is a monobody that recognizes the SH2 domain of Abl.

425. The method of clause 424, any other suitable clause, or any combination of suitable clauses, wherein the monobody comprises an EF domain.

426. The method of clause 404, any other suitable clause, or any combination of suitable clauses, wherein the intrabody is a mCherry-specific nanobody.

427. The method of clause 426, any other suitable clause, or any combination of suitable clauses, wherein the mCherry-specific nanobody comprises an S3 loop.

428. The method of clause 404, any other suitable clause, or any combination of suitable clauses, wherein the insert is a protein or a protein fragment.

429. The method of clause 428, any other suitable clause, or any combination of suitable clauses, wherein the protein comprises a LOV2 fragment.

430. The method of clause 428, any other suitable clause, or any combination of suitable clauses, wherein the protein comprises a circularly permuted version of cpLOV2.

431. The method of clause 428, any other suitable clause, or any combination of suitable clauses, wherein the protein comprises acVHH.

432. The method of clause 428, any other suitable clause, or any combination of suitable clauses, wherein the protein comprises an acVHH variant.

433. The method of clause 428, any other suitable clause, or any combination of suitable clauses, wherein the protein comprises UniRapR.

434. The method of clause 404, any other suitable clause, or any combination of suitable clauses, wherein the intrabody composition comprises two inserts.

435. The method of clause 434, any other suitable clause, or any combination of suitable clauses, wherein the two inserts comprise a first insert and a second insert.

436. The method of clause 435, any other suitable clause, or any combination of suitable clauses, wherein the first insert and the second insert are the same.

437. The method of clause 435, any other suitable clause, or any combination of suitable clauses, wherein the first insert and the second insert are different.

438. The method of clause 435, any other suitable clause, or any combination of suitable clauses, wherein the first insert and the second insert both comprise a LOV2 fragment.

439. The method of clause 435, any other suitable clause, or any combination of suitable clauses, wherein the first insert and the second insert both comprise cpLOV2.

440. The method of clause 435, any other suitable clause, or any combination of suitable clauses, wherein the first insert and the second insert both comprise a circularly permuted version of cpLOV2.

441. The method of clause 435, any other suitable clause, or any combination of suitable clauses, wherein the first insert and the second insert both comprise acVHH.

442. The method of clause 435, any other suitable clause, or any combination of suitable clauses, wherein the first insert and the second insert both comprise an acVHH variant.

443. The method of clause 404, any other suitable clause, or any combination of suitable clauses, wherein the insert comprises two inserts.

444. The method of clause 443, any other suitable clause, or any combination of suitable clauses, wherein the two inserts are contacted via a linker.

445. The method of clause 443, any other suitable clause, or any combination of suitable clauses, wherein the two inserts are covalently connected.

446. The method of clause 443, any other suitable clause, or any combination of suitable clauses, wherein the two inserts are covalently connected via a linker.

447. The method of clause 404, any other suitable clause, or any combination of suitable clauses, wherein the intrabody composition is conjugated to a therapeutic agent.

448. The method of clause 447, any other suitable clause, or any combination of suitable clauses, wherein the therapeutic agent is a CAR-T cell.

449. The method of clause 447, any other suitable clause, or any combination of suitable clauses, wherein the therapeutic agent is an NK cell.

450. The method of clause 447, any other suitable clause, or any combination of suitable clauses, wherein the therapeutic agent is a macrophage.

451. The method of clause 447, any other suitable clause, or any combination of suitable clauses, wherein the therapeutic agent is an antibody.

452. The method of clause 447, any other suitable clause, or any combination of suitable clauses, wherein the therapeutic agent is an E3 ligase.

453. The method of clause 447, any other suitable clause, or any combination of suitable clauses, wherein the therapeutic agent is a TEV protease.

454. The method of clause 447, any other suitable clause, or any combination of suitable clauses, wherein the therapeutic agent is transcriptional activator VP64.

455. The method of clause 404, any other suitable clause, or any combination of suitable clauses, wherein the intrabody composition comprises SEQ ID NO:1.

456. The method of clause 404, any other suitable clause, or any combination of suitable clauses, wherein the intrabody composition consists essentially of SEQ ID NO:1.

457. The method of clause 404, any other suitable clause, or any combination of suitable clauses, wherein the intrabody composition consists of SEQ ID NO:1.

458. The method of clause 404, any other suitable clause, or any combination of suitable clauses, wherein the intrabody composition comprises SEQ ID NO:2.

459. The method of clause 404, any other suitable clause, or any combination of suitable clauses, wherein the intrabody composition consists essentially of SEQ ID NO:2.

460. The method of clause 404, any other suitable clause, or any combination of suitable clauses, wherein the intrabody composition consists of SEQ ID NO:2.

461. The method of clause 404, any other suitable clause, or any combination of suitable clauses, wherein the intrabody composition comprises SEQ ID NO:3.

462. The method of clause 404, any other suitable clause, or any combination of suitable clauses, wherein the intrabody composition consists essentially of SEQ ID NO:3.

463. The method of clause 404, any other suitable clause, or any combination of suitable clauses, wherein the intrabody composition consists of SEQ ID NO:3.

464. The method of clause 404, any other suitable clause, or any combination of suitable clauses, wherein the intrabody composition comprises SEQ ID NO:4.

465. The method of clause 404, any other suitable clause, or any combination of suitable clauses, wherein the intrabody composition consists essentially of SEQ ID NO:4.

466. The method of clause 404, any other suitable clause, or any combination of suitable clauses, wherein the intrabody composition consists of SEQ ID NO:4.

467. The method of clause 404, any other suitable clause, or any combination of suitable clauses, wherein the intrabody composition comprises SEQ ID NO:5.

468. The method of clause 404, any other suitable clause, or any combination of suitable clauses, wherein the intrabody composition consists essentially of SEQ ID NO:5.

469. The method of clause 404, any other suitable clause, or any combination of suitable clauses, wherein the intrabody composition consists of SEQ ID NO:5.

470. The method of clause 404, any other suitable clause, or any combination of suitable clauses, wherein the intrabody composition comprises SEQ ID NO:6.

471. The method of clause 404, any other suitable clause, or any combination of suitable clauses, wherein the intrabody composition consists essentially of SEQ ID NO:6.

472. The method of clause 404, any other suitable clause, or any combination of suitable clauses, wherein the intrabody composition consists of SEQ ID NO:6.

473. The method of clause 404, any other suitable clause, or any combination of suitable clauses, wherein the intrabody composition comprises SEQ ID NO:7.

474. The method of clause 404, any other suitable clause, or any combination of suitable clauses, wherein the intrabody composition consists essentially of SEQ ID NO:7.

475. The method of clause 404, any other suitable clause, or any combination of suitable clauses, wherein the intrabody composition consists of SEQ ID NO:7.

Example 1

Preparation of Caffeine-Operated Intrabody Compositions
Molecular Cloning and Plasmid Construction:

Plasmid construction was performed using the general restriction enzyme digestion and ligation method in Examples 1-4. KOD Hot Start DNA polymerase was purchased from EMD Millipore (Burlington, MA, USA) and used for PCR amplifications. Oligonucleotides were synthesized by Sigma Aldrich (St. Louis, MO, USA). The T4 DNA ligase kit and NEBuilder HiFi DNA Assembly Master Mix were purchased from New England BioLabs (Ipswich, MA, USA). QuikChange Multi Site-Directed Mutagenesis Kit was obtained from Agilent Technologies (Santa Clara, CA, USA). Recombinant SARS-COV-2 Spike RBD was purchased from R&D Systems (Minneapolis, MN, USA).

YFP-acVHH-PB was generated by inserting the synthesized cDNA encoding acVHH (GENEWIT, South Plainfield, NJ, USA) upstream of the STIM1-PB domain into the pEYFP-C1 vector. To produce oligomeric proteins fused to PB, acVHH or YFP was replaced by mCherry, GST, DsRed and the FRB/FKBP system, respectively. YFP-acVHH-PB variants were made by using the QuikChange Site-Directed Mutagenesis Kit. YFP-biCOSMO-S—PB and YFP-bi-COSMO-L-PB were constructed by inserting amplified acVHH-Y104W with the corresponding linker into YFP-COSMO-PB. mCherry-acVHH (WT/Y104W)-STIM1ct constructs were prepared by amplifying the STIM1ct fragment (233-685) and acVHH (WT/Y104W) via standard PCR and then inserted into a modified pmCherry-C1 vector. Lyn11-mCh-FGFRct-COSMO was constructed by amplifying cDNAs encoding Lyn11, FGFRct and acVHH-Y104W and then inserting them individually into a pTriEx vector. Bacterial expression vectors encoding MBP-COSMO-H11-D4 and MBP-COSMO-VHH72 were made by amplifying acVHH-Y104W and synthetic cDNAs encoding H11-D4 or VHH72 and inserting them into the pMCSG-9 vector, respectively. $MLKL_{NT}$-mCh-biCOSMO-S was constructed by inserting amplified biCOSMO-S into the pLentiBlast vector. biCOSMO-L-SpvB was constructed by sequentially inserting amplified SpvB N- (residues 375-462), biCOSMO-L and SpvB C-domain (residues 463-591) into the pEGFP-C1 vector.

Chemical Reagents and Caffeinated Beverages:

Caffeine, paraxanthine, theobromine, rapamycin, Isopropyl-b-D-thiogalactopyranoside (IPTG), DMSO, and theophylline were purchased from Sigma. DMSO stock solution was made refresh prior to use. Annexin V (Pacific Blue™ conjugate) was purchased from Fisher Scientific. Caffeinated beverages, including Coca-Cola, Starbucks coffee and Red Bull were purchased from a local grocery store.

Cell Culture and Transfection:

The HeLa cell line was purchased from ATCC. Cells were cultured at 37° C. with 5% $CO_2$ in Dulbecco's Modified Eagle medium (DMEM; Sigma-Aldrich; St. Louis, MO, USA) supplemented with 10% FBS and 1% penicillin/streptomycin cocktail. For fluorescence imaging experiments, cells were seeded in 35-mm glass-bottom dishes (Cellvis, Mountain View, CA, USA). On day 2, transfection was performed when cells reaching about 50-70% confluency using the Lipofectamine 3000 (Life Technologies; Carlsbad, CA, USA) reagent by following the manufacturer's instructions. 6 h post-transfection, cells were replenished with normal DMEM. On day 3-4, transfected cells were mounted on a Nikon confocal microscope stage for imaging.

Highthroughput Screening (HTS) of acVHH Variants:

Randomized mutagenesis in key sties involved in caffeine binding were performed and the formation of dimeric interface by using acVHH as the template (a total of 27 sites× 20=540 constructs; FIG. 1). The PM-translocation of acVHH-PB variants was used as a readout for high-content imaging. HeLa cells were seeded in a glass-bottom 96-well microplate (Cellvis, Mountain View, CA, USA) at a density of $1\times10^4$ cells/well and cultured in 40 μL DMEM supplemented with 10% FBS in 5% $CO_2$ at 37° C. 12 hours later, the constructed plasmids were transfected into HeLa cells with Lipofectamine 3000. After 18 hours, the microplate was mounted on the IN Cell Analyzer 6000 (GE) high-content imaging instrument in the absence of caffeine and performed fast imaging with four captured views per well. Next, the microplate was incubated with caffeine (1 μM) for 10 min and re-imaged using the same parameters. The exported florescent images were then analyzed with an Image J PathFinder plugin for automated membrane detection and quantification. The screened top candidate mutations were further characterized by titration with increasing doses of caffeine to obtain the $EC_{50}$ cures in living cells. The PM/Cytosol ratios were quantified and plotted against the dosest o obtain the apparent binding affinity.

Purification of Recombinant Proteins from E. coli:

Escherichia coli strain BL21(DE3) cells (EMD Millipore) were transformed with plasmids encoding MBP-COSMO-VHH72 and MBP-COSMO-H11-D4, and grown at 37° C. in LB medium. Protein expression was induced by the addition of 0.5 mM IPTG when OD600 around 0.6-0.8, and incubated at 16° C. for another 16 h. Harvested cells were resuspended in a resuspension buffer containing 20 mM Tris-HCl pH 7.4, 137 mM NaCl, and then sonicated. The cellular debris was removed by centrifugation. The MBP-fusion protein was enriched by passing the clarified supernatants through amylose resin and further purified via size exclusion chromatography (GE Healthcare).

Live-Cell Imaging and Image Analysis:

Fluorescence imaging was performed on a Nikon Eclipse Ti-E microscope equipped with an A1R-A1 confocal module with LU-N4 laser sources (argon-ion: 405 and 488 nm; diode: 561 nm) and a live-cell culture cage (maintaining the temperate at 37° C. with 5% $CO_2$). 60× oil or 40× oil lens was used for confocal imaging. The half maximal effective concentration ($EC_{50}$) values of acVHH and COSMO variants were determined by incubating Hela cells with DMEM media containing various concentrations of caffeine, its metabolites, or caffeinated beverages for 2 min. To calculate the changes in cytosolic YFP signals (in the form of $F/F_0$), the "Intensity Line Profile" function in the Nikon Elements software was employed. The titration curves were fitted using a dose-response curve function ([Agonist] vs. response—Variable slope (four parameters)) using the Prism8 software. 16 cells were selected for each titration curve. All experiments were independently repeated three times.

For measurement of Ca2+ influx in HeLa cells co-expressing the green calcium indicator GCaMP6s and mCherry-acVHH/COSMO-STIM1ct, 488-nm and 561-nm laser sources were used to excite GFP and mCherry, respectively, at an interval of 8 sec. The collected images were analyzed by the NIS-Elements AR microscope imaging software (Nikon, NIS-element AR version 4.0). 40-60 cells were selected to define regions of interest (ROI) for analyzing the GCaMP6s fluorescence intensity. All experiments were repeated three times. To monitor NFAT-GFP nuclear translocation, a HeLa cell line stably expressing $NFAT1_{1-460}$-GFP was used. mCherry-acVHH/COSMO-STIM1ct were transfected into this cell line, which was imaged 24 h after transfection. A total of 60 min time-lapse imaging was recorded at an interval of 15 sec and the nuclear GFP signal ratio changes (in the format of $F/F_0$) were used to report the efficiency of NFAT activation. At least 40 cells were analyzed for each condition in three independent experiments.

To monitor the necroptosis of HeLa cells transfected with $MLKL_{NT}$-mCherry-diCOSMO-S, 405 nm and 561 nm laser sources were used to excite Pacific blue-conjugated Annexin V and mCherry, respectively. Hela cells were preincubated with the Annexin V staining reagent for 5 min before imaging, and 100 μM caffeine was added to the medium to reach a final concentration of 1 μM during the imaging process. Time-lapse imaging was carried out at an interval of 1 min for up to 100 min and the blue signal ratio change of Annexin V ($F/F_0$) was used to quantitatively report the necroptotic progression.

Enzyme-Linked Immunosorbent Assay (ELISA) to Probe the Nanobody-RBD Interaction:

Wells of microtiter plates were coated overnight at 30° C. with 30 ng streptavidin. Biotinylated SARS-COV-RBD was added and incubated at 4° C. for 4 hours. The coated plates were then blocked with 5% BSA in PBS. Serially diluted nanobodies (20, 10, 5, 2.5, 1.25, 0.63, 0.31, 0.06, 0.006 µg/mL) were added to the individual wells. Binding was detected by incubating the plates sequentially with a mouse anti-MBP monoclonal antibody (E8032S, New England Biolabs) and a horseradish peroxidase (HRP)-linked anti-mouse IgG (1/2000, NXA931, GE Healthcare). After washing, 30 µL of tetramethylbenzidine substrate (BD OptETA) was added to each well and the reaction was stopped by addition of 20 µL of 1 M $H_2SO4$. The absorbance (O.D.) at 450 nm was measured with an iMark Microplate Absorbance Reader (Bio-Rad).

Example 2

Characterization and Optimization of Caffeine-Operated Intrabody Compositions ("Caffeine-Operated Synthetic Module (COSMO)")

Figure 2A:
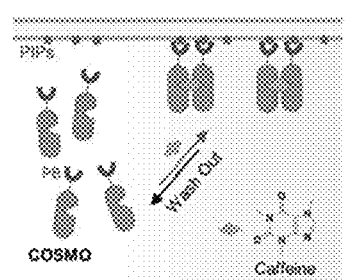
Figure 2B:
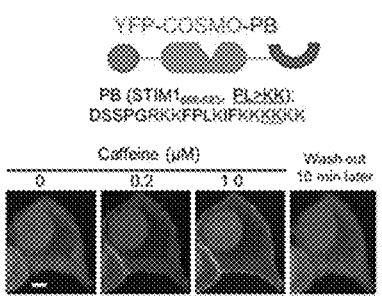

To facilitate the high throughput screening of acVHH variants with varying affinities to caffeine, a protein translocation assay was developed by fusing acVHH with a phosphoinositide (PIP)-binding (PB) domain derived from the stromal interaction molecule 1 (STIM1; aa 666-685; see FIG. 1 and FIGS. 2A-2B). The PB domain in a dimeric or multimeric form interacts with $PI(4,5)P_2$ and $PI(3,4,5)P_3$, two phospholipids that are abundantly enriched in the inner half leaflet of the plasma membrane (PM)[15]. Two mutations, P682K/L683K, were introduced to enhance the PIP-binding capability of the hybrid protein.

The cytosol-to-PM translocation of the modified PB domain can be initiated by light-inducible oligomerization. It is contemplated that the acVHH-PB hybrid protein stays in the cytosol in its monomeric form. Upon addition of caffeine, it is expected to observe its translocation toward PM due to dimerization of PB to increase its avidity toward PM-resident PIPs (see FIG. 2A). Indeed, when expressed in HeLa cells, a notable dose-dependent cytosol-to-PM translocation of YFP-acVHH-PB was observed upon addition of caffeine ($t_{1/2}$, on=29.4±1.6 s; see FIGS. 2B-2C). After withdrawal of caffeine, the PM-bound fraction of acVHH-PB returned to the cytosol with a deactivation half-life of 83.1±1.1 s (see FIGS. 2B-2C), clearly demonstrating the reversibility of this synthetic system.

The PM-translocation assay enabled us to screen acVHH mutants at real time in living cells to identify potent caffeine binders. Combined with site-directed mutagenesis, key residues were identified that would enhance the affinity of acVHH to caffeine. Mutagenesis was performed on residues located in close proximity to the caffeine binding pocket and at the VHH/VHH dimer interface area (see FIG. 1 and FIG. 2D). Among all the tested variants, Y104W was identified as the best construct, which displayed the highest degree of PM translocation upon addition of 200 or 1000 nM caffeine, and hence renamed as caffeine-operated synthetic module (COSMO). Mutations introduced in other positions (e.g., Y34, Y61, M63, Y108, and W111) tend to reduce or even abrogate caffeine-inducible PM translocation (see FIGS. 2D-2F and FIGS. 3A-3C).

Figure 4A:
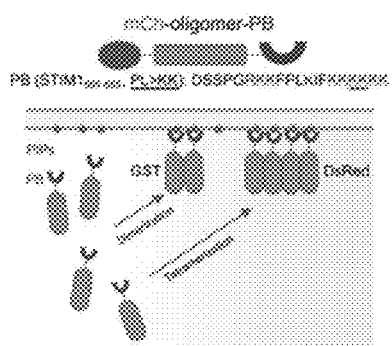
Figure 4B:
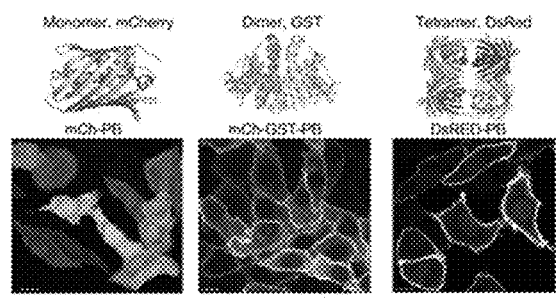
Figure 4C:
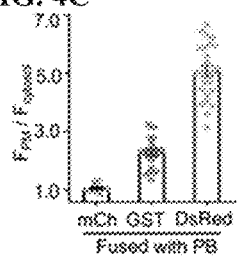
Figure 4D:
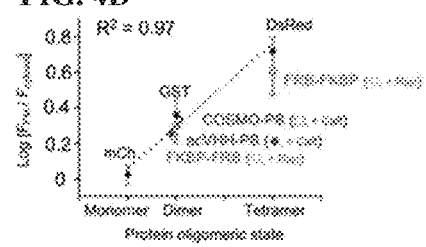

To probe the oligomeric state of WT acVHH and COSMO under physiological conditions in cellulo rather than using artificial recombinant proteins in vitro, a mini-tagging approach was utilized by replacing the microtubule binder in MoTag with the modified STIM1-PB tag (see FIGS. 4A-4E). To establish a calibration curve for assessing protein oligomeric states in live cells, the PB domain was fused with well-known oligomeric proteins (monomeric mCherry, dimeric GST and tetrameric DsRed) and their localization was examined using confocal microscopy (see FIG. 4B). The degree of PM translocation showed a positive correlation with the protein oligomeric states (FIGS. 4A-4E). The use of the PB tag to determine protein oligomeric states was further validated by rapamycin inducible dimerization (FKBP-FRB fusion) and tetramerization (FRB-FKBP fusion) systems (FIGS. 4D-4E). As a result, the PB-tagging method can be applied to quantitatively discriminate proteins assembled as monomer, dimer, or tetramer in single cells (see FIG. 4D). When the similar method was extended to analyze acVHH and COSMO, both proteins seemed to exist as dimer in the presence of caffeine (see FIG. 2F and FIG. 3C).

Figure 2C:
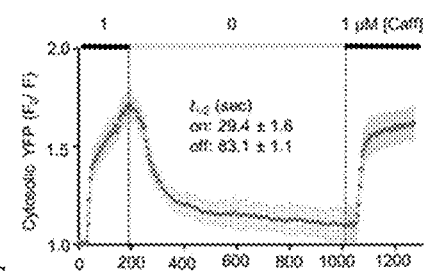

The PM-translocation assay provides quantitatively probing the strengths of caffeine binding to the engineered acVHH variants in living cells. Caffeine was titrated into HeLa cells expressing YFP-acVHH-PB variants (as shown in FIG. 2C) and used the PM-to-cytosol ratio of fluorescent signal as a sensitive readout. WT acVHH showed an apparent $EC_{50}$ value of 567.5 nM (FIG. 2G), which is comparable to the dissociation constant ($K_d$=500 nM) determined in aqueous solutions using purified protein. By contrast, COSMO (Y104W-acVHH) showed a higher affinity to caffeine with the $EC_{50}$ enhanced by ~6-fold (95.1 nM; see FIG. 2G). Table 2 further shows this result.

TABLE 2

Summary of caffeine sensitivity ($EC_{50}$ values) for representative acVHH variants and biCOSMO variants tested in the study.
n = 16 cells from three independent assays

| Variants | $EC_{50}$ |
|---|---|
| WT | 567.5 ± 1.6 nM |
| Y104W (COSMO) | 95.1 ± 1.2 nM |
| Y104F | 3990.2 ± 4.7 nM |
| Y34W | >20 µM |
| Y34F | No binding |
| Y108W | >2 µM |
| Y108F | No binding |
| Y61W | >1 µM |
| Y61F | No binding |
| F39W | No binding |
| F39Y | No binding |
| W111F | No binding |
| W111Y | No binding |
| M63L | No binding |
| biCOSMO-S | 16.9 ± 2.0 nM |
| biCOSMO-L | Intramolecular binding |
| 2x WT acVHH-S | 530.9 ± 1.6 nM |

Figure 2D:
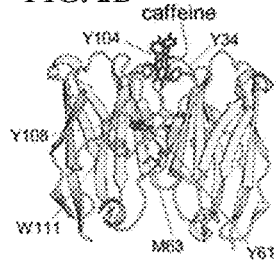
Figure 2E:
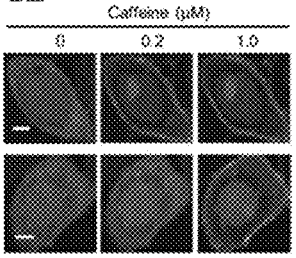
Figure 2F:
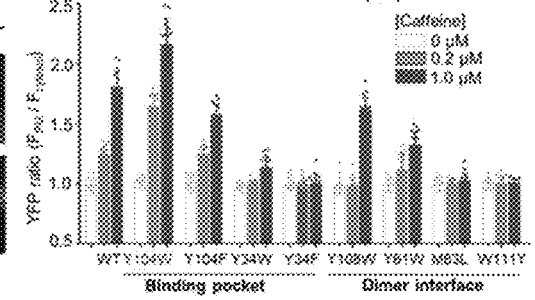
Figure 5:
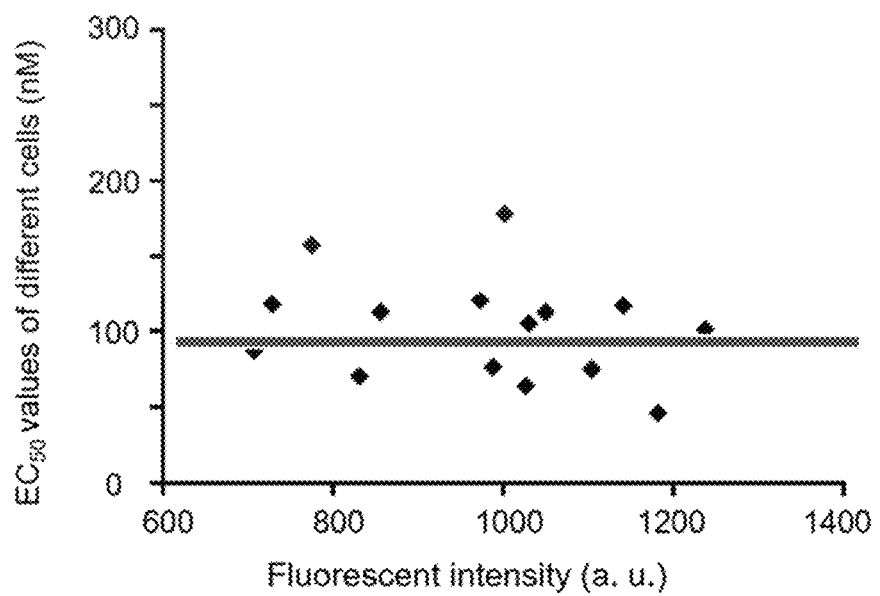
FIG. 5 shows $EC_{50}$ values obtained from 15 individual cells expressing various levels of COSMO (indicated by fluorescence intensity of the YFP tag). The red line indicates the averaged $EC_{50}$ value of COSMO for caffeine (95.1 nM). No significant concentration-dependent effect was observed.

Moreover, the $EC_{50}$ value of COSMO was largely unaffected by its expression level when expressed in mammalian cells (FIG. 5). In the 3D structure of a caffeine-bound dimeric acVHH complex, two Y104 residues from neighboring acVHH molecules are situated right above caffeine to form a "cap" (FIG. 2D). A water molecule seems to stabilize the cap and prevent the escape of bound caffeine via formation of hydrogen bonds (FIG. 3A). The Y-to-W replacement could still preserve the hydrogen bonds considering the H-bond forming ability of its aromatic (φ) ring with the OH group of the water. (FIG. 3A).

In support of this view, the Y-to-F substitution, which led to a complete loss of H-bonds in the aromatic cap, resulted in great loss in $EC_{50}$ (3990.2 nM vs 567.5 nM; see FIG. 2G and Table 2). Meanwhile, the π-π stacking interaction between Y34 and the sandwiched caffeine appeared to be essential for acVHH dimerization as replacement of Y34 with F or W substantially suppressed or abrogated the caffeine-induced effect (see FIG. 2G, FIG. 3B, and Table 2).

Considering that caffeine can be metabolized in the liver of mammals into paraxanthine (84%), theobromine (12%), and theophylline (4%)[21] and that WT acVHH shows weak or no appreciable binding to these metabolites, it was evaluated if COSMO could respond to these chemicals and thus expand its effective substrate scope. The results demonstrated that COSMO exhibited 41~217-fold enhancement in $EC_{50}$ toward the three major caffeine metabolites when compared to WT acVHH (see FIG. 2H). Given the relatively large gap in the binding strengths between caffeine and its metabolites (over 25-fold difference), caffeine can achieve specific activation of COSMO in the range of 10-100 nM (see FIG. 2H and FIG. 6A-6C). Under this low dose, COSMO remained largely inert to caffeine metabolites and analogs.

Figure 7A:
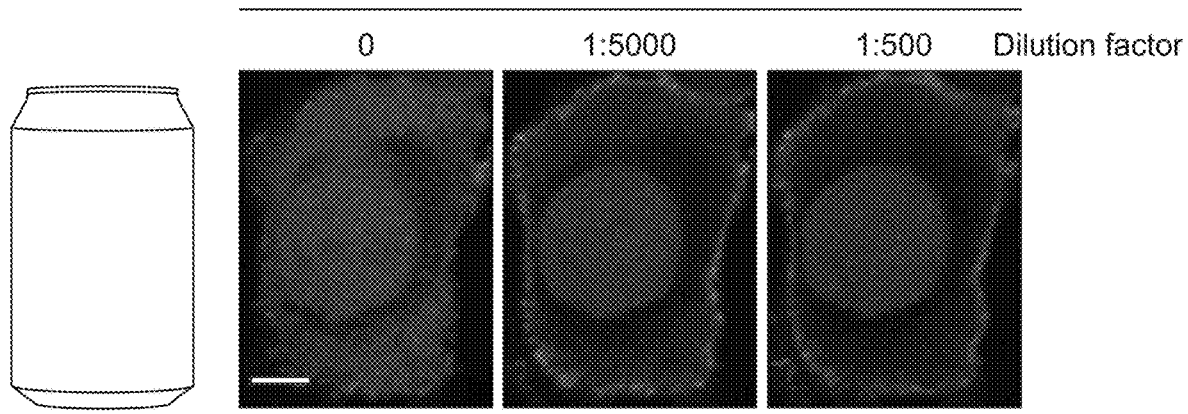
FIGS. 7A-7C show PM translocation of YFP-COSMO-PB induced by exemplary caffeinated beverages. Shown were representative confocal images of HeLa cells expressing YFP-COSMO-PB (green) before and after incubation with the indicated caffeine-containing beverages (FIG. 7A=Coca-Cola.
Figure 7B:
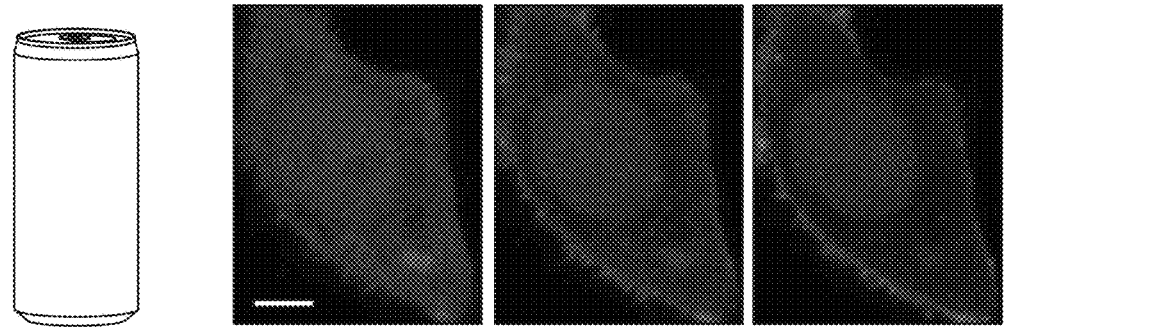
Figure 7C:
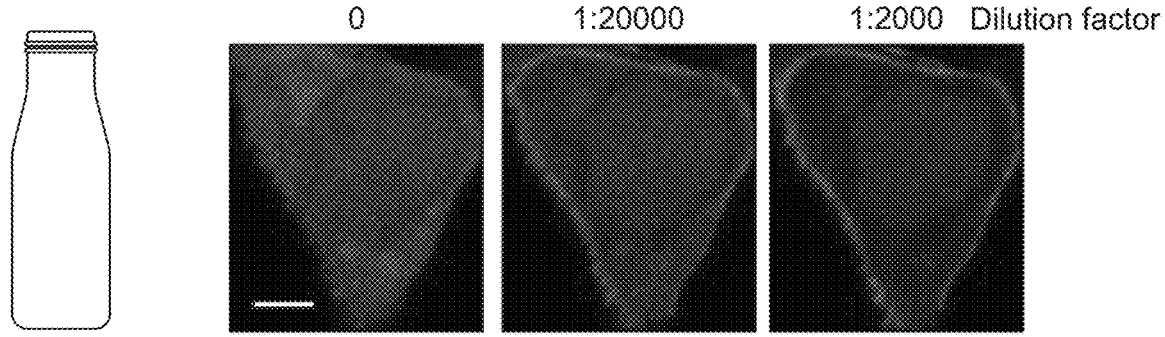
Figure 12:
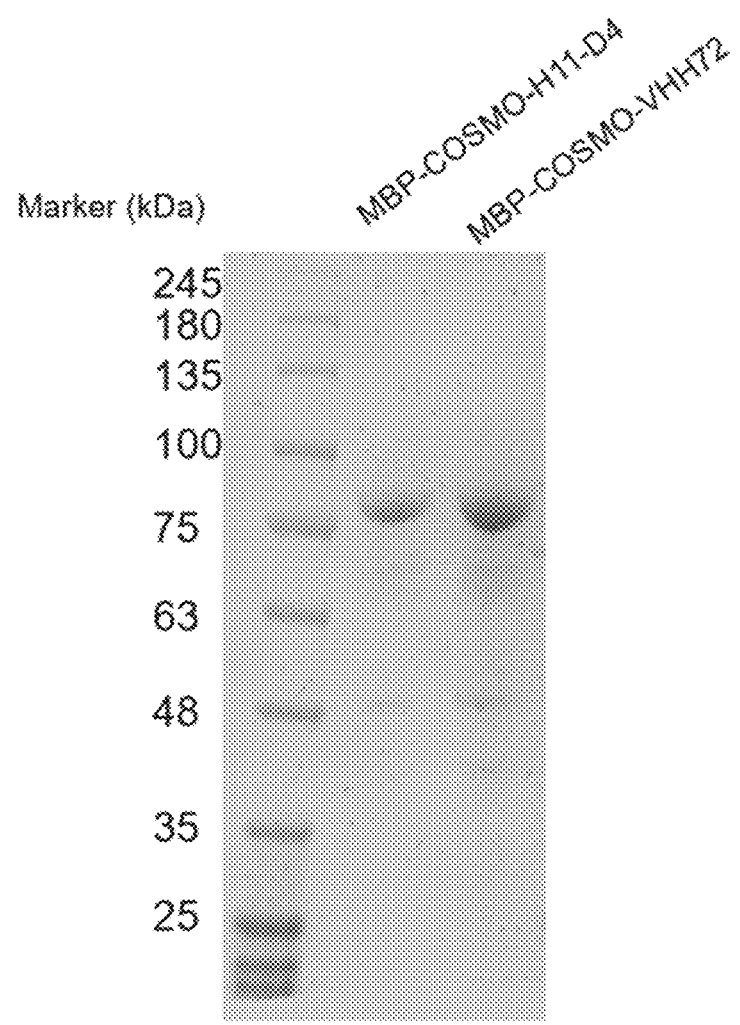
FIG. 12 shows SDS-PAGE analysis of purified MBP-COSMO-H11-D4 and MBP-COSMO-VHH72. The calculated molecular weights of both proteins are approximately 76 kDa.

Thereafter, commercially available caffeinated beverages were evaluated, including coffee, Red Bull and Coca-Cola (see FIGS. 7A-7C). In HeLa cells incubated with diluted beverages, a dose-dependent, cytosol-to-PM translocation of YFP-COSMO-PB even at a dilution factor of 1:20,000 was observed (see FIGS. 7A-7C).

Collectively, through rationalized mutagenesis and screening, COSMO is shown to be as a potent genetically-encoded synthetic module that can be used to control protein homodimerization using caffeine, caffeine metabolites, and a range of consumer caffeinated beverages.

Example 3

Application of COSMO as Chemically-Inducible Dimerizer

The instant example evaluates the feasibility of using COSMO as a chemically-inducible dimerizer. For instance, a synthetic device can be designed that can use low dose caffeine to switch on the ORAI calcium channel and control the downstream calcium-responsive transcription factor, the nuclear factor of activated-T cells (NFAT). As forced dimerization of the N-terminus of the cytoplasmic domain of stromal interaction molecule 1 (STIM1ct) has been shown to switch on autoinhibitory STIM1 to engage and activate ORAI calcium channels, it is hypothesized that caffeine-inducible dimerization of STIMIct could likewise achieve the same function (see FIG. 8A).

An acVHH-STIMIct hybrid construct was formed but did not show pronounced caffeine-induced calcium influx in HeLa cells incubated with 1 μM caffeine (see FIG. 9A). After replacing acVHH with COSMO, a robust calcium influx was detected with an activation half-life of 97.8±2.4 s as well as a notable co-localization of COSMO-STIMIct with PM-embedded ORAI1 channels in the presence of caffeine (FIGS. 8B-8D), thus indicating the functional coupling between engineered STIM1 and ORAI1.

Sustained $Ca^{2+}$ influx can further activate a $Ca^{2+}$-dependent phosphatase, calcineurin, and subsequently dephosphorylate the calcium-responsive NFAT to cause its nuclear translocation. Thus, the degree of NFAT nuclear localization was compared before and after caffeine treatment. In agreement with the calcium influx data, caffeine caused efficient shuttling of cytosolic NFAT into the nuclei in all cells expressing COSMO-STIMIct within 30 min ($t_{1/2}$=17.1 min; see FIG. 8E), but not in those transfected with acVHH-STIM1ct (see FIG. 9B). Taken together, these data establish COSMO as a more efficient and potent CID system compared to WT acVHH.

Additional intrabody compositions were constructed. For instance, PM-resident tyrosine receptor kinases (RTKs) were engineered aiming to use caffeine to replace growth factors to recapitulate RTK-mediated intracellular signaling. The COSMO module was fused with cytoplasmic region of fibroblast growth factor receptor 1 (FGFRct) and tethered the hybrid protein toward PM via N-terminal tagging with the Lyn11 motif (see FIG. 10A). It is contemplated that dimerization of FGFRct induced by caffeine could bring two FGFRct molecules into close proximity and subsequently activate this receptor similarly to its natural ligand FGF. To monitor FGFR signaling at real time in living cells, three hallmark downstream signals were assessed (see FIG. 10A): intracellular $Ca^{2+}$ rise due to phospholipase C activation (GCaMP6s as reporter), PIP3 synthesis in the PM because of phosphoinositide 3-kinaes (PI3K) activation ($PH_{AKT}$-GFP as sensor for PIP3), and the nuclear accumulation of the extracellular signal-regulated kinase (ERK). Following the addition of caffeine, a robust increase in intracellular Ca2+ was observed as reflected by the over 3-fold enhancement of GCaMP6s fluorescence within seconds in Hela cells expressing Lyn11-mCh-FGFRct-COSMO (see FIGS. 10B-10C). Caffeine-triggered calcium mobilization could be further employed to inducibly drive the expression of genes of interest (e.g., GFP as reporter) by taking advantage of synthetic $Ca^{2+}$-sensitive transcriptional response elements derived from NFAT, serum response factor (SRF) and cAMP response element-binding protein (CREB) (see FIGS. 10D-10E). Meanwhile, time-lapse live cell imaging further showed that two additional downstream effectors, PI3K and ERK, were both activated within 5-10 minutes, which were reported by the cytosol-to-PM translocation of a PIP3 sensor $PH_{AKT}$-GFP (see FIGS. 10F-10G) and the nuclear translocation of ERK-GFP (see FIGS. 10H-10I). Collectively, the compatibility of COSMO with membrane-bound signaling receptors to rewire RTKs-mediated cell signaling with caffeine was established, thus obviating the use of pleotropic growth factors that tend to cause crosstalks among various RTKs.

Figures 11A, 11B, 11C:
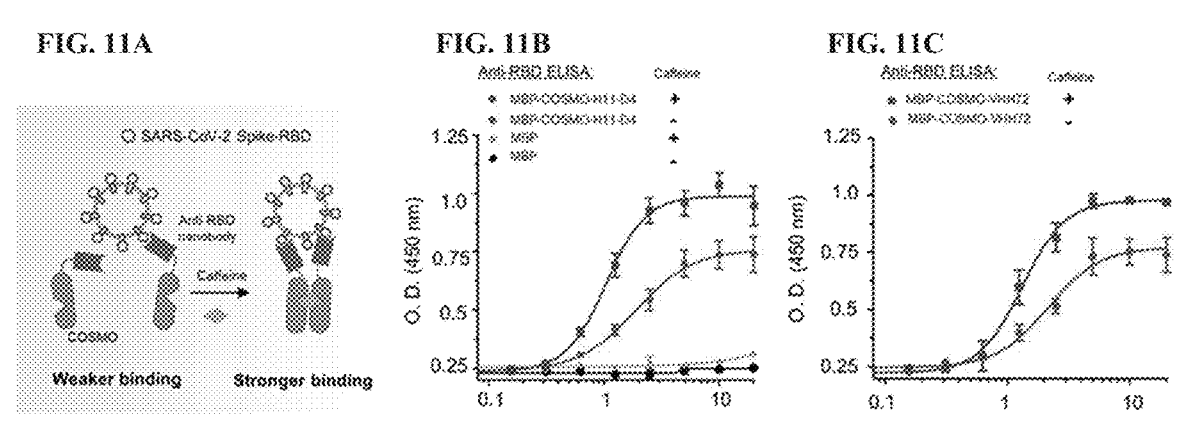

Thereafter, it was contemplated that COSMO can be modularly tagged to nanobodies that lack the bulky Fc fragment of a typical antibody, and enable the assembly of non-covalent bivalent nanobodies to enhance their antigen recognition. COSMO was fused with two different nanobodies (VHH72 and H11-D4) that could specifically recognize the receptor binding domain (RBD) of the spike protein derived from severe acute respiratory distress (SARS) coronavirus 2 (SARS-COV-2). These nanobodies have the potential to mitigate SARS-CoV-2 infection and alleviate COVID-19 symptoms by blocking the interaction of viral spike protein with the angiotensin-converting enzyme 2 (ACE2) expressed on the surface of human lung epithelial cells. Use of a covalently linked bivalent nanobody or fusion with the Fc homodimerization fragment could enhance the nanobody-target interaction and virus neutralization capability. Thus, it was evaluated whether chemical-inducible dimerization of these nanobodies could exhibit similar boosting effects (see FIG. 11A).

After screening several anti-Spike nanobodies fused with COSMO, it was shown that COSMO-H11-D4 and COSMO-VHH72 showed stronger binding to SARS-COV-2 RBD in the presence of 10 μM caffeine based on ELISA results (see FIGS. 11B-11C FIG. 4b, 4c and FIG. 12). Their apparently binding affinities were improved by 1.8 and 1.6 fold, respectively (COSMO-H11-D4: 25 nM versus 14 nM; COSMO-VHH72: 29 nM versus 18 nM). Thus, chemical induced dimerization could be exploited to enhance the binding strength of nanobodies against the SARS-COV-2 spike protein, which promises to be more effectively neutralize the virus infectivity.

Example 4

COSMO Concatemer (biCOSMO) as Modular Switch to Control Protein Activities

COSMO exhibits a low $EC_{50}$ to caffeine (95.1 nM) and greatly expands its substrates. In the instant example, COSMO was assembled in a concatemeric form with linkers of different lengths (see FIG. 13A) to generate a more potent COSMO-based system. Screening the 2×COSMO-PB (biCOSMO-PB) constructs with 0.2 and 1 µM caffeine demonstrated that two copies of WT acVHH covalently connected with short flexible linkers (L1-L3) exhibited stronger cytosol-to-PM translocation (FIG. 14). However, the same linkers grafted into COSMO led to pre-dimerization of biCOSMO-PB, as reflected by noticeable PM decoration in the absence of caffeine. It was contemplated that limiting the flexibility of bivalent COSMO using a more rigid linker would provide benefits. Therefore, an 11-mer sequence derived from the coiled-coil 1 (CC1) domain of STIM1 (residues L251 to L261) was used, which has a strong helical propensity and adopts a helical structure (FIG. 14).

Figure 13A:
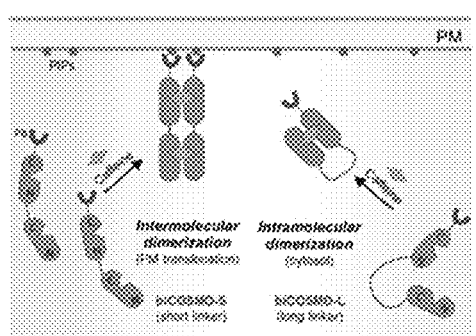
Figure 13B:
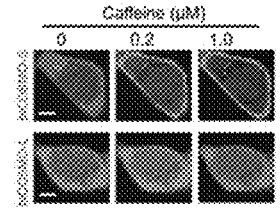
Figure 13C:
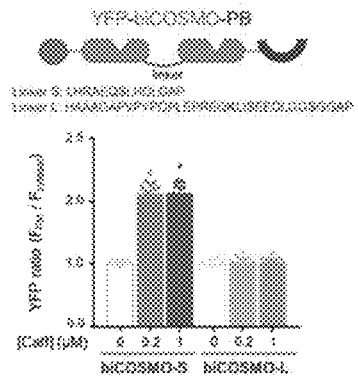

The resultant intrabody composition ("biCOSMO-S") subsantially reduced basal activity, as shown by the lack of discernible PM translocation of biCOSMO-PB (see FIGS. 13B-13C). More importantly, the caffeine sensitivity was improved by over 30-fold compared to WT acVHH ($EC_{50}$: 16.9 nM vs 567.5 nM; see FIG. 13D and Table 2).

Construction of a similar concatemer using WT acVHH with the same linker (2×acVHH-S-PB) showed slight improvement in the performance compared to acVHH-PB (530.9 nM vs 567.5 nM; see Table 2), which demonstrates the unique COSMO module to enhance the binding affinity. Surprisingly, use of a longer linker with a mixed flexible and rigid structure to connect two COSMO molecules (biCOSMO-L-PB), demonstrated that caffeine-induced PM translocation was no longer observed (see FIGS. 13B-13D). Thus, biCOSMO-L-PB may favor an intramolecular dimerization (as seen in UniRapR14) instead of intermolecular dimerization as seen with biCOSMO-S(FIG. 13A).

Figure 13E:
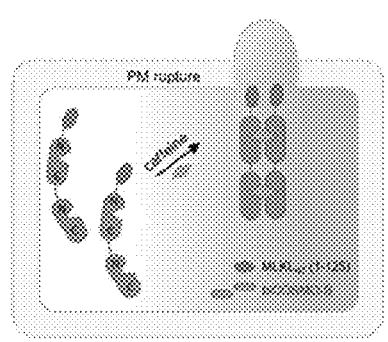
Figure 13F:
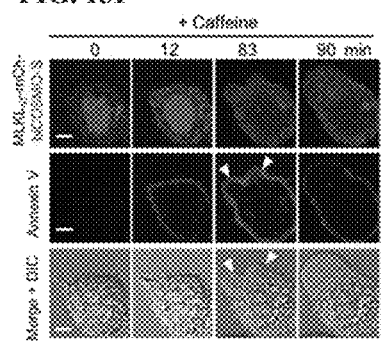
Figure 13G:
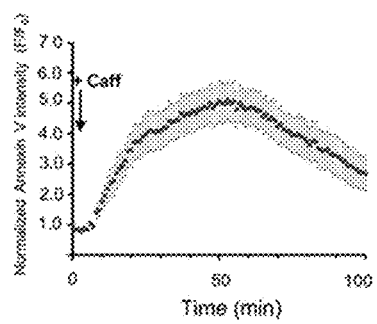

To further validate that biCOSMO-S could be harnessed to induce intermolecular dimerization, a chemically-inducible cell suicide device was developed by fusing biCOSMO-S with the N-terminal domain of MLKL ($MLKL_{NT}$). Once activated via phosphorylation upon inflammatory stimulation, the N-terminal region of MLKL can to oligomerize and translocate toward the PM to perforate membrane and cause necroptosis, a new form of non-apoptotic cell death. It is contemplated that caffeine-inducible dimerization of $MLKL_{NT}$-biCOSMO-S could similarly trigger necroptosis but obviate the need of detrimental necroptotic stimuli (FIG. 13E). Upon caffeine treatment, translocation of $MLKL_{NT}$-mCh-biCOSMO-S from the cytosol toward the PM was observed, accompanied with positive staining for Annexin V (cell death indicator) and ultimate necroptotic bubble formation and PM rupture (see FIGS. 13F-13G). Collectively, these findings demonstrate biCOSMO-S as a potent chemically-inducible dimerizer that can be used to kill cancer cells within hours.

Finally, biCOSMO-L was evaluated as a modular allosteric switch to control enzymatic activity. The ADP-ribosyl-transferase (ATR) domain derived from *Salmonella* SpvB, a bacterial enzyme that catalyzes ADP ribosylation of actin to prevent actin polymerization was engineered (FIG. 15A). As such, biCOSMO-L was inserted into a flexible loop region connecting the N- and C-domains of SpvB (FIG. 15B), hypothesizing that the addition of caffeine would induce the reassembly of a functional SpvB to restore its function to disrupt actin cytoskeleton (FIG. 15A). In HeLa cells transfected with EGFP-biCOSMO-L-SpvB, both EGFP-negative and EGFP-positive cells showed strong staining of actin polymers by fluorophore-conjugated phalloidin in the absence of caffeine (FIG. 15C). However, upon incubation with caffeine, a substantial reduction or disappearance of actin labeling by rhodamine-phalloidin staining in EGFP-positive cells was observed (see FIGS. 15C-15D). This suggests that caffeine restored the SpvB enzymatic activity to antagonize actin polymerization. This effect was very specific since EGFP-negative cells without expression of the hybrid construct in the same imaging field still retained strong actin labeling (FIG. 15C). In sum, biCOSMO-L can be used as a caffeine-controllable switch to control the disassembly actin cytoskeleton.

Compared to other commonly used CID systems (Table 3), desirable features of the COSMO platform include: (i) the least chemical complexity and smallest size of the ligand (194 Da; FIG. 16); (ii) a single-component system with a compact size (only 118 residues for COSMO); (iii) low cost and easy accessiblity from daily-cosume beverages and food; (iv) excellent bioavailability and compatibility with multiple routes of administration; and (iv) good reversibility upon metabolism or withdrawl of ligand treatment.

TABLE 3

| System | EC50 (nM) | Time Scale (dimerization) | Ligand Price | Safety of Ligands | Reference (PMID) |
|---|---|---|---|---|---|
| COSMO/ Caffeine | 95.1 | <1 min | $40.9/100 g | Daily beverage <400 mg/day, adult | |
| biCOSMO-S/ Caffeine | 16.9 | <1 min | $40.9/100 g | Daily beverage <400 mg/day, adult | |
| FRB-FKBP/ Rapamycin | 10-20 | <2 min | $407/5 mg | Rapamycin is immunosuppressive agent | 15796538 31586989 |
| GAI-GID1/ GA3-AM | 310 | <1 min | $256/5 mg | Generally harmless | 22446836 |
| PYL-ABI/ ABA | >104 | >30 min | $26.8/50 mg | Orally available | 21406691 |
| HaloTag- | >103 | >10 min | Not | Unknown | 23601644 |

TABLE 3-continued

| System | EC50 (nM) | Time Scale (dimerization) | Ligand Price | Safety of Ligands | Reference (PMID) |
|---|---|---|---|---|---|
| SNAPTag/ HaXS | | | commercially available | | |
| FKBP'-eDHFR/ SLF'-TMP | 120 | <2 min | Not commercially available | No cytotoxicity toward COS-7 cells (up to a concentration of 50 mM) | 25065762 |

Moreover, by inserting a short rigid linker between two copies of COSMO, the half maximal effective concentration to the low nM range are further enhanced (comparable to the widely-used FKBP/FRB system), thereby providing an alternative option for chemogenetic applications. Most importantly, biCOSMO-L can be modularly inserted into a host protein to enable allosteric control of protein activities and achieve tailored function.

Example 5

Preparation of Light- and Chemical Operated Intrabody Compositions

Molecular Cloning and Plasmid Construction:

The restriction enzyme digestion-ligation and NEBuilder HiFi DNA Assembly methods were used to create plasmids in Examples 5-8. The KOD Start DNA polymerase (EMD Millipore, MA, USA) was used for PCR amplification. All the subcloned sequences were verified using diagnostic restriction digestion and Sanger's sequencing analysis. All the other cloning regents were purchased from New England Biolabs (Ipswich, MA, USA).

cDNA sequences encoding monobodies and nanobodies used in Examples 5-8 were codon-optimized and synthesized as gBlock by Integrated DNA Technologies (IDT Inc, IA, USA). The monobody-encoding cDNAs (SH2Abl, MBP and SUMO) were individually inserted into a customized pcDNA-mCherry vector between the EcoRI and XbaI restriction sites to generate mCh-tagged monobodies. To create a nuclear envelope (NE)-targeting SH2abl, cDNA of lamin A was inserted into a customized mEmerald-C1 vector, followed by SH2abl insertion (NheI-EcoRI). AsLOV2 fragments were PCR amplified and inserted into monobodies by using the NEBuilder HiFi DNA Assembly method. For photoswitchable degradation, moonbody (S5.1) cDNA was amplified via PCR and then inserted into the pSH-EFIRES-P-AtAFB2-mCherry vector (Addgene, #129716) between EcoRI and NotI sites to replace mCherry.

To make GFP fused nanobody, cDNA encoding the anti-mCherry nanobody LaM8 was cloned into the pTriEx-GFP vector between HindIII and XhoI sites to yield pTriEx-GFP-LaM8. AsLOV2 fragments were PCR amplified and inserted via NEBuilder HiFi DNA Assembly. The construct exhibiting the highest light-induced changes was designated as "sunbody" (S0+S3). The tandem sunbody expression vector (2×sunbody) was made by inserting one additional copy of sunbody into the pTriEx-GFP-sunbody plasmid. The Uni-RapR or a dimeric concatemer of acVHH (2×acVHH connected by a 58-mer GS rich linker) was inserted into the S3 site by using the same method to create rapabody or caffebody. To make mitochondria-targeting mCh, the cDNA sequences encoding human AKAP11-30 (flanked by NheI and BamHI) was inserted into mCherry-N1 to yield AKAP1-mCh. For ER anchored mCh, human SacI fragment (residues 521-587) was cloned into the pEGFP-C3 backbone by utilizing the EcoRI-KpnI restriction sites, followed by GFP replacement by mCh (between NheI and XhoI sites). The plasma membrane targeting mCh construct was made as AgeI-mCh-EcoRV-CAAX-XbaI in the same backbone.

To create a SolarFLARE system for light-inducible transcriptional activation, the TEV protease component (from Ca-FLARE (protease), Addgene #92214) was assembled into pTriEx-GFP-sunbody to yield GFP-sunbody-TEV. The mCh and LOV2-TCS (TEV cleavage site)-tetR-VP16 fragments (from Ca-FLARE (TF), Addgene, #92213) modules were fused into a pcDNA3.1(+) backbone to make PM-anchored mCh-LOV2-TCS-tetR-VP16. The TagBFP or MLKL expression cassette used in the SolarFLARE system was made by putting TagBFP cDNA or human MLKL-NT (1-182) (EcoRI/XbaI) under the control of a tight TRE promoter.

For photoactivatable cytosine base editor (paCBE), mCh and Cas9n (Cas9-D10A nickase) fragments were inserted into a pcDNA3.1(+) vector via HiFi assembly to make mCh-Cas9n (Part I). FNLSHiFi was replaced by GFP-sunbody in the pLenti-FNLSHiFi-P2A-Puro vector (Addgene, #136902) to make the APOBEC1-GFP-sunbody-UGI fusion construct (Part II). The luciferase-based GO system with sgRNA in the same vector was obtained from Addgene (pLenti-mU6-Luc2GO-PGK-Neo, Addgene #136905).

For the rapabody-regulated transcriptional activation system, rapabody-VP64 was made by gene fragments assembly. The TagBFP reporter was modified from pGL3-Basic-8×-gRNA-eGFP (Addgene, #60718), in which the TagBFP gene was put under the tight control of a minimal CMV promoter. The sgRNA targeting the upstream promoter of TagBFP reporter was obtained from Addgene (#60719).

To make a caffeine-controlled calcium entry and NFAT dependent luciferase reporter system, cDNAs encoding all the components were synthesized and then re-assembled to make mCh-STIMlct (residues 233-685)-IRES-caffebody-SITM1ct by using a customized pmCherry-N1 vector as the backbone.

Cell Culture and Transfection

HeLa and HEK293T (human embryonic kidney) cell lines were obtained from ATCC and cultured under 37° C. at a 5% CO2 atmosphere, and maintained in the Dulbecco's modified Eagle's media (DCell MEM, Sigma-Aldrich, St Louis, MO, USA), supplemented with 10% fetal bovine serum (FBS). DNA transfection was performed by using the Lipofectamine 3000 transfection reagent (Thermo Fisher Scientific, MA, USA) according to the manufacturer's instructions. For live cell fluorescence imaging experiments, cells were seeded in four-chamber 35-mm glass bottom dishes (D35C4-20-1.5-N, Cellvis, Mountain View, CA, USA) one day before transfection, and imaged 24-48 h after transfection in an imaging cage equipped with 5% CO2 with temperature set at 37° C.

Live Cell Photostimulation, Time-Lapse Imaging and Imaging Data Analysis

Time-lapse confocal imaging was performed on a Nikon A1R confocal module mounted onto an inverted Nikon Eclipse Ti-E body. The light sources came from a multi-line argon laser module containing 405, 488, 561 and 640 nm lasers. A live-cell imaging caged platform was used to maintain the temperature at 37° C. with 5% CO2 to keep cells healthy during the imaging process. A 10×, 20× air objective lens and 40× or 60× oil immersion objective lens were used for image acquisition.

To monitor light-induced F-body:antigen association or dissociation, HeLa cells seeded on glass-bottom dishes were co-transfected with the indicated plasmids shown in the figures. Confocal images were acquired 24-48 hours after transfection. The cells were imaged every 4 sec for 2 nmin unless otherwise noted. The 488-nm laser source to excite GFP was also used for photostimulation (with 1-5% output). To quantify fluorescent signals at selected areas, we used the region-of-interest (ROI) toolbox in Nikon NIS-Elements software to define the nuclear envelope (NE) or nucleoplasm (NP) regions. The "Time Measurement" tool was used to determine the mCherry intensities for moonbody variants and GFP intensities for sunbody variants. The fluorescence intensity ratio (FNE/FNP) was used as readout, with the changes in the ratio plotted as F/F0 or ΔF/F0. For spatially-restricted photostimulation, the FRAP module in the Nikon imaging system was used, with the 488-nm laser power output set at 0.2%-5%.

For ligand-controllable nanobodies rapabody and caffebody, similar imaging and data analysis procedures were used. Transfected HeLa cells were incubated with normal growth media or media supplemented with different concentrations of ligands or diluted beverages as indicated in the figures. Coffees and teas were purchased from Starbucks, while other drinks were purchased from a grocery store.

Structural Modeling and Selection of Insertion Sites

Modeled structures of LaM8 and the anti-SH2 monobody were generated by using the I-TASSER server for protein structure and function prediction38. The molecular motion models, the inter-residue contact maps, and the cross-correlation between residue fluctuations of LaM8 and Anti-SH2 monobody were generated by using the DynOmics elastic network models server20. For the molecular motion animations, the following parameters were used: vibrations frequency: 0.05 hz; magnitude: 50; vector scaling: 0.5; vector radius: 14; motion with RMSD of 1 Å. The insertion sites for precise switches were selected based on the mobility/flexibility calculation and/or inter-residue connectivity of the loop regions in selected protein scaffolds using the DynOmics server.

It is contemplated that structural elements undergoing large fluctuations away from their mean positions (high mobility) will provide adequate structural flexibility to accommodate conformational changes and may be allosterically coupled to functional residues.

Calcium Imaging and NFAT Nuclear Translocation Assay

The plasmid mCh-STIM1ct-IRES-caffebody-STIM1ct was co-transfected with green color Ca2+ indicator GCaMP6m into HeLa cells. Images were acquired every 5 sec for both mCh and GFP channels. Ca2+ influx was induced by supplementing 5 μM caffeine to the culture media. Similar caffeine treatment was applied to HeLa cells co-transfected with mCh-STIM1ct-IRES-caffebody-STIM1ct and NFAT-GFP.

Moonbody Regulated Protein Degradation

The plasmid encoding the moonbody fused with the F-box protein atAFB2 was co-transfected with SH2-mEmerald into HeLa cells. Cells were treated with or without a customized blue light source (470 nm, 40 μW/mm2) after 16 h transfection. Light stimulation was applied for 10%(1 min ON, 9 min OFF), 30%(3 min ON, 7 min OFF), or 50%(5 min ON, 5 min OFF). After an additional 16 hours, cells were imaged and SH2-mEmerald mean intensity were measured. Moonbody without atAFB2 was used as control.

SolarFLARE System for Gene Expression

The construct encoding GFP-sunbody fused with TEV protease (GFP-sunbody alone as a control) was co-transfected with PM-mCh-LOV2-TCS-tetR-VP16 and the pTRE-TagBFP reporter in HEK293T cells. Eight hours post-transfection, cells were exposed to pulsed blue light stimulation for 16 h (470 nm, 40 μW/mm2) with a light cycle of 1 min ON and 9 min OFF. Cells kept in the dark was used as a control. Confocal images were acquired after 48 hours transfection with a 10× or 20× air object for mCh, GFP and BFP channels. Eight fields of view were recorded for each condition. GFP expression area was masked and the mean TagBFP intensity was calculated in this mask, with areas outside GFP-positive areas used as background. The background-corrected mean TagBFP intensities were calculated and plotted. For light-inducible necroptosis, the pTRE-TagBFP vector was replaced by the pTRE-MLKL-NT plasmid, with the remaining procedures and conditions identical to the SolarFLARE-BFP reporter experiment described above. To monitor cell death at real-time, live cells were stained with the SYTOX blue dye (Thermo Fisher Scientific, S11348, 1:5000 dilution, Cf=1 μM).

Luciferase Reporter Assay

To examine the efficiency of photoactivatable cytosine base editor (paCBE), the mCh-Cas9n, APOBEC-sunbody-UGI, and pLenti-mU6-Luc2GO-PGK-Neo (as base editing reporter) were co-transfected into HEK293T cells. Cells were treated with blue light (470 nm, 40 μW/mm2, 1 min ON-9 min OFF cycles for 16 h) or kept in the dark 8 hours after transfection. Sunbody alone to replace APOBEC-sunbody-UGI was used as control. 72 h post-transfection, bioluminescence measurements were performed by using a Bright-Glo Luciferase Assay System from Promega (catalog #: E2610) by directly adding reagents to the culture medium at a 1:1 ratio. Five minutes later, the luminescence signals were quantified by using a Cytation 5 Cell Imaging Multi-Mode Reader (BioTek, Winooski, VT, USA).

To monitor caffebody-STIM1ct/mCh-STIM1ct induced NFAT dependent luciferase expression, HEK293T cells were transfected the indicated plasmids and processed 16 h post-transfection. Caffeine and phorbol myristate acetate (PMA) were added to the DMEM medium to a final concentration of 5 μM and 15 nM, respectively. After a 20 min incubation, the solution was removed and the cells were washed twice and then cultured in normal DMEM. The luminescence was monitored after an additional 8 h culture.

Rapabody-Induced BFP Expression

HEK293T cells seeded on glass-bottom dishes were co-transfected with rapabody-VP64 (LaM8-VP64 as control), mCh-dCas9, sgRNA (targeting the upstream mini-promoter of TagBFP reporter) and the TagBFP-reporter. Rapamycin was added to the culture medium to a final concentration of 5 μM and cultured for an additional 24 h. Confocal images were acquired and the mean TagBFP intensity of cells was measured as described for the SolarFLARE system.

Example 6

Design of "Moonbody" Intrabody Compositions

The instant example provides a light-controllable monobody by inserting the LOV2 photoswitch into a fibronectin type III domain (FN3) scaffold that specifically recognizes the Src Homology 2 (SH2) domain of Abelson tyrosine kinase (Abl). Six insertion sites at exposed loop regions with high predicted mobility (FIG. 17A) were selected, with three situated in the antigen-recognizing BC, DE, FG loops (equivalent of complementarity-determining regions (CDRs) seen in an antibody) and the other three at the opposing loops (see FIG. 17B and FIGS. 18A-C). It was contemplated that light-induced conformational changes in LOV2 would allosterically modulate the monobody-target interaction, thereby permitting photoswitchable control of the monobody. To visualize the light-dependent changes in monobody-SH2 association in live cells, the SH2 domain was anchored to the nuclear envelope (NE) via fusion with mEmerald-lamin A, and co-expressed the engineered monobody as a cytosolic protein with partial distribution in the nucleoplasm (NP).

Insertion of LOV2 at Site 4 (DE loop) abolished the monobody-target interaction regardless of the presence of light (FIGS. 17A-D), likely owing to the disruption of the antigen-binding pocket. Insertion of LOV2 at Site 2 (BC loop) led to an appreciable increase (<10%) of nucleoplasmic monobody toward NE-SH2 (see FIGS. 17C-17D and FIG. 18D).

Insertion at flexible loop regions opposing the CDR-like areas, such as S1, S3, and S5, caused varying degrees of light-induced dissociation of moonbody from NE, with the S5 construct showing the highest dynamic change and hence used for further optimization (see FIGS. 17B-17D and FIG. 18D).

Figures 17A, 17B:
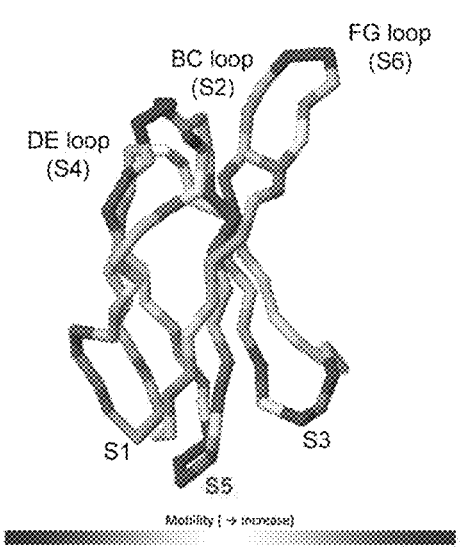

To further enhance the dynamic range of light-induced changes, the linker regions flanking the insertion site and the C-terminal Ja helix within LOV2 were optimized (see FIG. 17B). In particular, a construct (S5.1; FIG. 18C) demonstrated almost complete dissociation from NE upon light stimulation (FIG. 18E) and was called "moonbody" because it retained its antigen-recognition ability in the dark, but rapidly dissociated from the antigen upon light stimulation.

The transferability of this approach was validated by using two additional monobodies that recognize the small ubiquitin-like modifier protein (SUMO) and the maltose-binding protein (MBP). Both engineered moonbodies showed light-induced dissociation from their corresponding target proteins (see FIGS. 19A-19C), suggesting applications in the cost-effective elution or enrichment of recombinant MBP- or SUMO-fusion proteins by switching on and off light, respectively.

Moonbody generation provided control of antibody-antigen recognition with high spatial and temporal precision. The feasibility of spatial control was confirmed by alternatively focusing the photostimulation upon two individual cells under the same imaging field (FIG. 18F). As anticipated, only the cell within the illuminated area showed light-dependent dispersion of NE-bound moonbody into the nucleoplasm; whereas the other cell without photostimulation showed no appreciable changes in the subcellular distribution of moonbody (FIG. 18F. When the whole imaging field was exposed to light stimulation, both cells showed simultaneous light-dependent monobody redistribution.

The moonbody-target interaction was reversible, as reflected by repeated NE-to-NP translocation of moonbody in response to at least 10 dark-light cycles of photostimulation (FIG. 18G). The activation and deactivation half-lives were determined to be 7.8±0.1 s and 46.5±0.3 s, respectively (FIG. 17E). Together, modular insertion of LOV2 into an FN3-derived monobody provides noninvasive and reversible control of single-domain antibody mimetics by light.

It was then evaluated if moonbody could be utilized to conditionally fine-tune the expression levels of its binding target. The SH2-specific moonbody was fused with the auxin signalling F-box 2 protein (AFB2), a component in the Skp1-Cul-F-Box (SCF) E3 ubiquitin ligase complex that can recruit auxin-inducible degrons for proteasomal degradation. Monobody can directly recognize its target, thus obviating the need for auxin and the fusion of the degron tag to a target protein. This suggests that the light-triggered moonbody-target dissociation can prevent SH2 from being destroyed by the proteasomal degradation machinery (FIG. 18H). Indeed, in the presence of escalating doses of pulsed light stimulation, a gradual recovery of SH2-mEmerald signals was observed in the transfected cells (FIG. 18I), thus establishing the feasibility of using a photoswitchable moonbody to modulate the target protein expression levels in live cells.

Example 7

Design of "Sunbody" Intrabody Compositions

The instant example screens photo-switchable nanobodies using a similar engineering approach and the NE translocation assay (see FIGS. 20A-20B). For this example, an mCherry-specific nanobody (LaM8) was used and LOV2 was inserted into flexible loop regions opposing the CDRs (see FIG. 20B and FIG. 21A), the latter of which are involved in direct antigen recognition and thus remain unperturbed. The constructs S1, S2, and S4 exhibited negligible or little changes (<4%) in the NE translocation assay (see FIGS. 21A-21D), making them less ideal for further optimization.

Figure 20D:
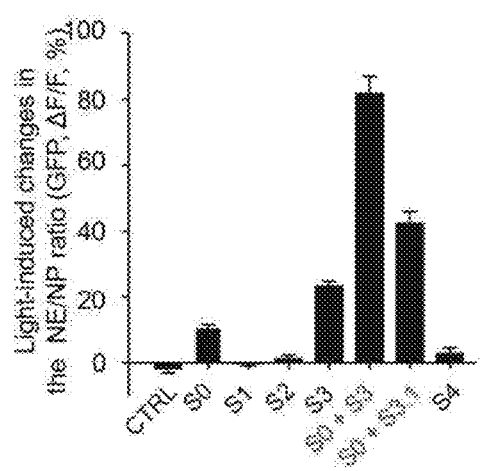
Figures 21A, 21B:
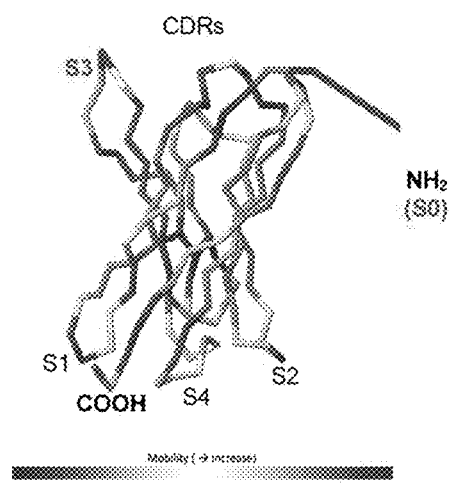
FIGS. 21A-21D show the design and optimization of sunbody variants.
Figures 21C, 21D:
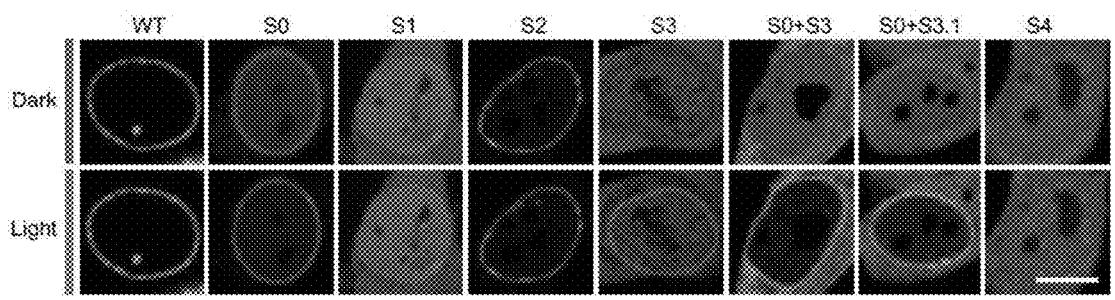

Two complementary approaches were utilized to enhance the light-dependent dynamic changes. First, because the N-terminus of nanobody is close proximity to the CDRs (5-20 Å; S0 site; FIG. 20B), it was contemplated that direct fusion of LOV2 to the N-terminus of nanobody might partially cage its antigen-recognizing ability. Second, both dynamic cross-correlation map and inter-residue connectivity/contact map analyses were performed and identified a domain insertion loop region positioned nearby CDR1 and CDR2 as a potential allosteric site (S3 site; see FIGS. 20B-20C). These engineering efforts led to 10% and 22% increase in the NE/NP ratio after photostimulation, respectively (see FIG. 20D and FIGS. 23A-23D.

Figure 20E:
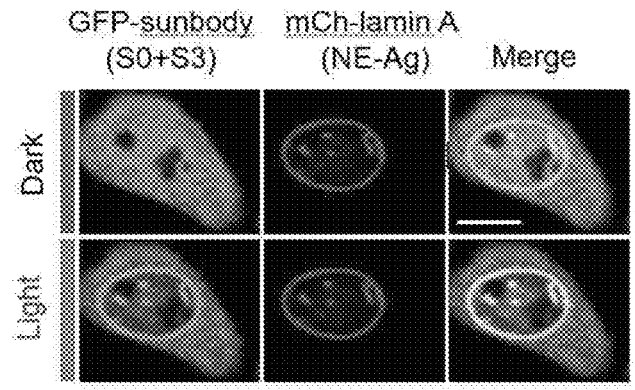
Figure 20F:
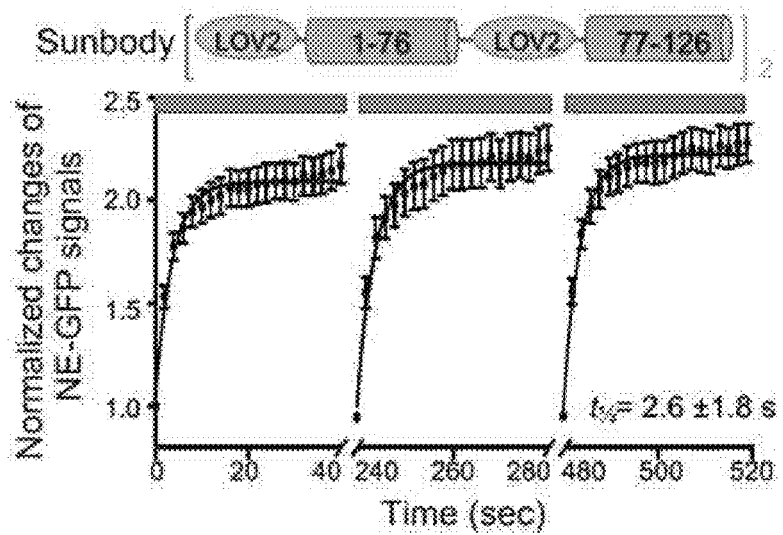
Figure 20G:
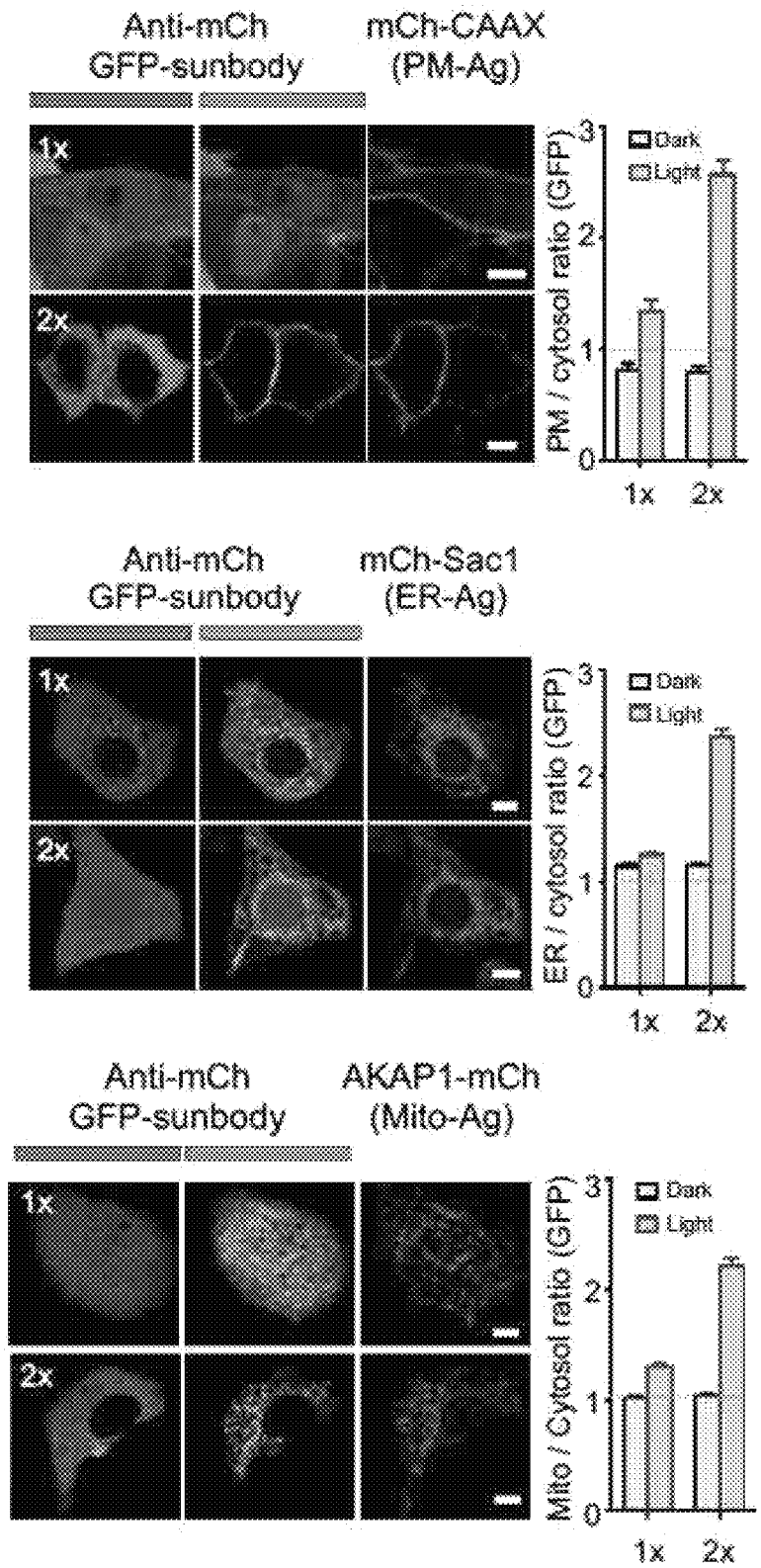

Thereafter, it was evaluated if the simultaneous insertion of LOV2 at S0 and S3 could exert a synergistic effect on nanobody. Indeed, the resultant construct (S0+S3) displayed over 80% changes in the NE/NP ratio (FIG. 20D). This intrabody composition was designated as "sunbody" since its function is switched in a lighted condition. The engineered sunbody showed no appreciable accumulation at NE in the dark but exhibited strong light-triggered translocation toward NE (t1/2, on=2.6±1.8 s; see FIGS. 20E-20F). The sunbody-antigen association was also found to be reversible (FIG. 20F). Notably, the use of a dimeric concatemer of sunbody (2×sunbody) could further enhance the strength of light-switchable antibody-antigen binding, as reflected by >2-fold increase in the signal-to-background ratio reported by four additional subcellular translocation assays (from cytosol to mitochondria [Mito], plasma membrane [PM], endoplasmic reticulum [ER], or early endosome [EE]; see FIG. 20G). It is contemplated that sunbody can be utilized to interrogate proteins located at different subcellular organelles.

Thereafter, the use of sunbody for remote control of gene expression was explored. Sunbody was combined with the FLARE platform to create a SolarFLARE system for light-inducible transcriptional activation (FIG. 20H). It was hypothesized that light stimulation initiates the translocation of a cytosolic anti-mCh sunbody-TEV hybrid protein toward PM-tethered mCh-FLARE components (mCh-LOV2-TCS-tetR-VP16), and brings TEV in close proximity to the exposed substrate (TEV cleavage site or TCS) to cleave the polypeptide, ultimately releasing the otherwise PM-restricted transcriptional coactivator (tetR-VP16) into the nuclei to recognize the nucleotide tetracycline operator (tetO) sequence and activate gene expression. The photosensitive LOV2 modules embodied in both sunbody and the FLARE system confer tight control over gene transcription using light.

The photo-inducible gene transcription was first validated by using blue fluorescent protein (TagBFP) as a reporter (see FIGS. 20H-20I). In the dark, appreciable TagBFP signals were not observed, attesting to the strict control of the SolarFLARE system. By contrast, a marked increase of TagBFP signals was noted in the light-illuminated group, suggesting that the light-inducible antibody-antigen interaction effectively activate the SolarFLARE system to drive gene expression (FIG. 20I).

Figure 22:
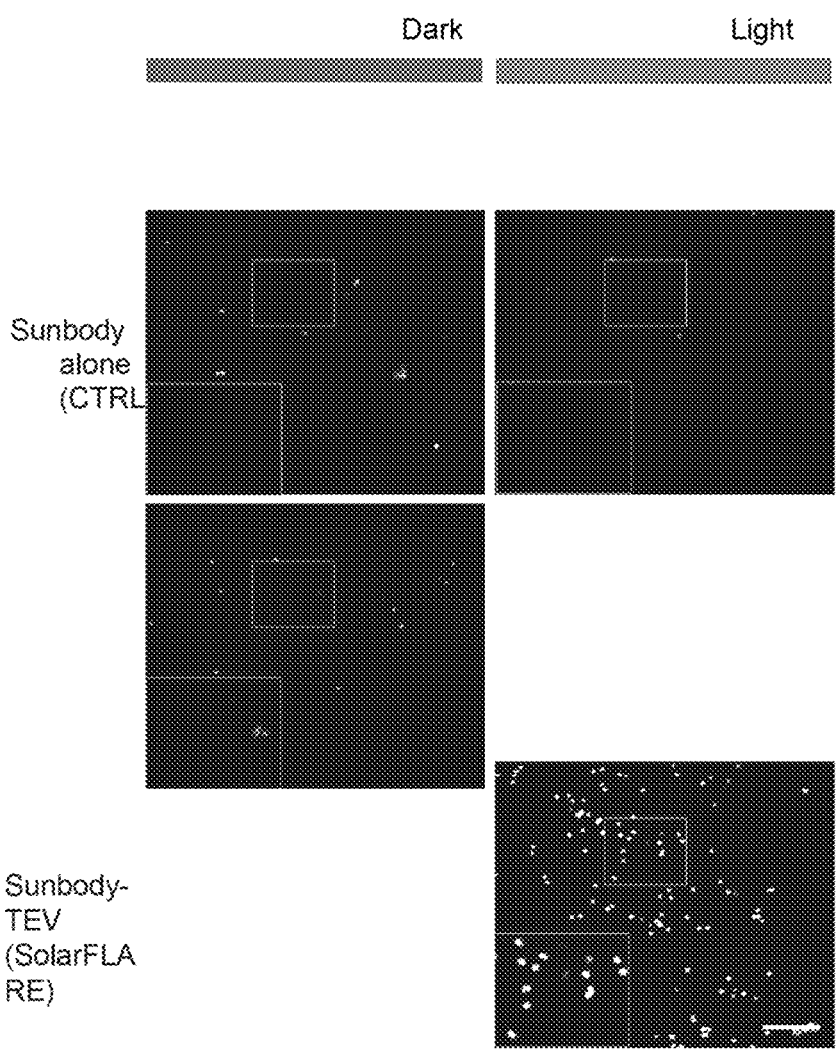
FIG. 22 shows a SolarFLARE system tailored for light-inducible MLKL-NT expression to induce necroptosis. Representative confocal images of HeLa cells transfected with the SolarFLARE system (sunbody-TEV+FLARE; bottom), or the sunbody alone+FLARE combination as control (top), before and after light stimulation. SYTOX Blue staining was used to report dying cells. The quantification results were shown in FIG. 20J. Scale bar, 100 µm.

Next, the TagBFP reporter was replaced by an N-terminal fragment of mixed lineage kinase domain like pseudokinase (MLKL-NT; residues 1-182) that is capable of eliciting necroptotic cell death (necrosis), in order to develop an optogenetic suicide device. Upon light stimulation, a substantial increase of cell death was observed, as reflected by appearance of SYTOX blue staining of the nuclei of dead cells after PM permeabilization by MLKL-NT (see FIG. 20J and FIG. 22). These results establish SolarFLARE as a light-controlled transcriptional programming device.

Thereafter, sunbody was combined with the CRISPR/Cas9-mediated C-to-T base editing technique to design a photoactivatable cytosine base editor (paCBE). The functional units of CBE were split into two parts (FIG. 20K): Part I contained an mCherry-tagged partially enzymatically disabled Cas9 (Cas9 nickase, or Cas9n) with sgRNA (mCh-Cas9n); whereas Part II contained an anti-mCh sunbody fused with the cytidine deaminase APOBEC1 and a uracil DNA glycosylase inhibitor (UGI) to prevent U:G mismatch being repaired back to a C:G base pair. It was contemplated that upon light-triggered sunbody-mCh interaction, paCBE can restore its cytosine-to-thymine editing function. To evaluate, a "Gene ON" (GO) luciferase reporter system was used to monitor the activity of paCBE before and after light stimulation (FIG. 20K). The GO system becomes activated only when a functional CBE converts C to T to create a de novo ATG codon at the beginning of a reporter gene (e.g., luciferase), thereby enabling translational initiation and successful production of the gene.

When the transfected cells were shielded from blue light, notable bioluminescent signals were not observed. Upon photostimulation, a substantial increase of bioluminescence was detected, presumably owing to the expression of luciferase after C>T conversion at the start codon (FIG. 20L). Collectively, this example indicates the successful design of a photoswitchable base editing system by taking advantage of the light-inducible sunbody-antigen interaction.

Example 8

Design of Light- and Caffeine-Operated Intrabody Compositions

The instant example evaluates whether the installation of genetically-encoded chemical switches would likewise enable chemogenetic control of nanobodies. The LOV2 domain in the S3 loop of sunbody was substituted with two ligand-controllable precision switches, UniRapR and a dimeric concatemer of acVHH (2×acVHH; FIG. 23A). UniRapR, engineered from the FKBP-FRB based chemically-inducible dimerization system, has been used to enable rapamycin-induced allosteric control of a wide range of host proteins, including kinases and GTPases. Further, acVHH is known to induce self-dimerization upon addition of caffeine, and thus it was hypothesized to elicit conformational changes when inserted into a host protein as a dimeric concatemer. These intrabody compositions were named "rapabodies" and "caffebodies", respectively, to reflect the compounds used for chemogenetic manipulation.

Figure 23E:
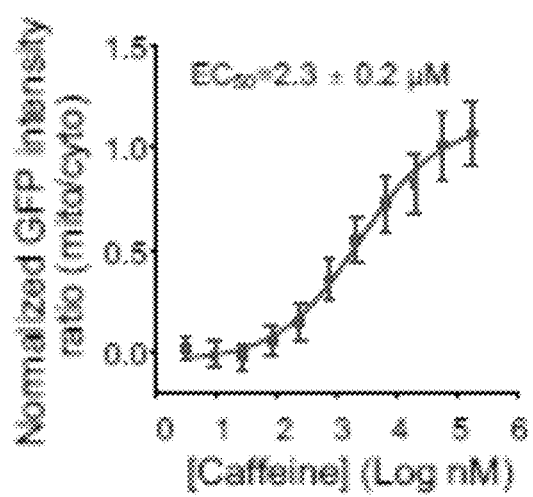

When expressed in HeLa cells by using mitochondria-anchored mCherry (Mito-mCh) as the antigen, contrasting behaviors between rapabody and caffebody were observed (FIG. 23B). Rapabody acted as a chemogenetic OFF-switch, which showed tight binding to Mito-mCh in the absence of rapamycin and rapidly undocked from its binding partner upon rapamycin treatment (t1/2, on=11.0±0.3 s; FIGS. 23B-23C). Alternatively, caffebody functioned as an ON-switch, demonstrating even distribution in the cytosol but underwent rapid translocation toward the mitochondria-tethered antigen upon the addition of caffeine (t1/2, on=16.3±2.3 s; FIGS. 23B-23C). This process is reversible as residual caffeine can be washed away in the culture media and the caffeine-inducible caffebody-antigen association can be repeated in the same cells (FIGS. 24A-24B). The median effective concentrations (EC50) were determined to be 1.6±0.1 μM and 2.3±0.2 μM, respectively, for rapabody and caffebody (FIGS. 23D-23E).

Figure 24C:
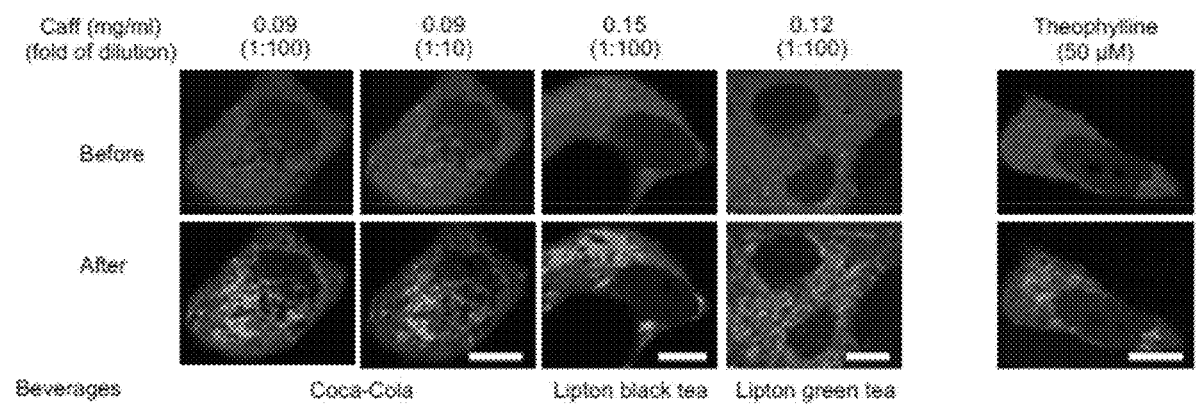

The amount of caffeine intake from daily beverages ranges from 50-350 mg in a typical cup of coffee or a can of soda drink, which corresponds to the optimal activation window of caffebody. Thus, the possible use of beverages to modulate the caffebody-antigen interaction in live cells by using the same mitochondria-translocation assay was evaluated. Following the addition of diluted coffee, tea, soda and energy drinks into the cell culture medium, varying degrees of cytosol-to-mitochondria translocation of the caffebody were observed (FIG. 23F and FIG. 24C). Methylxanthines such as theophylline, a class of caffeine analogs routinely used to treat asthma and chronic obstructive pulmonary disease, could similarly activate caffebody (FIG. 24C). Furthermore, a strong positive correlation between the relative strengths of antibody-antigen binding and the caffeine amounts present in diluted beverages was observed (FIG. 23G).

Figure 23H:
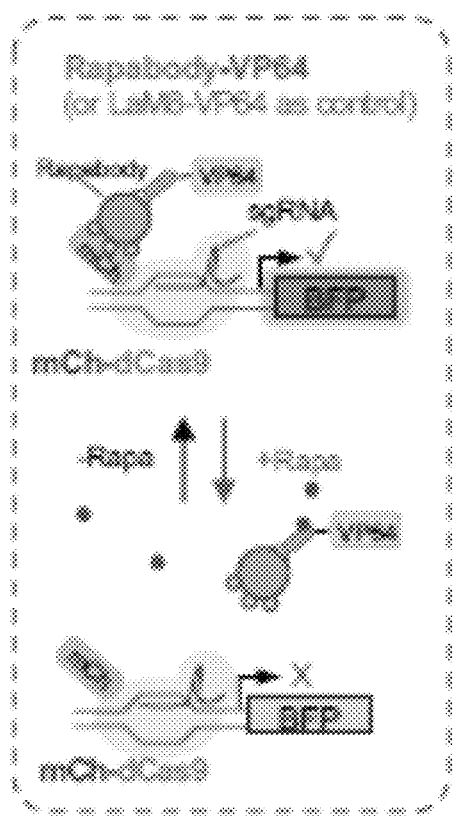

Finally, employing rapabody for drug-inducible control of the assembly of a functional CRISPRa system based on dCas9 and VP64 was evaluated (FIG. 23H). A pronounced suppression of the reporter gene expression (TagBFP) in cells transfected with rapabody-VP64 and mCh-dCas9 was observed but not in the control group using non-drug responsive LaM8-VP64 (FIGS. 23I-23J).

Figure 23K:
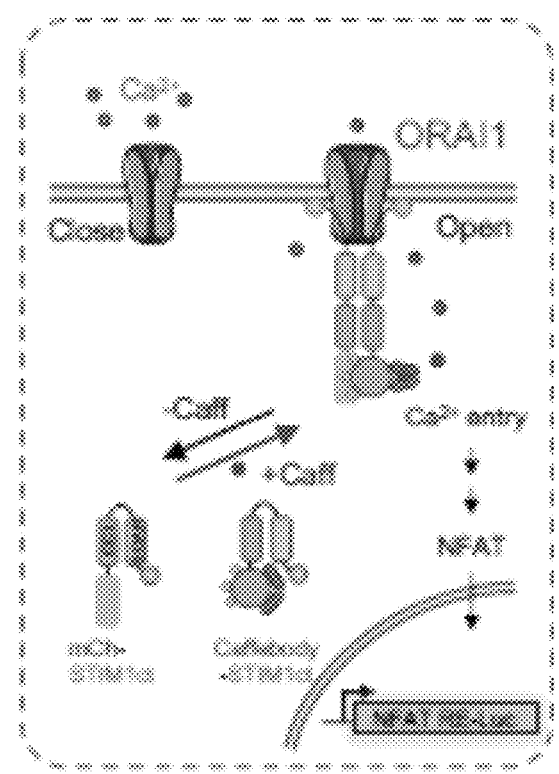
Figure 24D:
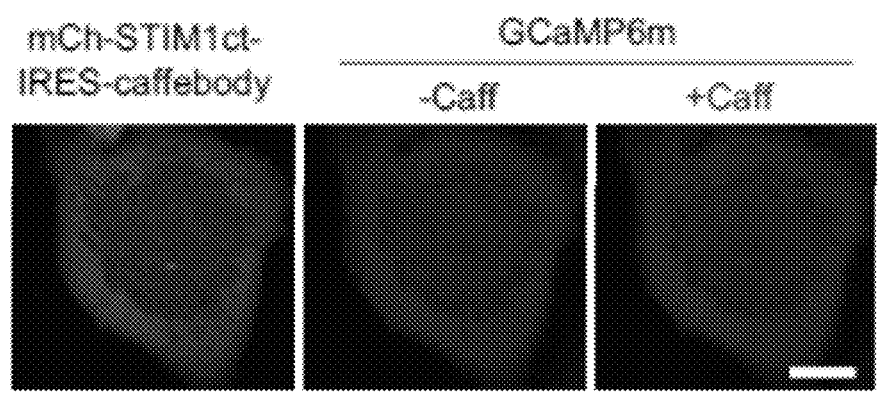

In parallel, the use of caffebody to gate Ca2+ channels and control Ca2+-dependent gene transcription mediated by the downstream nuclear factor of activated T-cells (NFAT) was evaluated. Briefly, the Ca2+ release-activated Ca2+(CRAC) channel was utilized as an engineering target, which is comprised of two essential components, the stromal interaction molecule 1 (STIM1) as the channel activator and the ORAI1 protein as the pore-forming subunit to mediate Ca2+ influx across the plasma membrane (PM). Because forced apposition of the N-terminal coiled coil region 1 (CC1) of the cytoplasmic domain of STIM1 (STIM1ct) effectively overcomes intramolecular trapping of STIM1 to engage and activate the ORAI channels, it was contemplated that caffeine-induced heterodimerization between caffebody-STIM1ct and mCh-STIM1ct could activate endogenous ORAI Ca2+ channels (FIG. 23K). Following 5 μM caffeine treatment, HeLa cells co-expressing both components displayed a pronounced increase of Ca2+ influx (reported by GCaMP6m; FIG. 23L), accompanied with nuclear translocation of NFAT-GFP (FIG. 23L). As a consequence, strong caffeine-induced expression of luciferase as a reporter gene under the control of NFAT response elements was observed (FIG. 23M). As control, the low dose of caffeine used in our assay did not elicit appreciable Ca2+ influx (FIG. 24D), nor did it trigger Ca2+-dependent reporter gene expression in HEK293 cells co-expressing caffebody and mCh-STIM1ct (FIG. 23M). In aggregate, both rapabody and caffebody can be repurposed for remote control of gene expression or ion channel activity to achieve tailored function.

What is claimed is:

1. An intrabody composition comprising i) an intrabody and ii) one or more inserts, wherein the intrabody composition comprises SEQ ID NO:5.

2. The intrabody composition of claim 1, wherein the intrabody is a monobody or a nanobody.

3. The intrabody composition of claim 2, wherein the insert is a protein or a protein fragment, and wherein the protein or the protein fragment is selected from the group consisting of a LOV2 fragment, a circularly permuted version of cpLOV2, acVHH, an acVHH variant, and UniRapR.

4. The intrabody composition of claim 2, wherein the insert comprises two inserts, wherein the two inserts are contacted via a linker.

5. The intrabody composition of claim 1, wherein the intrabody composition is conjugated to a therapeutic agent.

6. The intrabody composition of claim 5, wherein the therapeutic agent is selected from the group consisting of a CAR-T cell, an NK cell, a macrophage, an antibody, an E3 ligase, a TEV protease, and a transcriptional activator VP64.

7. The intrabody composition of claim 1, wherein the intrabody composition is adapted for activation by light or adapted for deactivation by light.

8. The intrabody composition of claim 1, wherein the intrabody composition is activated by a chemical.

9. The intrabody composition of claim 8, wherein the chemical is caffeine, a caffeine metabolite, or a caffeine analog.

10. The intrabody composition of claim 1, wherein the intrabody composition induces a protein-protein interaction.

11. The intrabody composition of claim 10, wherein the protein-protein interaction comprises association of a first protein to a second protein or disassociation of a first protein to a second protein.

12. The intrabody composition of claim 1, wherein the intrabody composition controls binding of an antigen to an antibody.

13. The intrabody composition of claim 1, wherein the intrabody composition is activated by a chemical, wherein the chemical is caffeine.

14. The intrabody composition of claim 1, wherein the intrabody composition is activated by a chemical, wherein the chemical is a caffeine metabolite.

15. The intrabody composition of claim 1, wherein the intrabody composition is activated by a chemical, wherein the chemical is a caffeine analog.

16. The intrabody composition of claim 5, wherein the therapeutic agent is a CAR-T cell.

17. The intrabody composition of claim 10, wherein the protein-protein interaction comprises CAR expression.

18. The intrabody composition of claim 2, wherein the insert is a protein or a protein fragment, and wherein the protein or the protein fragment is an acVHH dimer.

19. The intrabody composition of claim 2, wherein the insert is a protein or a protein fragment, and wherein the protein or the protein fragment is an acVHH mutant.

20. The intrabody composition of claim 19, wherein the acVHH mutant is acVHH-Y104W.

* * * * *

SEQUENCE LISTING

```
<160> NUMBER OF SEQ ID NOS: 13

<210> SEQ ID NO 1
<211> LENGTH: 243
<212> TYPE: PRT
<213> ORGANISM: Artificial Sequence
<220> FEATURE:
<223> OTHER INFORMATION: Synthetic construct

<400> SEQUENCE: 1

Val Ser Ser Val Pro Thr Lys Leu Glu Val Val Asp Ala Thr Pro Thr
1               5                   10                  15

Ser Leu Lys Ile Ser Trp Asp Ala Tyr Tyr Ser Ser Trp Gln Asn Val
                20                  25                  30

Lys Tyr Tyr Arg Ile Thr Tyr Gly Glu Thr Gly Gly Asp Ser Pro Val
            35                  40                  45

Gln Glu Phe Thr Val Pro Gly Tyr Tyr Ser Thr Ala Thr Ile Ser Gly
        50                  55                  60

Leu Lys Pro Gly Ser Gly Leu Ala Thr Thr Leu Glu Arg Ile Glu Lys
65                  70                  75                  80

Asn Phe Val Ile Thr Asp Pro Arg Leu Pro Asp Asn Pro Ile Ile Phe
                85                  90                  95

Ala Ser Asp Ser Phe Leu Gln Leu Thr Glu Tyr Ser Arg Glu Glu Ile
                100                 105                 110

Leu Gly Arg Asn Cys Arg Phe Leu Gln Gly Pro Glu Thr Asp Arg Ala
            115                 120                 125

Thr Val Arg Lys Ile Arg Asp Ala Ile Asp Asn Gln Thr Glu Val Thr
        130                 135                 140

Val Gln Leu Ile Asn Tyr Thr Lys Ser Gly Lys Lys Phe Trp Asn Leu
145                 150                 155                 160

Phe His Leu Gln Pro Met Arg Asp Gln Lys Gly Asp Val Gln Tyr Phe
                165                 170                 175

Ile Gly Val Gln Leu Asp Gly Thr Glu His Val Arg Asp Ala Ala Glu
                180                 185                 190

Arg Glu Gly Val Met Leu Ile Lys Lys Thr Ala Glu Asn Ile Asp Glu
            195                 200                 205

Ala Ala Lys Glu Leu Gly Val Asp Tyr Thr Ile Thr Val Tyr Ala Tyr
        210                 215                 220

Asp Thr Phe Phe Pro Gly Tyr Glu Pro Asn Ser Pro Ile Ser Ile Asn
225                 230                 235                 240

Tyr Arg Thr

<210> SEQ ID NO 2
<211> LENGTH: 407
<212> TYPE: PRT
```

<213> ORGANISM: Artificial Sequence
<220> FEATURE:
<223> OTHER INFORMATION: Synthetic construct

<400> SEQUENCE: 2

```
Leu Ala Thr Thr Leu Glu Arg Ile Glu Lys Asn Phe Val Ile Thr Asp
1               5                   10                  15

Pro Arg Leu Pro Asp Asn Pro Ile Ile Phe Ala Ser Asp Ser Phe Leu
            20                  25                  30

Gln Leu Thr Glu Tyr Ser Arg Glu Ile Leu Gly Arg Asn Cys Arg
        35                  40                  45

Phe Leu Gln Gly Pro Glu Thr Asp Arg Ala Thr Val Arg Lys Ile Arg
50                  55                  60

Asp Ala Ile Asp Asn Gln Thr Glu Val Thr Val Gln Leu Ile Asn Tyr
65                  70                  75                  80

Thr Lys Ser Gly Lys Lys Phe Trp Asn Leu Phe His Leu Gln Pro Met
                85                  90                  95

Arg Asp Gln Lys Gly Asp Val Gln Tyr Phe Ile Gly Val Gln Leu Asp
            100                 105                 110

Gly Thr Glu His Val Arg Asp Ala Ala Glu Arg Glu Gly Val Met Leu
        115                 120                 125

Ile Lys Lys Thr Ala Glu Asn Ile Asp Glu Ala Ala Lys Glu Leu Lys
130                 135                 140

Leu Met Ala Gln Val Gln Leu Val Glu Ser Gly Gly Leu Val Gln
145                 150                 155                 160

Ala Gly Gly Ser Leu Arg Leu Ser Cys Ala Val Ser Gly Arg Pro Phe
                165                 170                 175

Ser Glu Tyr Asn Leu Gly Trp Phe Arg Gln Ala Pro Gly Lys Glu Arg
            180                 185                 190

Glu Phe Val Ala Arg Ile Arg Ser Ser Gly Thr Thr Val Tyr Thr Asp
        195                 200                 205

Ser Val Lys Gly Arg Phe Ser Ala Ser Arg Asp Asn Ala Leu Glu Arg
210                 215                 220

Ile Glu Lys Asn Phe Val Ile Thr Asp Pro Arg Leu Pro Asp Asn Pro
225                 230                 235                 240

Ile Ile Phe Ala Ser Asp Ser Phe Leu Gln Leu Thr Glu Tyr Ser Arg
                245                 250                 255

Glu Glu Ile Leu Gly Arg Asn Cys Arg Phe Leu Gln Gly Pro Glu Thr
            260                 265                 270

Asp Arg Ala Thr Val Arg Lys Ile Arg Asp Ala Ile Asp Asn Gln Thr
        275                 280                 285

Glu Val Thr Val Gln Leu Ile Asn Tyr Thr Lys Ser Gly Lys Lys Phe
290                 295                 300

Trp Asn Leu Phe His Leu Gln Pro Met Arg Asp Gln Lys Gly Asp Val
305                 310                 315                 320

Gln Tyr Phe Ile Gly Val Gln Leu Asp Gly Thr Glu His Val Arg Asp
                325                 330                 335

Ala Ala Glu Arg Glu Gly Val Met Leu Ile Lys Lys Thr Ala Glu Asn
            340                 345                 350

Ile Asp Glu Ala Ala Lys Asn Met Gly Tyr Leu Gln Leu Asn Ser Leu
        355                 360                 365

Glu Pro Glu Asp Thr Ala Val Tyr Tyr Cys Ala Met Ser Arg Val Asp
370                 375                 380

Thr Asp Ser Pro Ala Phe Tyr Asp Tyr Trp Gly Gln Gly Thr Gln Val
```

Thr Val Ser Thr Pro Arg Ser
                    405

<210> SEQ ID NO 3
<211> LENGTH: 420
<212> TYPE: PRT
<213> ORGANISM: Artificial Sequence
<220> FEATURE:
<223> OTHER INFORMATION: Synthetic construct

<400> SEQUENCE: 3

Met Ala Gln Val Gln Leu Val Glu Ser Gly Gly Gly Leu Val Gln Ala
1               5                   10                  15

Gly Gly Ser Leu Arg Leu Ser Cys Ala Val Ser Gly Arg Pro Phe Ser
            20                  25                  30

Glu Tyr Asn Leu Gly Trp Phe Arg Gln Ala Pro Gly Lys Glu Arg Glu
        35                  40                  45

Phe Val Ala Arg Ile Arg Ser Ser Gly Thr Thr Val Tyr Thr Asp Ser
    50                  55                  60

Val Lys Gly Arg Phe Ser Ala Ser Arg Asp Asn Ala Glu Val Gln Leu
65                  70                  75                  80

Gln Ala Ser Gly Gly Gly Leu Val Gln Ala Gly Gly Ser Leu Arg Leu
                85                  90                  95

Ser Cys Thr Ala Ser Gly Arg Thr Gly Thr Ile Tyr Ser Met Ala Trp
            100                 105                 110

Phe Arg Gln Ala Pro Gly Lys Glu Arg Glu Phe Leu Ala Thr Val Gly
        115                 120                 125

Trp Ser Ser Gly Ile Thr Tyr Tyr Met Asp Ser Val Lys Gly Arg Phe
130                 135                 140

Thr Ile Ser Arg Asp Asn Ala Lys Asn Ser Ala Tyr Leu Gln Met Asn
145                 150                 155                 160

Ser Leu Lys Pro Glu Asp Thr Ala Val Tyr Tyr Cys Thr Ala Thr Arg
                165                 170                 175

Ala Tyr Ser Val Gly Tyr Asp Tyr Trp Gly Gln Gly Thr Gln Val Thr
            180                 185                 190

Val Ser His Ala Ala Ala Gly Ala Pro Val Pro Tyr Pro Asp Pro Leu
        195                 200                 205

Glu Pro Arg Glu Gln Lys Leu Ile Ser Glu Glu Asp Leu Leu Glu Ala
    210                 215                 220

Val Tyr Ser Gly Gly Gly Gly Gly Gly Ser Gly Gly Gly Gly Gly Gly
225                 230                 235                 240

Gly Gly Ser Gly Gly Gly Gly Gly Gly Ser Gly Glu Val Gln Leu
                245                 250                 255

Gln Ala Ser Gly Gly Gly Leu Val Gln Ala Gly Gly Ser Leu Arg Leu
            260                 265                 270

Ser Cys Thr Ala Ser Gly Arg Thr Gly Thr Ile Tyr Ser Met Ala Trp
        275                 280                 285

Phe Arg Gln Ala Pro Gly Lys Glu Arg Glu Phe Leu Ala Thr Val Gly
    290                 295                 300

Trp Ser Ser Gly Ile Thr Tyr Tyr Met Asp Ser Val Lys Gly Arg Phe
305                 310                 315                 320

Thr Ile Ser Arg Asp Asn Ala Lys Asn Ser Ala Tyr Leu Gln Met Asn
                325                 330                 335

Ser Leu Lys Pro Glu Asp Thr Ala Val Tyr Tyr Cys Thr Ala Thr Arg

```
            340                 345                 350
Ala Tyr Ser Val Gly Tyr Asp Tyr Trp Gly Gln Gly Thr Gln Val Thr
                355                 360                 365

Val Ser Lys Asn Met Gly Tyr Leu Gln Leu Asn Ser Leu Glu Pro Glu
        370                 375                 380

Asp Thr Ala Val Tyr Tyr Cys Ala Met Ser Arg Val Asp Thr Asp Ser
385                 390                 395                 400

Pro Ala Phe Tyr Asp Tyr Trp Gly Gln Gly Thr Gln Val Thr Val Ser
                405                 410                 415

Thr Pro Arg Ser
            420

<210> SEQ ID NO 4
<211> LENGTH: 320
<212> TYPE: PRT
<213> ORGANISM: Artificial Sequence
<220> FEATURE:
<223> OTHER INFORMATION: Synthetic construct

<400> SEQUENCE: 4

Gln Leu Val Glu Ser Gly Gly Gly Leu Val Gln Ala Gly Gly Ser Leu
1               5                   10                  15

Arg Leu Ser Cys Ala Val Ser Gly Arg Pro Phe Ser Glu Tyr Asn Leu
            20                  25                  30

Gly Trp Phe Arg Gln Ala Pro Gly Lys Glu Arg Glu Phe Val Ala Arg
        35                  40                  45

Ile Arg Ser Ser Gly Thr Thr Val Tyr Thr Asp Ser Val Lys Gly Arg
    50                  55                  60

Phe Ser Ala Ser Arg Asp Asn Ala Thr Cys Val Val His Tyr Thr Gly
65                  70                  75                  80

Met Leu Glu Asp Gly Lys Lys Phe Asp Ser Ser Arg Asp Arg Asn Lys
                85                  90                  95

Pro Phe Lys Phe Met Leu Gly Lys Gln Glu Val Ile Arg Gly Trp Glu
            100                 105                 110

Glu Gly Val Ala Gln Met Ser Val Gly Gln Arg Ala Lys Leu Thr Ile
        115                 120                 125

Ser Pro Asp Tyr Ala Tyr Gly Ala Thr Gly His Gly Ser Gly Ser Gly
    130                 135                 140

Ser Gly Val Lys Asp Leu Leu Gln Ala Trp Asp Leu Tyr Tyr His Val
145                 150                 155                 160

Phe Arg Arg Ile Ser Gly Pro Pro Gly Pro Gly Ser Gly Leu Trp His
                165                 170                 175

Glu Met Trp His Glu Gly Leu Glu Glu Ala Ser Arg Leu Tyr Phe Gly
            180                 185                 190

Glu Arg Asn Val Lys Gly Met Phe Glu Val Leu Glu Pro Leu His Ala
        195                 200                 205

Met Met Glu Arg Gly Pro Gln Thr Leu Lys Glu Thr Ser Phe Asn Gln
    210                 215                 220

Ala Tyr Gly Arg Asp Leu Met Glu Ala Gln Glu Trp Cys Arg Lys Tyr
225                 230                 235                 240

Met Lys Ser Gly Ser Gly Gly Ser Gly Ser Gly Ile Ile Pro Pro
                245                 250                 255

His Ala Thr Leu Val Phe Asp Val Glu Leu Leu Lys Leu Glu Lys Asn
            260                 265                 270

Met Gly Tyr Leu Gln Leu Asn Ser Leu Glu Pro Glu Asp Thr Ala Val
```

```
                275                 280                 285
Tyr Tyr Cys Ala Met Ser Arg Val Asp Thr Asp Ser Pro Ala Phe Tyr
    290                 295                 300

Asp Tyr Trp Gly Gln Gly Thr Gln Val Thr Val Ser Thr Pro Arg Ser
305                 310                 315                 320

<210> SEQ ID NO 5
<211> LENGTH: 118
<212> TYPE: PRT
<213> ORGANISM: Artificial Sequence
<220> FEATURE:
<223> OTHER INFORMATION: Synthetic construct

<400> SEQUENCE: 5

Glu Val Gln Leu Gln Ala Ser Gly Gly Gly Leu Val Gln Ala Gly Gly
1               5                   10                  15

Ser Leu Arg Leu Ser Cys Thr Ala Ser Gly Arg Thr Gly Thr Ile Tyr
            20                  25                  30

Ser Met Ala Trp Phe Arg Gln Ala Pro Gly Lys Glu Arg Glu Phe Leu
        35                  40                  45

Ala Thr Val Gly Trp Ser Ser Gly Ile Thr Tyr Tyr Met Asp Ser Val
    50                  55                  60

Lys Gly Arg Phe Thr Ile Ser Arg Asp Asn Ala Lys Asn Ser Ala Tyr
65                  70                  75                  80

Leu Gln Met Asn Ser Leu Lys Pro Glu Asp Thr Ala Val Tyr Tyr Cys
                85                  90                  95

Thr Ala Thr Arg Ala Trp Ser Val Gly Tyr Asp Tyr Trp Gly Gln Gly
            100                 105                 110

Thr Gln Val Thr Val Ser
        115

<210> SEQ ID NO 6
<211> LENGTH: 250
<212> TYPE: PRT
<213> ORGANISM: Artificial Sequence
<220> FEATURE:
<223> OTHER INFORMATION: Synthetic construct

<400> SEQUENCE: 6

Glu Val Gln Leu Gln Ala Ser Gly Gly Gly Leu Val Gln Ala Gly Gly
1               5                   10                  15

Ser Leu Arg Leu Ser Cys Thr Ala Ser Gly Arg Thr Gly Thr Ile Tyr
            20                  25                  30

Ser Met Ala Trp Phe Arg Gln Ala Pro Gly Lys Glu Arg Glu Phe Leu
        35                  40                  45

Ala Thr Val Gly Trp Ser Ser Gly Ile Thr Tyr Tyr Met Asp Ser Val
    50                  55                  60

Lys Gly Arg Phe Thr Ile Ser Arg Asp Asn Ala Lys Asn Ser Ala Tyr
65                  70                  75                  80

Leu Gln Met Asn Ser Leu Lys Pro Glu Asp Thr Ala Val Tyr Tyr Cys
                85                  90                  95

Thr Ala Thr Arg Ala Trp Ser Val Gly Tyr Asp Tyr Trp Gly Gln Gly
            100                 105                 110

Thr Gln Val Thr Val Ser Leu His Arg Ala Glu Gln Ser Leu His Asp
        115                 120                 125

Leu Gly Ala Pro Glu Val Gln Leu Gln Ala Ser Gly Gly Gly Leu Val
    130                 135                 140
```

Gln Ala Gly Gly Ser Leu Arg Leu Ser Cys Thr Ala Ser Gly Arg Thr
145                 150                 155                 160

Gly Thr Ile Tyr Ser Met Ala Trp Phe Arg Gln Ala Pro Gly Lys Glu
            165                 170                 175

Arg Glu Phe Leu Ala Thr Val Gly Trp Ser Ser Gly Ile Thr Tyr Tyr
                180                 185                 190

Met Asp Ser Val Lys Gly Arg Phe Thr Ile Ser Arg Asp Asn Ala Lys
        195                 200                 205

Asn Ser Ala Tyr Leu Gln Met Asn Ser Leu Lys Pro Glu Asp Thr Ala
    210                 215                 220

Val Tyr Tyr Cys Thr Ala Thr Arg Ala Trp Ser Val Gly Tyr Asp Tyr
225                 230                 235                 240

Trp Gly Gln Gly Thr Gln Val Thr Val Ser
                245                 250

<210> SEQ ID NO 7
<211> LENGTH: 270
<212> TYPE: PRT
<213> ORGANISM: Artificial Sequence
<220> FEATURE:
<223> OTHER INFORMATION: Synthetic construct

<400> SEQUENCE: 7

Glu Val Gln Leu Gln Ala Ser Gly Gly Gly Leu Val Gln Ala Gly Gly
1               5                   10                  15

Ser Leu Arg Leu Ser Cys Thr Ala Ser Gly Arg Thr Gly Thr Ile Tyr
            20                  25                  30

Ser Met Ala Trp Phe Arg Gln Ala Pro Gly Lys Glu Arg Glu Phe Leu
        35                  40                  45

Ala Thr Val Gly Trp Ser Ser Gly Ile Thr Tyr Tyr Met Asp Ser Val
    50                  55                  60

Lys Gly Arg Phe Thr Ile Ser Arg Asp Asn Ala Lys Asn Ser Ala Tyr
65                  70                  75                  80

Leu Gln Met Asn Ser Leu Lys Pro Glu Asp Thr Ala Val Tyr Tyr Cys
                85                  90                  95

Thr Ala Thr Arg Ala Trp Ser Val Gly Tyr Asp Tyr Trp Gly Gln Gly
            100                 105                 110

Thr Gln Val Thr Val Ser His Ala Ala Ala Gly Ala Pro Val Pro Tyr
        115                 120                 125

Pro Asp Pro Leu Glu Pro Arg Glu Gln Lys Leu Ile Ser Glu Glu Asp
    130                 135                 140

Leu Gly Gly Ser Gly Gly Ala Pro Glu Val Gln Leu Gln Ala Ser Gly
145                 150                 155                 160

Gly Gly Leu Val Gln Ala Gly Gly Ser Leu Arg Leu Ser Cys Thr Ala
                165                 170                 175

Ser Gly Arg Thr Gly Thr Ile Tyr Ser Met Ala Trp Phe Arg Gln Ala
            180                 185                 190

Pro Gly Lys Glu Arg Glu Phe Leu Ala Thr Val Gly Trp Ser Ser Gly
        195                 200                 205

Ile Thr Tyr Tyr Met Asp Ser Val Lys Gly Arg Phe Thr Ile Ser Arg
    210                 215                 220

Asp Asn Ala Lys Asn Ser Ala Tyr Leu Gln Met Asn Ser Leu Lys Pro
225                 230                 235                 240

Glu Asp Thr Ala Val Tyr Tyr Cys Thr Ala Thr Arg Ala Trp Ser Val
                245                 250                 255

Gly Tyr Asp Tyr Trp Gly Gln Gly Thr Gln Val Thr Val Ser
            260                 265                 270

<210> SEQ ID NO 8
<211> LENGTH: 5
<212> TYPE: PRT
<213> ORGANISM: Artificial Sequence
<220> FEATURE:
<223> OTHER INFORMATION: linker peptide

<400> SEQUENCE: 8

Asp Ile Gly Ala Pro
1               5

<210> SEQ ID NO 9
<211> LENGTH: 7
<212> TYPE: PRT
<213> ORGANISM: Artificial Sequence
<220> FEATURE:
<223> OTHER INFORMATION: linker peptide

<400> SEQUENCE: 9

Asp Ile Gly Ser Gly Ala Pro
1               5

<210> SEQ ID NO 10
<211> LENGTH: 9
<212> TYPE: PRT
<213> ORGANISM: Artificial Sequence
<220> FEATURE:
<223> OTHER INFORMATION: linker peptide

<400> SEQUENCE: 10

Asp Ile Gly Gly Ser Gly Gly Ala Pro
1               5

<210> SEQ ID NO 11
<211> LENGTH: 14
<212> TYPE: PRT
<213> ORGANISM: Artificial Sequence
<220> FEATURE:
<223> OTHER INFORMATION: linker peptide

<400> SEQUENCE: 11

Leu His Arg Ala Glu Gln Ser Leu His Asp Leu Gly Ala Pro
1               5                   10

<210> SEQ ID NO 12
<211> LENGTH: 34
<212> TYPE: PRT
<213> ORGANISM: Artificial Sequence
<220> FEATURE:
<223> OTHER INFORMATION: peptide liker

<400> SEQUENCE: 12

His Ala Ala Ala Gly Ala Pro Val Pro Tyr Pro Asp Pro Leu Glu Pro
1               5                   10                  15

Arg Glu Gln Lys Leu Ile Ser Glu Glu Asp Leu Gly Gly Ser Gly Gly
            20                  25                  30

Ala Pro

<210> SEQ ID NO 13
<211> LENGTH: 28
<212> TYPE: PRT
<213> ORGANISM: Artificial Sequence
<220> FEATURE:

```
<223> OTHER INFORMATION: peptide linker

<400> SEQUENCE: 13

Leu Lys Met Asp Leu Glu Gly Leu His Arg Ala Glu Gln Ser Leu His
1               5                   10                  15

Asp Leu Gln Glu Arg Leu His Lys Ala Gln Glu Glu
            20                  25
```